(12) United States Patent
Kurosawa et al.

(10) Patent No.: US 9,487,583 B2
(45) Date of Patent: Nov. 8, 2016

(54) METHOD FOR SELECTING PLASMA CELLS OR PLASMABLASTS, METHOD FOR PRODUCING TARGET ANTIGEN SPECIFIC ANTIBODIES, AND NOVEL MONOCLONAL ANTIBODIES

(75) Inventors: Nobuyuki Kurosawa, Toyama (JP); Masaharu Isobe, Toyama (JP)

(73) Assignee: NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 0 days.

(21) Appl. No.: 14/008,567

(22) PCT Filed: Mar. 28, 2012

(86) PCT No.: PCT/JP2012/058216
§ 371 (c)(1),
(2), (4) Date: Sep. 30, 2013

(87) PCT Pub. No.: WO2012/133572
PCT Pub. Date: Oct. 4, 2012

(65) Prior Publication Data
US 2014/0031528 A1  Jan. 30, 2014

(30) Foreign Application Priority Data
Mar. 30, 2011 (JP) .................. 2011-075135

(51) Int. Cl.
*C07K 16/26* (2006.01)
*C07K 16/18* (2006.01)
*C12N 5/0781* (2010.01)

(52) U.S. Cl.
CPC ............... *C07K 16/26* (2013.01); *C07K 16/18* (2013.01); *C12N 5/0635* (2013.01); *C07K 2317/10* (2013.01); *C07K 2317/20* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 7,396,915 | B2 * | 7/2008 | Hosokawa et al. | ........ 530/387.7 |
| 2006/0165684 | A1 * | 7/2006 | Utku | ......................... 424/143.1 |
| 2010/0068752 | A1 | 3/2010 | Pande et al. | |
| 2010/0145031 | A1 * | 6/2010 | Lanzavecchia et al. | ... 530/388.1 |
| 2010/0291683 | A1 * | 11/2010 | Chang et al. | ................ 435/455 |
| 2011/0020879 | A1 | 1/2011 | Isobe et al. | |
| 2011/0117609 | A1 | 5/2011 | Kurosawa et al. | |
| 2011/0231960 | A1 | 9/2011 | Sawada et al. | |
| 2011/0294678 | A1 | 12/2011 | Jin et al. | |

FOREIGN PATENT DOCUMENTS

| | | |
|---|---|---|
| CN | 101600793 A | 12/2009 |
| EP | 2551352 A1 | 1/2013 |
| JP | 2005511021 A | 4/2005 |
| JP | 2006509217 A | 3/2006 |
| JP | 2009-034047 | 2/2009 |
| WO | 92/03570 A1 | 3/1992 |
| WO | 03025542 A2 | 3/2003 |
| WO | 2004/051268 A1 | 6/2004 |
| WO | 2004051268 A1 | 6/2004 |
| WO | 2008/045140 A1 | 4/2008 |
| WO | WO 2009/017226 | 2/2009 |
| WO | WO 2009/091048 | 7/2009 |
| WO | WO 2009/110606 | 9/2009 |
| WO | 2009133882 A1 | 11/2009 |
| WO | 2010/056898 A1 | 5/2010 |
| WO | WO 2011/027808 | 3/2011 |
| WO | WO 2011/118579 | 9/2011 |

OTHER PUBLICATIONS

Kirk et al. (JLB 2010 vol. 87, p. 245-255).*
ER-Tracker (Molecular Probes, 2005.*
Cole et al., "ER-Tracker Dye and Bodipy-Brefeldin A Differentiate the Endoplasmic Reticulum and Golgi Bodies From the Tubularvacuole System in Living Hyphae of Pisolithus Tinctorius", Journal of Microscopy, vol. 197, Pt 3, Mar. 2000, pp. 239-248.
Oracki et al., "Plasma cell development and survival", Immunological Reviews, Special Issue: B-Lymphocyte Biology, vol. 237, Issue 1, pp. 140-159, Sep. 2010.
Sanderson et al., "B lymphocytes express and lose syndecan at specific stages of differentiation", Cell Regulation, vol. 1, pp. 27-35, 1989.
International Search Report for corresponding International Application No. PCT/JP2012/058216, Jul. 3, 2012.
International Preliminary Report on Patentability with Translation of Written Opinion of the International Searching Authority for corresponding International Application No. PCT/JP2012/058216, Jul. 3, 2012.
Office Action for Chinese Application No. 201280016777.6, dated Mar. 28, 2012, 19 pages.
Hayakawa et al., "Isolation of high-affinity memory B cells: Phycoerythrin as a probe for antigen-binding cells", Proc. Natl. Acad. Sci. USA, Mar. 1987, vol. 84, pp. 1379-1383.

(Continued)

*Primary Examiner* — Jacob Cheu
(74) *Attorney, Agent, or Firm* — Ditthavong & Steiner, P.C.

(57) ABSTRACT

[Problem] To provide a method that efficiently produces antigen-specific monoclonal antibodies from a wide range of animal species, and to provide a new antigen-specific monoclonal antibody using this technique. [Solution] A nonhuman animal is immunized with a target antigen, lymph fluid or the like is collected from the immunized nonhuman animal, or lymph fluid or the like is collected from a human having antibodies to the target antigen, the collected lymph fluid or the like is combined with (1) a labeled target antigen and (2) a marker that can selectively binds to plasma cells and/or plasmablasts, and cells that have bound to (1) the labeled target antigen and (2) the marker are then selected. The plasma cells and or the plasmablasts that have specifically bound to the target antigen by the method are selected, an gene of an antibody for the target antigen is collected from the selected cells, the base sequence thereof is identified, an antibody or antibody fragment is prepared on the basis of the base sequence of the identified gene, and an antibody or antibody fragment specific to the target antigen is produced.

6 Claims, 6 Drawing Sheets

(56) References Cited

OTHER PUBLICATIONS

Moody et al., "Antigen-Specific B Cell Detection Reagents: Use and Quality Control", NIH Public Access Author Manuscript, Nov. 2008, 13 pages.
Liao et al., "High-throughput isolation of immunoglobulin genes from single human B cells and expression as monoclonal anitbodies", Journal of Virological Methods, Feb. 2009, 9 pages.
Kurosawa et al., "Rapid production of antigen-specific monoclonal antibodies from a variety of animals", BMC Biology, Sep. 2012, 15 pages.
Lin et al., "In vivo antigen-driven plamablast enrichment in combination with anitgen-specific cell sorting to facilitate the isolation of rare monoclonal antibodies from human B cells", Nature America, Inc., Jun. 2014, 15 pages.
Partial Supplementary European Search Report of PCT/JP2012058216, mailed Apr. 24, 2015, 11 pages.
Extended European Search Report for European Patent Application Serial No. 12765048.9, Jul. 10, 2015, pp. 1-23, European Patent Office, Munich, Germany.
Japanese Office Action for related Japanese Patent Application No. 2013-507689 dated Dec. 22, 2015, with English-language summary, 9 Pages.
Tsutsumi, "Plasma Cell—Who on earth are you?", Microscopia, vol. 12, No. 3, 1995, 25 Pages.
Deng et al., "Fluorescent conjugates of brefeldin A selectively stain the endoplasmic reticulum and Golgi complex of living cells", Journal of Histochemistry and Cytochemistry, 1995, vol. 43, No. 9, pp. 907-915.
Invitrogen, "Cell Biology & Imaging", 2004-2005, 3 Pages.
Murakami et al., "Cell biological applications of fluorescent probes", KENBIKYO, 2007, vol. 42, No. 1, 5 Pages.
Takemoto et al., "Ultrastructural and immunohistochemical observations of plasma cells of the human labial glands", with English Abstract, Kawasaki medical journal, 1997, vol. 23, No. 2, 11 Pages.

* cited by examiner

Fig. 1
A
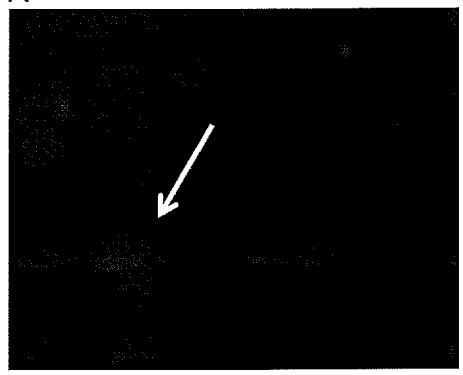
B
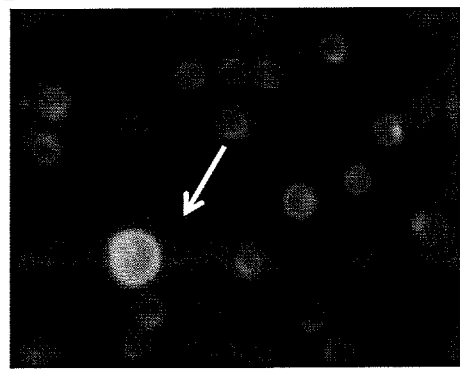
Fig. 2
A
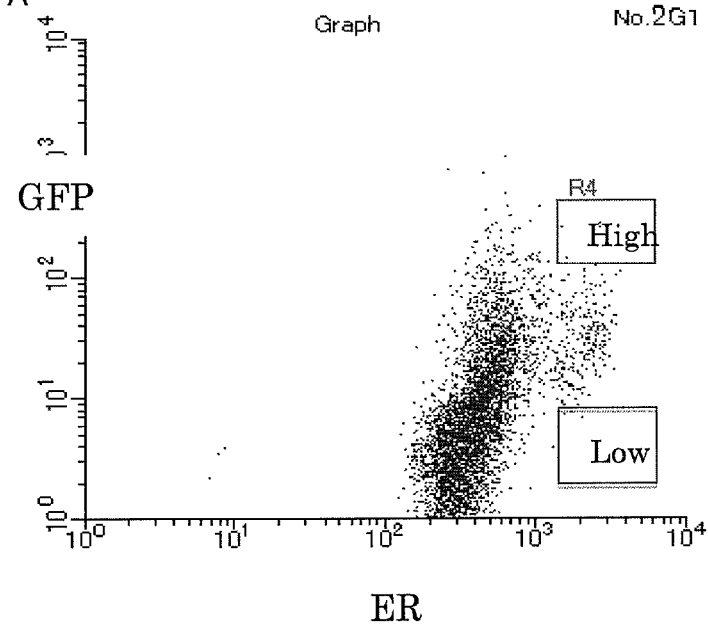
B
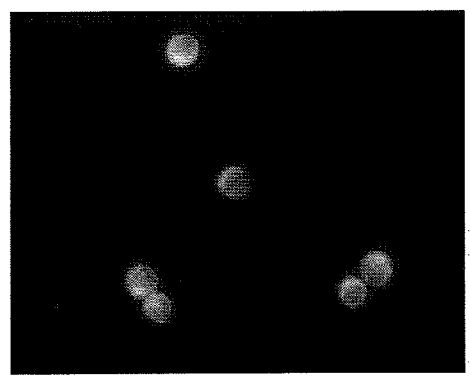

Fig. 5
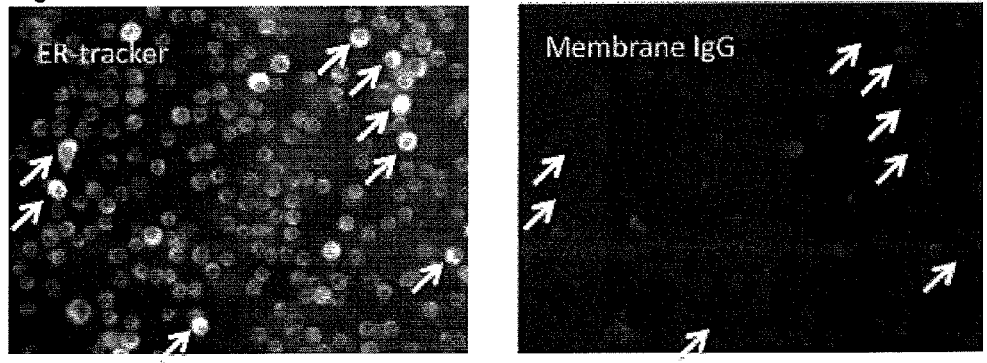
[Fig. 6]
A
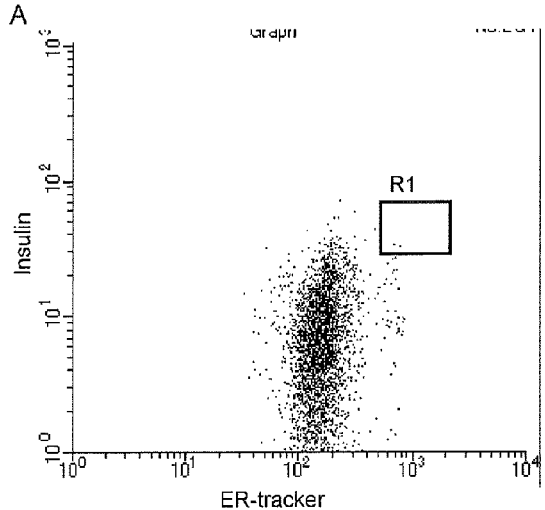
B
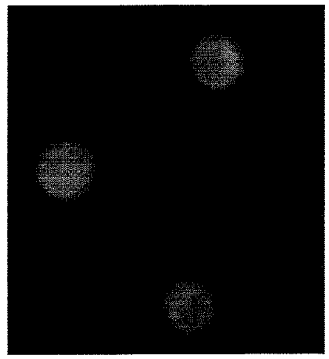

Fig. 11
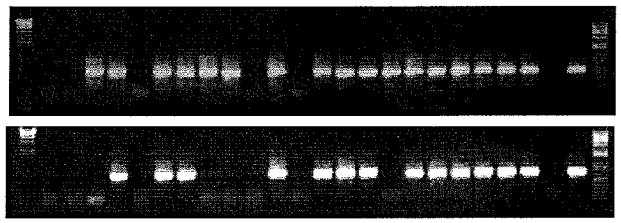
Fig. 12
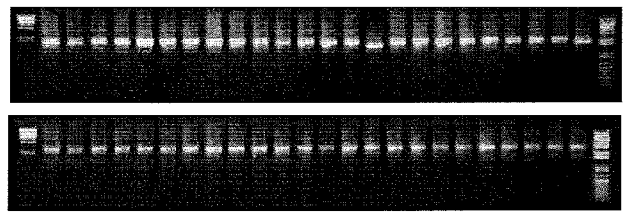
Fig. 13
Production Amount of Recombinant Rabbit Monoclonal Antibodies (μg/ml)
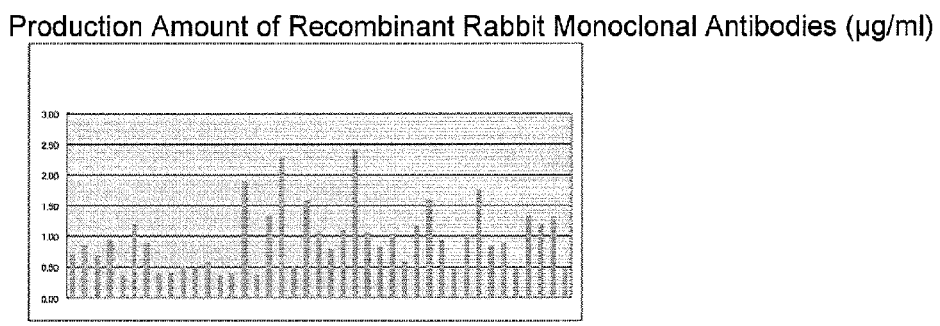
Ovalbumin-binding Ability of Recombinant Rabbit Monoclonal Antibodies (RLU/μg)
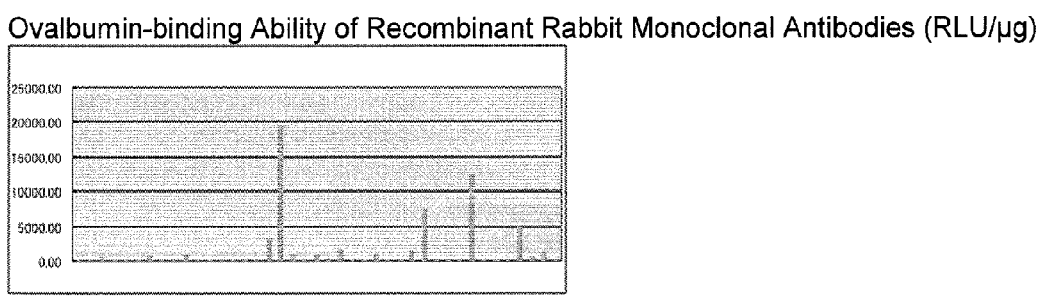

SEQUENCE LISTING

<160> NUMBER OF SEQ ID NOS: 91

<210> SEQ ID NO 1
<211> LENGTH: 911
<212> TYPE: DNA
<213> ORGANISM: Guinea Pig

<400> SEQUENCE: 1
tgcctggtca agggctactt ccctgagccg gtgactgtga aatggaactc aggggccctg        60
accagtggag tgcacacctt cccggccgtc cttcagtcag gcctgtactc actcaccagc       120
atggtaactg tgccctccag ccagaagaag gccacctgca atgtagccca cccggccagc       180
agcaccaagg tggacaagac tgttgagcct attcgaactc ctcaacccaa cccgtgtaca       240
tgtcccaagt gcccacctcc tgaaaacctg ggtggaccat ctgtcttcat cttttccccg       300
aagcccaagg acacgctcat gatctccctg accctaggg tcacatgtgt ggtggtagat       360
gtgagccaag atgagcctga agtccagttc acatggttcg tggacaacaa accggtcggc       420
aatgctgaga caaagccccg agtggagcaa tacaacacga cattccgcgt ggaaagtgtc       480
ctccccatcc agcaccagga ctggctgagg ggcaaggaat tcaagtgcaa ggtctacaac       540
aaagccctgc cagcccccat agagaagacc atctccaaaa ccaaaggggc tccccgcatg       600
ccagatgtgt acacccttcc cccgtcccga gacgagctat ccaagagcaa agtcagtgtg       660
acctgcctga tcatcaactt cttttcctgcc gacatccacg tggagtgggc cagcaatagg       720
gttccagtga gtgagaagga atacaagaac accccaccca ttgaggacgc tgacgggtcc       780
tacttcctct acagcaagct cactgtggat aagagcgcgt gggatcaggg aaccgtctac       840
acctgctccg tgatgcatga agccctgcac aatcatgtca ctcagaaggc catctcccgg       900
tctccgggta a                                                            911

<210> SEQ ID NO 2
<211> LENGTH: 345
<212> TYPE: DNA
<213> ORGANISM: Guinea Pig

<400> SEQUENCE: 2
gggaccaagc tggaaatcaa acggagtgtg cagaagccaa ctatctccct cttccctcca        60
tcatctgagg aggtgacagc tggaagtgcc tcagttgtgt gcttcattaa tagcttctat       120
ccaagagaca tcaccgtcaa gtggaaggtg gatggctctg aacgctcaca aggcatcctg       180
aacagttaca cagatcagga cagcaaggac aacacctaca gcctcagtag caccctggcg       240
ctgacggctt cagagtacaa tcagcatgag aggtacacct gcgaggtctc ccacgctggc       300
ctgacctcac ccgctgccaa gaccatcaac aggagcgagt gctag                       345

<210> SEQ ID NO 3
<211> LENGTH: 273
<212> TYPE: DNA

<213> ORGANISM: Guinea Pig

<400> SEQUENCE: 3

```
gaggagctcc aggacaacaa ggccacagtg gtgtgtctcc tgaattcctt ctaccccggc      60
tctgtgaatg tcagctggaa ggcagatggc accaccatca accagggcgt gcagaccaca     120
cagcctgcca acagagcga caacaaatac atggccagca gctacctgac actgactccc     180
gaccagtgga ggtctcacca gagaatcagc tgccaggtca acacgaggc aggcaatgtg      240
gagaagagtt tggccccgtc agagtgttct taa                                  273
```

<210> SEQ ID NO 4
<211> LENGTH: 303
<212> TYPE: PRT
<213> ORGANISM: Guinea Pig

<400> SEQUENCE: 4

```
Cys Leu Val Lys Gly Tyr Phe Pro Glu Pro Val Thr Val Lys Trp Asn
 1               5                   10                  15

Ser Gly Ala Leu Thr Ser Gly Val His Thr Phe Pro Ala Val Leu Gln
            20                  25                  30

Ser Gly Leu Tyr Ser Leu Thr Ser Met Val Thr Val Pro Ser Ser Gln
        35                  40                  45

Lys Lys Ala Thr Cys Asn Val Ala His Pro Ala Ser Ser Thr Lys Val
    50                  55                  60

Asp Lys Thr Val Glu Pro Ile Arg Thr Pro Gln Pro Asn Pro Cys Thr
65                  70                  75                  80

Cys Pro Lys Cys Pro Pro Glu Asn Leu Gly Gly Pro Ser Val Phe
                85                  90                  95

Ile Phe Pro Pro Lys Pro Lys Asp Thr Leu Met Ile Ser Leu Thr Pro
            100                 105                 110

Arg Val Thr Cys Val Val Val Asp Val Ser Gln Asp Glu Pro Glu Val
        115                 120                 125

Gln Phe Thr Trp Phe Val Asp Asn Lys Pro Val Gly Asn Ala Glu Thr
    130                 135                 140

Lys Pro Arg Val Glu Gln Tyr Asn Thr Thr Phe Arg Val Glu Ser Val
145                 150                 155                 160

Leu Pro Ile Gln His Gln Asp Trp Leu Arg Gly Lys Glu Phe Lys Cys
                165                 170                 175

Lys Val Tyr Asn Lys Ala Leu Pro Ala Pro Ile Glu Lys Thr Ile Ser
            180                 185                 190

Lys Thr Lys Gly Ala Pro Arg Met Pro Asp Val Tyr Thr Leu Pro Pro
        195                 200                 205

Ser Arg Asp Glu Leu Ser Lys Ser Lys Val Ser Val Thr Cys Leu Ile
    210                 215                 220

Ile Asn Phe Phe Pro Ala Asp Ile His Val Glu Trp Ala Ser Asn Arg
225                 230                 235                 240

Val Pro Val Ser Glu Lys Glu Tyr Lys Asn Thr Pro Ile Glu Asp
                245                 250                 255

Ala Asp Gly Ser Tyr Phe Leu Tyr Ser Lys Leu Thr Val Asp Lys Ser
            260                 265                 270

Ala Trp Asp Gln Gly Thr Val Tyr Thr Cys Ser Val Met His Glu Ala
        275                 280                 285

Leu His Asn His Val Thr Gln Lys Ala Ile Ser Arg Ser Pro Gly
    290                 295                 300
```

<210> SEQ ID NO 5
<211> LENGTH: 114
<212> TYPE: PRT
<213> ORGANISM: Guinea Pig

<400> SEQUENCE: 5

Gly Thr Lys Leu Glu Ile Lys Arg Ser Val Gln Lys Pro Thr Ile Ser
1               5                   10                  15
Leu Phe Pro Pro Ser Ser Glu Glu Val Thr Ala Gly Ser Ala Ser Val
            20                  25                  30
Val Cys Phe Ile Asn Ser Phe Tyr Pro Arg Asp Ile Thr Val Lys Trp
        35                  40                  45
Lys Val Asp Gly Ser Glu Arg Ser Gln Gly Ile Leu Asn Ser Tyr Thr
    50                  55                  60
Asp Gln Asp Ser Lys Asp Asn Thr Tyr Ser Leu Ser Thr Leu Ala
65                  70                  75                  80
Leu Thr Ala Ser Glu Tyr Asn Gln His Glu Arg Tyr Thr Cys Glu Val
                85                  90                  95
Ser His Ala Gly Leu Thr Ser Pro Ala Ala Lys Thr Ile Asn Arg Ser
            100                 105                 110
Glu Cys

<210> SEQ ID NO 6
<211> LENGTH: 90
<212> TYPE: PRT
<213> ORGANISM: Guinea Pig

<400> SEQUENCE: 6

Glu Glu Leu Gln Asp Asn Lys Ala Thr Val Val Cys Leu Leu Asn Ser
1               5                   10                  15
Phe Tyr Pro Gly Ser Val Asn Val Ser Trp Lys Ala Asp Gly Thr Thr
            20                  25                  30
Ile Asn Gln Gly Val Gln Thr Thr Gln Pro Ala Lys Gln Ser Asp Asn
        35                  40                  45
Lys Tyr Met Ala Ser Ser Tyr Leu Thr Leu Thr Pro Asp Gln Trp Arg
    50                  55                  60
Ser His Gln Arg Ile Ser Cys Gln Val Lys His Glu Ala Gly Asn Val
65                  70                  75                  80
Glu Lys Ser Leu Ala Pro Ser Glu Cys Ser
                85                  90

<210> SEQ ID NO 7
<211> LENGTH: 351
<212> TYPE: DNA
<213> ORGANISM: Guinea Pig

<400> SEQUENCE: 7
cagatgcagg tgcaggagtc agggcctggc ctggtgaagc cctcacagac cctgttcctt     60
acctgctcag tctctggatt ctccatcaca accagtggtt atgcttggac ctggatccgt    120
cagcctcgag gaaggaccct ggagttggtg ggaggtatag cctacaatgg tggcactggc    180
tacaacccgt ccattaagag ccgcatctcc atctccagag acacaggcaa gaaccagttc    240
tccctccagc tgaactctgt cactgaggaa gacacagcca cttattactg tgcaagaggg    300
cccctatatt ctgttggtcg tgcatggtct aattactggg actttgactt c             351

<210> SEQ ID NO 8

```
<211> LENGTH: 349
<212> TYPE: DNA
<213> ORGANISM: Guinea Pig

<400> SEQUENCE: 8
cagatgcagc tgcaggagtc agggcctggc ctggtgaagc cctcacagac cctgttcctt      60
acctgctcag tctctggatt ctccatcaca accagtggtt atggttggac ctggatccgt     120
cagcctcgag gaaagaccct ggagttgctg gaggtatag cctacaatgg tggcactggc     180
tacaacccgt ccattaagag ccgcatctcc atctccagag acataggcaa gaaccagttc     240
tccctccagc tgaactctgt cactgaggaa gacacagcca ttattactg tgcaagaggg      300 cccctatatt atgttggtcg tgcatggtct aattactggg actttgact              349

<210> SEQ ID NO 9
<211> LENGTH: 351
<212> TYPE: DNA
<213> ORGANISM: Guinea Pig

<400> SEQUENCE: 9
cagatgcagc tacaggagtc agggcctggc ctggtgaagc cctcacagac cctgttcctt      60
acctgctcag tctctggatt ctccatcaca accagtggtt atggttggag ctggatccgt     120
caggctcgag gaaagaccct ggagttgatg gaggtatag cctacaatgg tggcactggc     180
tacaacccgt ccattaagag tcgcatctcc atttctagag acacaggcaa gaaccagttc     240
tccctccagc tgaactctgt cactgaggaa gacacaggca ttattactg tgcaagcggg      300 cccctatatc gtattggtgc tgtatggtct aattaccggt cctttgactt c              351

<210> SEQ ID NO 10
<211> LENGTH: 351
<212> TYPE: DNA
<213> ORGANISM: Guinea Pig

<400> SEQUENCE: 10
cagatgcagc tgcaggagtc agggcctggc ctggtgaagc cctcacagac cctgttcctt      60
acctgctcag tctctggatt ctccatcaca accagtggtt atgcttggac ctggatccgt     120
cagcctcgag gaaagaccct ggagttgatg gaggtatag cctacaatgg tggcactggc     180
tacaacccgt ccattaagag ccgcatctcc atctccagag acacaggcaa gagccagttc     240
tccctccagc tgaactctgt cactgaggaa gacacagcca ttattactg tgcaagaggg      300 cccctatatt atgttggtcg tgcatggtct aattactggg actttgactt c              351

<210> SEQ ID NO 11
<211> LENGTH: 309
<212> TYPE: DNA
<213> ORGANISM: Guinea Pig

<400> SEQUENCE: 11
caggtgcagc tgcaggagtc aggacctggc ctggtgaagc cttcagagac tctgtccctc      60
acttgcaaag tctctggatt ttccttaatg gactatagtg tatcctggat ccgtcaggct     120
ccaggggagg ggctggagtg gattggtgtt atatggagtt ctgggagcac agattataac     180 tcaacctta aatctcgagt gggaatgagc agggacacct ccaagagcca gtctcaatc      240 acactgagga gtctgagttc ggaagacacg gccgtgtatt attgtgcaag ggctcagtac     300
tttgatgta                                                              309
```

<210> SEQ ID NO 12
<211> LENGTH: 348
<212> TYPE: DNA
<213> ORGANISM: Guinea Pig

<400> SEQUENCE: 12

```
cagatgcagc tgcaggagtc agggcctggc ctggtgaagc cctcacagac cctgttcctt    60
agctgctcag tctctgaatt ctccatcaca accagtggtt atggttggag ctggatccgt   120
cagtctcgag aaagaccct  ggaggtgatg ggagagatag cctacaacgg tgccactggc   180
tacaacccgt ccattaagag ccgcatctcc atctccagag acacaggcaa gaaccagttc   240
tccctccatc tgaactctgt cactgaggaa gacacagcca ttattactg  tgcaagatcc   300
ggaagtcata gttcgggtgt ttactatatt cccagttatt ttgatgta              348
```

<210> SEQ ID NO 13
<211> LENGTH: 324
<212> TYPE: DNA
<213> ORGANISM: Guinea Pig

<400> SEQUENCE: 13

```
gaggagcagc tggtggagtc cgggggaggc ttggtgcagc ctgggggttc cctgaaactc    60
tcctgcacgg cctcaggaat gaccctcagt aactatgcga tgagctggat ccgccaggct   120
ccagggaagg ggctggagtg gatctcagct attgttcaca gtggttctaa tacaagatat   180
atagactccg tgaagggccg attcaccatc tccagagaca acgcaggaa  cacgctgtat   240
ttgcagatga gcggcctgag accggaggac acggctgtat attattgtgc aactgatatg   300
ggttggaact cggctttgga tgtt                                         324
```

<210> SEQ ID NO 14
<211> LENGTH: 315
<212> TYPE: DNA
<213> ORGANISM: Guinea Pig

<400> SEQUENCE: 14

```
caggtgcagc tgcaggagtc aggacctggc ctggtgaagc cttcagagac tctgtccctc    60
acttgcaagg tctctggatt ttctttaacc ggctatcctg tatcctggat ccgtcagact   120
ccagggaagg ggctggagct aattggtggt atatggagtt ttggaagcac agaatataac   180
tcagccttta atctcgagt  gggaatcagc aggacactt  ccaacaacca gtctcactc    240
acactgagca gtctgagccc ggaggacacg ccgtttatt  actgtgcaag gcatggcagt   300
gggtattttg atata                                                   315
```

<210> SEQ ID NO 15
<211> LENGTH: 324
<212> TYPE: DNA
<213> ORGANISM: Guinea Pig

<400> SEQUENCE: 15

```
gaggggcagc tggtggagtc cgggggaggc ttggtgcagc ctgggggttc cctgaaactc    60
tcctgcatgg cctcaggact caccctcagt aactatgcga taaattggat ccgtcaggct   120
ccaggaaagg ggctggagtg gatctcagct attagtcaca gtggttctag acaaaactac   180
gcaggctccg ggaagggccg attcaccagt tccagagaca acgcaagaa  tacgatctat   240
ctgcacatga gcagcctgag accggaggac acggctgtct attactgtgc aactgatatg   300
ggttggaact cggctttgga tatc                                         324
```

<210> SEQ ID NO 16
<211> LENGTH: 312
<212> TYPE: DNA
<213> ORGANISM: Guinea Pig

<400> SEQUENCE: 16

```
gtgcagctgc aggagtcagg acctggcctg gtgaagcctt cagagactct gtccctcact    60
tgcaaggtct ctggattttc tttatccggc tatcctgtat cctggatccg tcagactcca   120
ggaaagggc tggaactaat tggtggtata tggccttttg gaggcacaga acataactca   180
gcctttcaat ctcgagtggg gatcagcagg gacacttcca acaacctagt ctcaggcacc   240
cagatcagta tgagcccgga ggacccgtcc attttttgtt gtgcaagcca tggcaatggc   300
tattaggata ta                                                      312
```

<210> SEQ ID NO 17
<211> LENGTH: 309
<212> TYPE: DNA
<213> ORGANISM: Guinea Pig

<400> SEQUENCE: 17

```
caggtgcagc tgcaggagtc agggcctggc ctggtgaagc cttcagagac tctgtccctc    60
acttgcacgg tctctggatt ttctttgacc ggctatagtg tatcctggat ccgtcagact   120
ccagggaagg gctggagtt acttggtggt atatggagtt ttggaagcac agaatataac   180
tcagccttta atctcgaat gggaatcagc aggacactt ccaagaacca ggtctcactc   240
acactgagta gtctgagccc ggaggacacg gccgtatatt actgtgcaag acatggcggt   300
ggctattt                                                            309
```

<210> SEQ ID NO 18
<211> LENGTH: 315
<212> TYPE: DNA
<213> ORGANISM: Guinea Pig

<400> SEQUENCE: 18

```
caggtgcagc tacaggagtc aggacctggc ttggtgaagc cttcagagac tctgtccctc    60
acctgcgagg tctctggatt ttctttaacc ggctatagtg tatcctggat ccgtcagact   120
ccagagaagg gctggaact aattggtggt atatggaatt ttggaggcac agaatataac   180
tcagccttta atctcgagt gggaatcagc aggacactt ccaagaacca agtctcactc   240
acactgagaa atgtgagccc ggaggacacg gccatatatt attgtacaag acatggcagt   300
gggtactttg atatg                                                   315
```

<210> SEQ ID NO 19
<211> LENGTH: 117
<212> TYPE: PRT
<213> ORGANISM: Guinea Pig

<400> SEQUENCE: 19

Gln Met Gln Val Gln Glu Ser Gly Pro Gly Leu Val Lys Pro Ser Gln
1               5                   10                  15

Thr Leu Phe Leu Thr Cys Ser Val Ser Gly Phe Ser Ile Thr Thr Ser
            20                  25                  30

Gly Tyr Ala Trp Thr Trp Ile Arg Gln Pro Arg Gly Arg Thr Leu Glu
        35                  40                  45

Leu Val Gly Gly Ile Ala Tyr Asn Gly Gly Thr Gly Tyr Asn Pro Ser
    50                  55                  60

Ile Lys Ser Arg Ile Ser Ile Ser Arg Asp Thr Gly Lys Asn Gln Phe
65                  70                  75                  80

Ser Leu Gln Leu Asn Ser Val Thr Glu Glu Asp Thr Ala Thr Tyr Tyr
                85                  90                  95

Cys Ala Arg Gly Pro Leu Tyr Ser Val Gly Arg Ala Trp Ser Asn Tyr
            100                 105                 110

Trp Tyr Phe Asp Phe
        115

<210> SEQ ID NO 20
<211> LENGTH: 116
<212> TYPE: PRT
<213> ORGANISM: Guinea Pig

<400> SEQUENCE: 20

Gln Met Gln Leu Gln Glu Ser Gly Pro Gly Leu Val Lys Pro Ser Gln
1               5                   10                  15

Thr Leu Phe Leu Thr Cys Ser Val Ser Gly Phe Ser Ile Thr Thr Ser
            20                  25                  30

Gly Tyr Gly Trp Thr Trp Ile Arg Gln Pro Arg Gly Lys Thr Leu Glu
        35                  40                  45

Leu Leu Gly Gly Ile Ala Tyr Asn Gly Gly Thr Gly Tyr Asn Pro Ser
    50                  55                  60

Ile Lys Ser Arg Ile Ser Ile Ser Arg Asp Ile Gly Lys Asn Gln Phe
65                  70                  75                  80

Ser Leu Gln Leu Asn Ser Val Thr Glu Glu Asp Thr Ala Thr Tyr Tyr
                85                  90                  95

Cys Ala Arg Gly Pro Leu Tyr Tyr Val Gly Arg Ala Trp Ser Asn Tyr
            100                 105                 110

Trp Tyr Phe Asp
        115

<210> SEQ ID NO 21
<211> LENGTH: 117
<212> TYPE: PRT
<213> ORGANISM: Guinea Pig

<400> SEQUENCE: 21

Gln Met Gln Leu Gln Glu Ser Gly Pro Gly Leu Val Lys Pro Ser Gln
1               5                   10                  15

Thr Leu Phe Leu Thr Cys Ser Val Ser Gly Phe Ser Ile Thr Thr Ser
            20                  25                  30

Gly Tyr Gly Trp Ser Trp Ile Arg Gln Ala Arg Gly Lys Thr Leu Glu
        35                  40                  45

Leu Met Gly Gly Ile Ala Tyr Asn Gly Gly Thr Gly Tyr Asn Pro Ser
    50                  55                  60

Ile Lys Ser Arg Ile Ser Ile Ser Arg Asp Thr Gly Lys Asn Gln Phe
65                  70                  75                  80

Ser Leu Gln Leu Asn Ser Val Thr Glu Glu Asp Thr Gly Thr Tyr Tyr
                85                  90                  95

Cys Ala Ser Gly Pro Leu Tyr Arg Ile Gly Ala Val Trp Ser Asn Tyr
            100                 105                 110

Arg Ser Phe Asp Phe
        115

<210> SEQ ID NO 22

```
<211> LENGTH: 117
<212> TYPE: PRT
<213> ORGANISM: Guinea Pig

<400> SEQUENCE: 22

Gln Met Gln Leu Gln Glu Ser Gly Pro Gly Leu Val Lys Pro Ser Gln
1               5                   10                  15

Thr Leu Phe Leu Thr Cys Ser Val Ser Gly Phe Ser Ile Thr Thr Ser
            20                  25                  30

Gly Tyr Ala Trp Thr Trp Ile Arg Gln Pro Arg Gly Lys Thr Leu Glu
        35                  40                  45

Leu Met Gly Gly Ile Ala Tyr Asn Gly Thr Gly Tyr Asn Pro Ser
50                  55                  60

Ile Lys Ser Arg Ile Ser Ile Ser Arg Asp Thr Gly Lys Ser Gln Phe
65                  70                  75                  80

Ser Leu Gln Leu Asn Ser Val Thr Glu Glu Asp Thr Ala Thr Tyr Tyr
                85                  90                  95

Cys Ala Arg Gly Pro Leu Tyr Tyr Val Gly Arg Ala Trp Ser Asn Tyr
            100                 105                 110

Trp Tyr Phe Asp Phe
        115

<210> SEQ ID NO 23
<211> LENGTH: 103
<212> TYPE: PRT
<213> ORGANISM: Guinea Pig

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Leu Met Asp Tyr
            20                  25                  30

Ser Val Ser Trp Ile Arg Gln Ala Pro Gly Glu Gly Leu Glu Trp Ile
        35                  40                  45

Gly Val Ile Trp Ser Ser Gly Ser Thr Asp Tyr Asn Ser Thr Phe Lys
    50                  55                  60

Ser Arg Val Gly Met Ser Arg Asp Thr Ser Lys Ser Gln Val Ser Ile
65                  70                  75                  80

Thr Leu Arg Ser Leu Ser Ser Glu Asp Thr Ala Val Tyr Tyr Cys Ala
                85                  90                  95

Arg Ala Gln Tyr Phe Asp Val
            100

<210> SEQ ID NO 24
<211> LENGTH: 116
<212> TYPE: PRT
<213> ORGANISM: Guinea Pig

<400> SEQUENCE: 24

Gln Met Gln Leu Gln Glu Ser Gly Pro Gly Leu Val Lys Pro Ser Gln
1               5                   10                  15

Thr Leu Phe Leu Ser Cys Ser Val Ser Glu Phe Ser Ile Thr Thr Ser
            20                  25                  30

Gly Tyr Gly Trp Ser Trp Ile Arg Gln Ser Arg Gly Lys Thr Leu Glu
        35                  40                  45

Val Met Gly Glu Ile Ala Tyr Asn Gly Ala Thr Gly Tyr Asn Pro Ser
    50                  55                  60
```

```
Ile Lys Ser Arg Ile Ser Ile Ser Arg Asp Thr Gly Lys Asn Gln Phe
 65                  70                  75                  80

Ser Leu His Leu Asn Ser Val Thr Glu Glu Asp Thr Ala Thr Tyr Tyr
                 85                  90                  95

Cys Ala Arg Ser Gly Ser His Ser Ser Gly Val Tyr Tyr Ile Pro Ser
            100                 105                 110

Tyr Phe Asp Val
        115

<210> SEQ ID NO 25
<211> LENGTH: 108
<212> TYPE: PRT
<213> ORGANISM: Guinea Pig

<400> SEQUENCE: 25

Glu Glu Gln Leu Val Glu Ser Gly Gly Gly Leu Val Gln Pro Gly Gly
  1               5                  10                  15

Ser Leu Lys Leu Ser Cys Thr Ala Ser Gly Met Thr Leu Ser Asn Tyr
                 20                  25                  30

Ala Met Ser Trp Ile Arg Gln Ala Pro Gly Lys Gly Leu Glu Trp Ile
             35                  40                  45

Ser Ala Ile Val His Ser Gly Ser Asn Thr Arg Tyr Ile Asp Ser Val
 50                  55                  60

Lys Gly Arg Phe Thr Ile Ser Arg Asp Asn Gly Arg Asn Thr Leu Tyr
 65                  70                  75                  80

Leu Gln Met Ser Gly Leu Arg Pro Glu Asp Thr Ala Val Tyr Tyr Cys
                 85                  90                  95

Ala Thr Asp Met Gly Trp Asn Ser Ala Leu Asp Val
            100                 105

<210> SEQ ID NO 26
<211> LENGTH: 105
<212> TYPE: PRT
<213> ORGANISM: Guinea Pig

<400> SEQUENCE: 26

Gln Val Gln Leu Gln Glu Ser Gly Pro Gly Leu Val Lys Pro Ser Glu
  1               5                  10                  15

Thr Leu Ser Leu Thr Cys Lys Val Ser Gly Phe Ser Leu Thr Gly Tyr
                 20                  25                  30

Pro Val Ser Trp Ile Arg Gln Thr Pro Gly Lys Gly Leu Glu Leu Ile
             35                  40                  45

Gly Gly Ile Trp Ser Phe Gly Ser Thr Glu Tyr Asn Ser Ala Phe Lys
 50                  55                  60

Ser Arg Val Gly Ile Ser Arg Asp Thr Ser Asn Asn Gln Val Ser Leu
 65                  70                  75                  80

Thr Leu Ser Ser Leu Ser Pro Glu Asp Thr Ala Val Tyr Tyr Cys Ala
                 85                  90                  95

Arg His Gly Ser Gly Tyr Phe Asp Ile
            100                 105

<210> SEQ ID NO 27
<211> LENGTH: 108
<212> TYPE: PRT
<213> ORGANISM: Guinea Pig

<400> SEQUENCE: 27

Glu Gly Gln Leu Val Glu Ser Gly Gly Gly Leu Val Gln Pro Gly Gly
```

```
1               5                   10                  15
Ser Leu Lys Leu Ser Cys Met Ala Ser Gly Leu Thr Leu Ser Asn Tyr
            20                  25                  30

Ala Ile Asn Trp Ile Arg Gln Ala Pro Gly Lys Gly Leu Glu Trp Ile
            35                  40                  45

Ser Ala Ile Ser His Ser Gly Ser Arg Thr Asn Tyr Ala Gly Ser Gly
            50                  55                  60

Lys Gly Arg Phe Thr Ser Ser Arg Asp Asn Gly Lys Asn Thr Ile Tyr
65                  70                  75                  80

Leu His Met Ser Ser Leu Arg Pro Glu Asp Thr Ala Val Tyr Tyr Cys
            85                  90                  95

Ala Thr Asp Met Gly Trp Asn Ser Ala Leu Asp Ile
            100                 105
```

<210> SEQ ID NO 28
<211> LENGTH: 103
<212> TYPE: PRT
<213> ORGANISM: Guinea Pig

<400> SEQUENCE: 28

```
Val Gln Leu Gln Glu Ser Gly Pro Gly Leu Val Lys Pro Ser Glu Thr
1               5                   10                  15

Leu Ser Leu Thr Cys Lys Val Ser Gly Phe Ser Leu Ser Gly Tyr Pro
            20                  25                  30

Val Ser Trp Ile Arg Gln Thr Pro Gly Lys Gly Leu Glu Leu Ile Gly
            35                  40                  45

Gly Ile Trp Pro Phe Gly Gly Thr Glu His Asn Ser Ala Phe Gln Ser
            50                  55                  60

Arg Val Gly Ile Ser Arg Asp Thr Ser Asn Asn Leu Val Ser Gly Thr
65                  70                  75                  80

Gln Ile Ser Met Ser Pro Glu Asp Pro Ser Ile Phe Cys Cys Ala Ser
            85                  90                  95

His Gly Asn Gly Tyr Asp Ile
            100
```

<210> SEQ ID NO 29
<211> LENGTH: 103
<212> TYPE: PRT
<213> ORGANISM: Guinea Pig

<400> SEQUENCE: 29

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Ser Val Ser Trp Ile Arg Gln Thr Pro Gly Lys Gly Leu Glu Leu Leu
            35                  40                  45

Gly Gly Ile Trp Ser Phe Gly Ser Thr Glu Tyr Asn Ser Ala Phe Lys
            50                  55                  60

Ser Arg Met Gly Ile Ser Arg Asp Thr Ser Lys Asn Gln Val Ser Leu
65                  70                  75                  80

Thr Leu Ser Ser Leu Ser Pro Glu Asp Thr Ala Val Tyr Tyr Cys Ala
            85                  90                  95

Arg His Gly Gly Gly Tyr Phe
            100
```

<210> SEQ ID NO 30
<211> LENGTH: 105
<212> TYPE: PRT
<213> ORGANISM: Guinea Pig

<400> SEQUENCE: 30

Gln Val Gln Leu Gln Glu Ser Gly Pro Gly Leu Val Lys Pro Ser Glu
1               5                   10                  15
Thr Leu Ser Leu Thr Cys Glu Val Ser Gly Phe Ser Leu Thr Gly Tyr
            20                  25                  30
Ser Val Ser Trp Ile Arg Gln Thr Pro Glu Lys Gly Leu Glu Leu Ile
        35                  40                  45
Gly Gly Ile Trp Asn Phe Gly Gly Thr Glu Tyr Asn Ser Ala Phe Lys
    50                  55                  60
Ser Arg Val Gly Ile Ser Arg Asp Thr Ser Lys Asn Gln Val Ser Leu
65                  70                  75                  80
Thr Leu Arg Asn Val Ser Pro Glu Asp Thr Ala Ile Tyr Tyr Cys Thr
                85                  90                  95
Arg His Gly Ser Gly Tyr Phe Asp Met
            100                 105

<210> SEQ ID NO 31
<211> LENGTH: 288
<212> TYPE: DNA
<213> ORGANISM: Guinea Pig

<400> SEQUENCE: 31
gacatccaat tgacacagcc tgcatctaca tctgcatctg tgggagacac agtcaagatc      60
agttgccggg ccagtcagac tattaataat tatttaaact ggtatcagca gaagccaggg     120
caagctccta aactcctgat ctatgggaca aacaatttgc agtctgggat cccatcgagg     180
ttcagtggca gtggatctgg gacagatttc actctcatca tcagcagcct gcggcctgaa     240
gactttgcta cttattactg tcaacagagt aggagtagcc cattcact                  288

<210> SEQ ID NO 32
<211> LENGTH: 288
<212> TYPE: DNA
<213> ORGANISM: Guinea Pig

<400> SEQUENCE: 32
gacatccaat tgacacagcc tgcatctaca tctgcatctg tgggagacac agtcaagatc      60
agttgccgga ccagtcagac tattagtagt tatttaaact ggtatcagca gaaaccaggg     120
caagctccta aactcctaat ctatgggaca aacaatttgc agtctgggat cccatcgagg     180
ttcagtggca gtggatctgg gacagatttc actctcatca tcagcagcct gcggcctgaa     240
gactttgcta cttattactg tcaacagagt aacagtagcc cattcact                  288

<210> SEQ ID NO 33
<211> LENGTH: 288
<212> TYPE: DNA
<213> ORGANISM: Guinea Pig

<400> SEQUENCE: 33
gacatccaat tgacacagcc tgcatctgca tctgcatctg tgggagacac agtcaagatc      60
agttgccggg tcagtcagag tgtcagtagt tacttaaact ggtatcagca gaaaccaggg     120
caagctccta aactcctgat ctattgggca accaatttgc agtctgggat cccatcgagg     180
ttcagtggca gtggatctgg gacagatttc actctcacca tcagcagcct gaagcctgaa     240

```
gactttgcaa cttattactg tcaacaaagt aagactagcc cattcact              288

<210> SEQ ID NO 34
<211> LENGTH: 288
<212> TYPE: DNA
<213> ORGANISM: Guinea Pig

<400> SEQUENCE: 34
gacatccaat tgacacagcc tgcatctgca tctgcatctg tgggagacac agtcaagatc    60
agttgccggg ccagtcagac tattagtagt tatttaaact ggtatcagca gaaaccaggg   120
caagctccta caatcctgat ctatgggaca aacaatttgc agtctgggat cccatcgagg   180
ttcagtggca gtggatctgg gacagatttc actctcatca tcagcagcct gcggcctgaa   240
gactttgcta cttattactg tcaacagagt aggagtagcc cattcact              288

<210> SEQ ID NO 35
<211> LENGTH: 334
<212> TYPE: DNA
<213> ORGANISM: Guinea Pig

<400> SEQUENCE: 35
caaattctcc ccattctact gctctgtgcc acagtgtcca atggacaaat tgtactcacc    60
cagtctccag catccctggc tgcttctcca gggcaaaagg tcaccatcac ctgcacagcc   120
agttccagtg taaacaataa cttcttccac tggtaccaac aaaagccagg agcctctcca   180
accctcctaa tttatcgaac atcaagactg gcctccggag tcccggctcg cttcagtggg   240
agtgggtcag ggacttctta ctctctcaca atcagcagca tggagggtga agatgttgca   300
acctattact gtctgcagtc taatagttac acct                              334

<210> SEQ ID NO 36
<211> LENGTH: 306
<212> TYPE: DNA
<213> ORGANISM: Guinea Pig

<400> SEQUENCE: 36
gactttgtga tgactcagtc tccagcctcc ctgtcagtga cccctggaga gagcacaacc    60
atccgctgca gtccagcca gagtcttctg tcccgttata acaacaagaa caacttggcc   120
tggtaccagc agaaaccagg gcaatctccc aaacttctca tctactgggc atccacccga   180
aacactgggg taccagaccg gttcagtggc agtgggtctg gtaccgattt cactctcaca   240
atcagcagcg tgctggctga agatgtggct gattattact gtatgcaata ttatcatttt   300
cggacc                                                             306

<210> SEQ ID NO 37
<211> LENGTH: 291
<212> TYPE: DNA
<213> ORGANISM: Guinea Pig

<400> SEQUENCE: 37
caaattgtgc tcacccagtc tccagcatcc ctgactgctt ccccagggga gaaggtctcc    60
atcacctgca cagccagctc cagtattagc gaaagctact gcactggta ccaacaaaaa   120 ccaggggcct ctccaaaact cctgatttat agaacgtcag acctggcctc cggagtcccg   180
cctcgcttca gtgggagtgg gtcagggact tctttctctc tcacaatcag cagcatggag   240
aatgaagatg ttgcaaccta ttactgtcaa cagtctacca gttaccggac g           291
```

<210> SEQ ID NO 38
<211> LENGTH: 294
<212> TYPE: DNA
<213> ORGANISM: Guinea Pig

<400> SEQUENCE: 38

```
caaattgtgc tcacccagtc tccagcatcc ctggctgctt ccccagggga gaaggtcacc      60
atcacctgca cagccagttc cagtttaatc aataattatt tgcactggta ccaacaaaag     120
gtaggagcct ctccaaagct cctaatttat agaacatcaa gattggcctc cggagtcccg     180
gctcgcttca gtgggagtgg gtcagggact tcttactctc tcacaatcag cagcatggag     240
ggtgaagatg ttgcaaccta ttactgtcag gagtctagca gttactacgg gacg           294
```

<210> SEQ ID NO 39
<211> LENGTH: 291
<212> TYPE: DNA
<213> ORGANISM: Guinea Pig

<400> SEQUENCE: 39

```
caaattgtgc tcacccagtc tccaacatcc ctggctgctt ccccagggga gaaggtcacc      60
atcacctgca cagccaactc cagtattagc gatagctact tgcactggta ccagcaaaag     120
ccaggagcct ctccaaagct cctgatttat agaacgtcag acgtggcctc cggagtcccg     180
gctcgcttca gtgggagtgg gtcagggact tctttctctc tcacaatcaa cagcgtggag     240
ggtgaagatg ctgcaaccta ttactgtcaa cagtctacca cttaccggac g              291
```

<210> SEQ ID NO 40
<211> LENGTH: 294
<212> TYPE: DNA
<213> ORGANISM: Guinea Pig

<400> SEQUENCE: 40

```
caaattgtgc tcacccagtc tccagcatcc ctggctgctt ccccagggga gaaggtcacc      60
atcacctgca cagccagttc cactttaatc aaaaattatt tgcactggta ccaacaaaag     120
ccaggaacct ctccaaggct cctaatttac agaacatcaa aattggcctc cggagtcccg     180
gctcgcttca gtgggagtgg gtcagggact tcttactctc tcactatcag cagcatggag     240
ggtgaagatg ttgcaaccta ttactgtcag gagtctacca gttactacgg gacg           294
```

<210> SEQ ID NO 41
<211> LENGTH: 294
<212> TYPE: DNA
<213> ORGANISM: Guinea Pig

<400> SEQUENCE: 41

```
caaattgtgc tcacccagtc tccagcatcc ctggctgctt ccccagggga gaaggtcacc      60
atcacctgca cagccagttc caatttaatc aataattact tgcactggta ccaacaaaag     120
ccaggagcct ctccaaagct cctaatttat agaacatcaa gattggcctc cggagtcccg     180
gctcgcttca gtgggagtgg gtcagggact tcttactctc tcacaatcaa caacatggag     240
ggtgaagatg ttgcaacgta tttctgtcag gagtctacta gttactacgg gacg           294
```

<210> SEQ ID NO 42
<211> LENGTH: 294
<212> TYPE: DNA
<213> ORGANISM: Guinea Pig

<400> SEQUENCE: 42

```
caaattgtgc tcacccagtc tccagcatcc ctggctgctt ccccagggga gaaggtcacc    60
atcagctgca cagccagttc cagtttaatc aataattatt tacactggta ccaacaaagg   120
ccaggagcct ctccaaagct cctgatttat cgaacatcaa gattggcctc cggagtcccg   180
gctcggttca gtggcagtgg gtcagggact tattactctc tcacaattag cagcatggag   240
ggtgaagatg ttgcaaccta ttactgccag gagtatacca gttactacgg gacg          294
```

```
<210> SEQ ID NO 43
<211> LENGTH: 96
<212> TYPE: PRT
<213> ORGANISM: Guinea Pig

<400> SEQUENCE: 43
```

Asp Ile Gln Leu Thr Gln Pro Ala Ser Thr Ser Ala Ser Val Gly Asp
1               5                   10                  15

Thr Val Lys Ile Ser Cys Arg Ala Ser Gln Thr Ile Asn Asn Tyr Leu
            20                  25                  30

Asn Trp Tyr Gln Gln Lys Pro Gly Gln Ala Pro Lys Leu Leu Ile Tyr
        35                  40                  45

Gly Thr Asn Asn Leu Gln Ser Gly Ile Pro Ser Arg Phe Ser Gly Ser
    50                  55                  60

Gly Ser Gly Thr Asp Phe Thr Leu Ile Ile Ser Ser Leu Arg Pro Glu
65                  70                  75                  80

Asp Phe Ala Thr Tyr Tyr Cys Gln Gln Ser Arg Ser Ser Pro Phe Thr
                85                  90                  95

```
<210> SEQ ID NO 44
<211> LENGTH: 96
<212> TYPE: PRT
<213> ORGANISM: Guinea Pig

<400> SEQUENCE: 44
```

Asp Ile Gln Leu Thr Gln Pro Ala Ser Thr Ser Ala Ser Val Gly Asp
1               5                   10                  15

Thr Val Lys Ile Ser Cys Arg Thr Ser Gln Thr Ile Ser Ser Tyr Leu
            20                  25                  30

Asn Trp Tyr Gln Gln Lys Pro Gly Gln Ala Pro Lys Leu Leu Ile Tyr
        35                  40                  45

Gly Thr Asn Asn Leu Gln Ser Gly Ile Pro Ser Arg Phe Ser Gly Ser
    50                  55                  60

Gly Ser Gly Thr Asp Phe Thr Leu Ile Ile Ser Ser Leu Arg Pro Glu
65                  70                  75                  80

Asp Phe Ala Thr Tyr Tyr Cys Gln Gln Ser Asn Ser Ser Pro Phe Thr
                85                  90                  95

```
<210> SEQ ID NO 45
<211> LENGTH: 96
<212> TYPE: PRT
<213> ORGANISM: Guinea Pig

<400> SEQUENCE: 45
```

Asp Ile Gln Leu Thr Gln Pro Ala Ser Ala Ser Ala Ser Val Gly Asp
1               5                   10                  15

Thr Val Lys Ile Ser Cys Arg Val Ser Gln Ser Val Ser Ser Tyr Leu
            20                  25                  30

Asn Trp Tyr Gln Gln Lys Pro Gly Gln Ala Pro Lys Leu Leu Ile Tyr
        35                  40                  45

```
Trp Ala Thr Asn Leu Gln Ser Gly Ile Pro Ser Arg Phe Ser Gly Ser
         50                  55                  60

Gly Ser Gly Thr Asp Phe Thr Leu Thr Ile Ser Ser Leu Lys Pro Glu
 65                  70                  75                  80

Asp Phe Ala Thr Tyr Tyr Cys Gln Gln Ser Lys Thr Ser Pro Phe Thr
                 85                  90                  95
```

<210> SEQ ID NO 46
<211> LENGTH: 96
<212> TYPE: PRT
<213> ORGANISM: Guinea Pig

<400> SEQUENCE: 46

```
Asp Ile Gln Leu Thr Gln Pro Ala Ser Ala Ser Val Gly Asp
 1               5                  10                  15

Thr Val Lys Ile Ser Cys Arg Ala Ser Gln Thr Ile Ser Ser Tyr Leu
                 20                  25                  30

Asn Trp Tyr Gln Gln Lys Pro Gly Gln Ala Pro Thr Ile Leu Ile Tyr
             35                  40                  45

Gly Thr Asn Asn Leu Gln Ser Gly Ile Pro Ser Arg Phe Ser Gly Ser
         50                  55                  60

Gly Ser Gly Thr Asp Phe Thr Leu Ile Ile Ser Ser Leu Arg Pro Glu
 65                  70                  75                  80

Asp Phe Ala Thr Tyr Tyr Cys Gln Gln Ser Arg Ser Ser Pro Phe Thr
                 85                  90                  95
```

<210> SEQ ID NO 47
<211> LENGTH: 111
<212> TYPE: PRT
<213> ORGANISM: Guinea Pig

<400> SEQUENCE: 47

```
Gln Ile Leu Pro Ile Leu Leu Leu Cys Ala Thr Val Ser Asn Gly Gln
 1               5                  10                  15

Ile Val Leu Thr Gln Ser Pro Ala Ser Leu Ala Ala Ser Pro Gly Gln
                 20                  25                  30

Lys Val Thr Ile Thr Cys Thr Ala Ser Ser Ser Val Asn Asn Asn Phe
             35                  40                  45

Phe His Trp Tyr Gln Gln Lys Pro Gly Ala Ser Pro Thr Leu Leu Ile
         50                  55                  60

Tyr Arg Thr Ser Arg Leu Ala Ser Gly Val Pro Ala Arg Phe Ser Gly
 65                  70                  75                  80

Ser Gly Ser Gly Thr Ser Tyr Ser Leu Thr Ile Ser Ser Met Glu Gly
                 85                  90                  95

Glu Asp Val Ala Thr Tyr Tyr Cys Leu Gln Ser Asn Ser Tyr Thr
                100                 105                 110
```

<210> SEQ ID NO 48
<211> LENGTH: 102
<212> TYPE: PRT
<213> ORGANISM: Guinea Pig

<400> SEQUENCE: 48

```
Asp Phe Val Met Thr Gln Ser Pro Ala Ser Leu Ser Val Thr Pro Gly
 1               5                  10                  15

Glu Ser Thr Thr Ile Arg Cys Lys Ser Ser Gln Ser Leu Leu Ser Arg
                 20                  25                  30
```

Tyr Asn Asn Lys Asn Asn Leu Ala Trp Tyr Gln Gln Lys Pro Gly Gln
                35                  40                  45

Ser Pro Lys Leu Leu Ile Tyr Trp Ala Ser Thr Arg Asn Thr Gly Val
 50                  55                  60

Pro Asp Arg Phe Ser Gly Ser Gly Ser Gly Thr Asp Phe Thr Leu Thr
 65                  70                  75                  80

Ile Ser Ser Val Leu Ala Glu Asp Val Ala Asp Tyr Tyr Cys Met Gln
                 85                  90                  95

Tyr Tyr His Phe Arg Thr
            100

<210> SEQ ID NO 49
<211> LENGTH: 97
<212> TYPE: PRT
<213> ORGANISM: Guinea Pig

<400> SEQUENCE: 49

Gln Ile Val Leu Thr Gln Ser Pro Ala Ser Leu Thr Ala Ser Pro Gly
 1               5                  10                  15

Glu Lys Val Ser Ile Thr Cys Thr Ala Ser Ser Ser Ile Ser Glu Ser
                20                  25                  30

Tyr Leu His Trp Tyr Gln Gln Lys Pro Gly Ala Ser Pro Lys Leu Leu
                35                  40                  45

Ile Tyr Arg Thr Ser Asp Leu Ala Ser Gly Val Pro Pro Arg Phe Ser
 50                  55                  60

Gly Ser Gly Ser Gly Thr Ser Phe Ser Leu Thr Ile Ser Ser Met Glu
 65                  70                  75                  80

Asn Glu Asp Val Ala Thr Tyr Tyr Cys Gln Gln Ser Thr Ser Tyr Arg
                 85                  90                  95

Thr

<210> SEQ ID NO 50
<211> LENGTH: 98
<212> TYPE: PRT
<213> ORGANISM: Guinea Pig

<400> SEQUENCE: 50

Gln Ile Val Leu Thr Gln Ser Pro Ala Ser Leu Ala Ala Ser Pro Gly
 1               5                  10                  15

Glu Lys Val Thr Ile Thr Cys Thr Ala Ser Ser Ser Leu Ile Asn Asn
                20                  25                  30

Tyr Leu His Trp Tyr Gln Gln Lys Val Gly Ala Ser Pro Lys Leu Leu
                35                  40                  45

Ile Tyr Arg Thr Ser Arg Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Gly Glu Asp Val Ala Thr Tyr Tyr Cys Gln Glu Ser Ser Ser Tyr Tyr
                 85                  90                  95

Gly Thr

<210> SEQ ID NO 51
<211> LENGTH: 97
<212> TYPE: PRT
<213> ORGANISM: Guinea Pig

<400> SEQUENCE: 51

Gln Ile Val Leu Thr Gln Ser Pro Thr Ser Leu Ala Ala Ser Pro Gly
1               5                   10                  15

Glu Lys Val Thr Ile Thr Cys Thr Ala Asn Ser Ser Ile Ser Asp Ser
            20                  25                  30

Tyr Leu His Trp Tyr Gln Gln Lys Pro Gly Ala Ser Pro Lys Leu Leu
        35                  40                  45

Ile Tyr Arg Thr Ser Asp Val Ala Ser Gly Val Pro Ala Arg Phe Ser
    50                  55                  60

Gly Ser Gly Ser Gly Thr Ser Phe Ser Leu Thr Ile Asn Ser Val Glu
65                  70                  75                  80

Gly Glu Asp Ala Ala Thr Tyr Tyr Cys Gln Gln Ser Thr Thr Tyr Arg
                85                  90                  95

Thr

<210> SEQ ID NO 52
<211> LENGTH: 98
<212> TYPE: PRT
<213> ORGANISM: Guinea Pig

<400> SEQUENCE: 52

Gln Ile Val Leu Thr Gln Ser Pro Ala Ser Leu Ala Ala Ser Pro Gly
1               5                   10                  15

Glu Lys Val Thr Ile Thr Cys Thr Ala Ser Ser Thr Leu Ile Lys Asn
            20                  25                  30

Tyr Leu His Trp Tyr Gln Gln Lys Pro Gly Thr Ser Pro Arg Leu Leu
        35                  40                  45

Ile Tyr Arg Thr Ser Lys Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Gly Glu Asp Val Ala Thr Tyr Tyr Cys Gln Glu Ser Thr Ser Tyr Tyr
                85                  90                  95

Gly Thr

<210> SEQ ID NO 53
<211> LENGTH: 98
<212> TYPE: PRT
<213> ORGANISM: Guinea Pig

<400> SEQUENCE: 53

Gln Ile Val Leu Thr Gln Ser Pro Ala Ser Leu Ala Ala Ser Pro Gly
1               5                   10                  15

Glu Lys Val Thr Ile Thr Cys Thr Ala Ser Ser Asn Leu Ile Asn Asn
            20                  25                  30

Tyr Leu His Trp Tyr Gln Gln Lys Pro Gly Ala Ser Pro Lys Leu Leu
        35                  40                  45

Ile Tyr Arg Thr Ser Arg Leu Ala Ser Gly Val Pro Ala Arg Phe Ser
    50                  55                  60

Gly Ser Gly Ser Gly Thr Ser Tyr Ser Leu Thr Ile Asn Asn Met Glu
65                  70                  75                  80

Gly Glu Asp Val Ala Thr Tyr Phe Cys Gln Glu Ser Thr Ser Tyr Tyr
                85                  90                  95

Gly Thr

<210> SEQ ID NO 54
<211> LENGTH: 98

```
<212> TYPE: PRT
<213> ORGANISM: Guinea Pig

<400> SEQUENCE: 54

Gln Ile Val Leu Thr Gln Ser Pro Ala Ser Leu Ala Ala Ser Pro Gly
1               5                   10                  15

Glu Lys Val Thr Ile Ser Cys Thr Ala Ser Ser Ser Leu Ile Asn Asn
                20                  25                  30

Tyr Leu His Trp Tyr Gln Gln Arg Pro Gly Ala Ser Pro Lys Leu Leu
            35                  40                  45

Ile Tyr Arg Thr Ser Arg Leu Ala Ser Gly Val Pro Ala Arg Phe Ser
        50                  55                  60

Gly Ser Gly Ser Gly Thr Tyr Tyr Ser Leu Thr Ile Ser Ser Met Glu
65              70                  75                  80

Gly Glu Asp Val Ala Thr Tyr Tyr Cys Gln Glu Tyr Thr Ser Tyr Tyr
                85                  90                  95

Gly Thr

<210> SEQ ID NO 55
<211> LENGTH: 37
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (37)..(37)
<223> OTHER INFORMATION: n is a, c, g, or t

<400> SEQUENCE: 55
gctagcgcta ccggactcag atccccccccc ccccdn                             37

<210> SEQ ID NO 56
<211> LENGTH: 33
<212> TYPE: DNA
<213> ORGANISM: Artificial sequence
<220> FEATURE:
<223> OTHER INFORMATION: Primer

<400> SEQUENCE: 56
gcaggtgacg gtctggctgg rccaggtgct gga                                 33

<210> SEQ ID NO 57
<211> LENGTH: 30
<212> TYPE: DNA
<213> ORGANISM: Artificial sequence
<220> FEATURE:
<223> OTHER INFORMATION: Primer

<400> SEQUENCE: 57
tcgttcagtg ccatcaatct tccacttgac                                     30

<210> SEQ ID NO 58
<211> LENGTH: 26
<212> TYPE: DNA
<213> ORGANISM: Artificial sequence
<220> FEATURE:
<223> OTHER INFORMATION: Primer

<400> SEQUENCE: 58
cgctagcgct accggactca gatccc                                         26

<210> SEQ ID NO 59
```

<211> LENGTH: 27
<212> TYPE: DNA
<213> ORGANISM: Artificial sequence
<220> FEATURE:
<223> OTHER INFORMATION: Primer

<400> SEQUENCE: 59
ctgcaggaca gctgggaagg tgtgcac                               27

<210> SEQ ID NO 60
<211> LENGTH: 27
<212> TYPE: DNA
<213> ORGANISM: Artificial sequence
<220> FEATURE:
<223> OTHER INFORMATION: Primer

<400> SEQUENCE: 60
taactgttcc gtggatggtg ggaagat                               27

<210> SEQ ID NO 61
<211> LENGTH: 27
<212> TYPE: DNA
<213> ORGANISM: Artificial sequence
<220> FEATURE:
<223> OTHER INFORMATION: Primer

<400> SEQUENCE: 61
agagaaaccg tctatcaggg cgatggc                               27

<210> SEQ ID NO 62
<211> LENGTH: 27
<212> TYPE: DNA
<213> ORGANISM: Artificial sequence
<220> FEATURE:
<223> OTHER INFORMATION: Primer

<400> SEQUENCE: 62
agagaccctt tgacgttgga gtccacg                               27

<210> SEQ ID NO 63
<211> LENGTH: 2201
<212> TYPE: DNA
<213> ORGANISM: Artificial sequence
<220> FEATURE:
<223> OTHER INFORMATION: Combined sequence

<400> SEQUENCE: 63
tggaactctg gagccctgtc cagcggtgtg cacaccttcc cagctgtcct gcagtctggg    60
ctctacactc tcaccagctc agtgactgta ccctccagca cctggcccag ccagaccgtc   120
acctgcaacg tagcccaccc ggccagcagc accaaggtgg acaagaaaat tgtgcccaga   180
aactgtggag gtgattgcaa gccttgtata tgtacaggct cagaagtatc atctgtcttc   240
atcttccccc caaagcccaa agatgtgctc accatcactc tgactcctaa ggtcacgtgt   300
gttgtggtag acattagcca ggacgatccc gaggtccatt tcagctggtt tgtagatgac   360
gtggaagtcc acacagctca gactcgacca ccagaggagc agttcaacag cactttccgc   420
tcagtcagtg aactccccat cctgcaccag gactggctca atggcaggac gttcagatgc   480
aaggtcacca gtgcagcttt cccatccccc atcgagaaaa ccatctccaa acccgaaggc   540
agaacacaag ttcgcatgt atacaccatg tcacctacca aggaagagat gacccagaat   600 gaagtcgta tcacctgcat ggtaaaaggc ttctatcccc cagacattta tgtggagtgg   660
cagatgaacg ggcagccaca ggaaaactac aagaacactc cacctacgat ggacacagat   720

```
gggagttact tcctctacag caagctcaat gtgaagaagg aaaaatggca gcagggaaac      780
acgttcacgt gttctgtgct gcatgaaggc ctgcacaacc accatactga aagagtctc      840 tcccactctc cgggtaaatg acccgcggcc gcgactctag atcataatca gccataccac      900
atttgtagag gttttacttg ctttaaaaaa cctcccacac ctccccctga acctgaaaca      960
taaaatgaat gcaattgttg ttgttaactt gtttattgca gcttataatg gttacaaata     1020
aagcaatagc atcacaaatt tcacaaataa agcattttt tcactgcatt ctagttgtgg      1080
tttgtccaaa ctcatcaatg tatcttaagg cgtaaattgt aagcgttaat attttgttaa     1140
aattcgcgtt aaattttgt taaatcagct catttttaa ccataggcc gaaatcggca        1200 aaatcccta taaatcaaaa gaatagaccg atagggtt gagtgttgtt ccagtttgga        1260
acaagagtcc actattaaag aacgtggact ccaacgtcaa agggcgaaaa accgtctatc     1320
agggcgatgg cccactacgt gaaccatcac cctaatcaag ttttttgggg tcgaggtgcc     1380
gtaaagcact aaatcggaac cctaaaggga gcccccgatt tagagcttga cggggaaagc     1440
cggcgaacgt ggcgagaaag gaagggaaga agcgaaagg agcgggcgct agggcgctgg     1500
caagtgtagc ggtcacgctg cgcgtaacca ccacacccgc cgcgcttaat gcgccgctac     1560
agggcgcgtc agatcttagt tattaatagt aatcaattac ggggtcatta gttcatagcc    1620
catatatgga gttccgcgtt acataactta cggtaaatgg cccgcctggc tgaccgccca    1680 acgaccccg cccattgacg tcaataatga cgtatgttcc catagtaacg ccaatagga      1740 ctttccattg acgtcaatgg gtggagtatt tacggtaaac tgcccacttg gcagtacatc    1800
aagtgtatca tatgccaagt acgccccta ttgacgtcaa tgacggtaaa tggcccgcct    1860
ggcattatgc ccagtacatg accttatggg actttcctac ttggcagtac atctacgtat   1920
tagtcatcgc tattaccatg gtgatgcggt tttggcagta catcaatggg cgtggatagc   1980
ggtttgactc acggggattt ccaagtctcc accccattga cgtcaatggg agtttgtttt   2040
ggcaccaaaa tcaacgggac tttccaaaat gtcgtaacaa ctccgcccca ttgacgcaaa   2100
tgggcggtag gcgtgtacgg tgggaggtct atataagcag agctggttta gtgaaccgtc   2160
agatccgcta gcgctaccgg actcagatcc ccccccccc c                        2201
```

<210> SEQ ID NO 64
<211> LENGTH: 1662
<212> TYPE: DNA
<213> ORGANISM: Artificial sequence
<220> FEATURE:
<223> OTHER INFORMATION: Combinded sequence

<400> SEQUENCE: 64

```
gggctgatgc tgcaccaact gtatctatct tcccaccatc cacggaacag ttagcaactg       60
gaggtgcctc agtcgtgtgc ctcatgaaca acttctatcc cagagacatc agtgtcaagt      120
ggaagattga tggcactgaa cgacgagatg gtgtcctgga cagtgttact gatcaggaca      180
gcaaagacag cacgtacagc atgagcagca ccctctcgtt gaccaaggct gactatgaaa      240
gtcataacct ctatacctgt gaggttgttc ataagacatc atcctcaccc gtcgtcaaga      300
gcttcaacag gaatgagtgt tagacgcggc cgcgactcta gatcataatc agccatacca      360
catttgtaga ggttttactt gctttaaaaa acctcccaca cctcccctg aacctgaaac       420 ataaaatgaa tgcaattgtt gttgttaact tgtttattgc agcttataat ggttacaaat      480
aaagcaatag catcacaaat ttcacaaata aagcattttt ttcactgcat tctagttgtg      540
```

```
gtttgtccaa actcatcaat gtatcttaag gcgtaaattg taagcgttaa tatttttgtta      600 aaattcgcgt taaattttg ttaaatcagc tcattttta accaataggc cgaaatcggc         660
aaaatccctt ataaatcaaa agaatagacc gagatagggt tgagtgttgt tccagtttgg      720
aacaagagtc cactattaaa gaacgtggac tccaacgtca aagggcgaaa aaccgtctat      780
cagggcgatg gcccactacg tgaaccatca ccctaatcaa gttttttggg gtcgaggtgc      840
cgtaaagcac taaatcggaa ccctaaaggg agccccgat ttagagcttg acggggaaag       900
ccggcgaacg tggcgagaaa ggaagggaag aaagcgaaag gagcgggcgc tagggcgctg     960
gcaagtgtag cggtcacgct gcgcgtaacc accacacccg ccgcgcttaa tgcgccgcta    1020
cagggcgcgt cagatcttag ttattaatag taatcaatta cggggtcatt agttcatagc    1080
ccatatatgg agttccgcgt tacataactt acggtaaatg gcccgcctgg ctgaccgccc    1140 aacgacccc gcccattgac gtcaataatg acgtatgttc ccatagtaac gccaataggg    1200
actttccatt gacgtcaatg ggtggagtat ttacggtaaa ctgcccactt ggcagtacat    1260
caagtgtatc atatgccaag tacgccccct attgacgtca atgacggtaa atggcccgcc    1320
tggcattatg cccagtacat gaccttatgg gactttccta cttggcagta catctacgta    1380
ttagtcatcg ctattaccat ggtgatgcgg ttttggcagt acatcaatgg gcgtggatag    1440
cggtttgact cacggggatt tccaagtctc cacccccattg acgtcaatgg gagtttgttt    1500
tggcaccaaa atcaacggga ctttccaaaa tgtcgtaaca actccgcccc attgacgcaa    1560
atgggcggta ggcgtgtacg gtgggaggtc tatataagca gagctggttt agtgaaccgt    1620
cagatccgct agcgctaccg gactcagatc cccccccccc cc                       1662

<210> SEQ ID NO 65
<211> LENGTH: 30
<212> TYPE: DNA
<213> ORGANISM: Artificial sequence
<220> FEATURE:
<223> OTHER INFORMATION: Primer

<400> SEQUENCE: 65
ggtgctgctg gccgggtggg ctacattgca                                       30

<210> SEQ ID NO 66
<211> LENGTH: 27
<212> TYPE: DNA
<213> ORGANISM: Artificial sequence
<220> FEATURE:
<223> OTHER INFORMATION: Primer

<400> SEQUENCE: 66
cagagccatc caccttccac ttgacgg                                          27

<210> SEQ ID NO 67
<211> LENGTH: 29
<212> TYPE: DNA
<213> ORGANISM: Artificial sequence
<220> FEATURE:
<223> OTHER INFORMATION: Primer

<400> SEQUENCE: 67
ctgctggcca tgtatttgtt gtcgctctg                                        29

<210> SEQ ID NO 68
<211> LENGTH: 27
<212> TYPE: DNA
<213> ORGANISM: Artificial sequence
```

<220> FEATURE:
<223> OTHER INFORMATION: Primer

<400> SEQUENCE: 68
ctgaaggacg gccgggaagg tgtgcac                                27

<210> SEQ ID NO 69
<211> LENGTH: 32
<212> TYPE: DNA
<213> ORGANISM: Artificial sequence
<220> FEATURE:
<223> OTHER INFORMATION: Primer

<400> SEQUENCE: 69
ggaagaggga gatagttggc ttctgcacac tc                          32

<210> SEQ ID NO 70
<211> LENGTH: 28
<212> TYPE: DNA
<213> ORGANISM: Artificial sequence
<220> FEATURE:
<223> OTHER INFORMATION: Primer

<400> SEQUENCE: 70
agaaggaatt caggagacac accactgt                               28

<210> SEQ ID NO 71
<211> LENGTH: 37
<212> TYPE: DNA
<213> ORGANISM: Artificial sequence
<220> FEATURE:
<223> OTHER INFORMATION: Primer

<400> SEQUENCE: 71
agagactcga gtgcctggtc aagggctact tccctga                     37

<210> SEQ ID NO 72
<211> LENGTH: 38
<212> TYPE: DNA
<213> ORGANISM: Artificial sequence
<220> FEATURE:
<223> OTHER INFORMATION: Primer

<400> SEQUENCE: 72
gagagagcgg ccgctcattt acccggagac cgggagat                    38

<210> SEQ ID NO 73
<211> LENGTH: 36
<212> TYPE: DNA
<213> ORGANISM: Artificial sequence
<220> FEATURE:
<223> OTHER INFORMATION: Primer

<400> SEQUENCE: 73
agagactcga ggggaccaag ctggaaatca aacgga                      36

<210> SEQ ID NO 74
<211> LENGTH: 40
<212> TYPE: DNA
<213> ORGANISM: Artificial sequence
<220> FEATURE:
<223> OTHER INFORMATION: Primer

<400> SEQUENCE: 74
gagagagcgg ccgcctagca ctcgctcctg ttgatggtct                  40

<210> SEQ ID NO 75
<211> LENGTH: 34
<212> TYPE: DNA
<213> ORGANISM: Artificial sequence
<220> FEATURE:
<223> OTHER INFORMATION: Primer

<400> SEQUENCE: 75

```
agagactcga ggaggagctc caggacaaca aggc                                    34
```

<210> SEQ ID NO 76
<211> LENGTH: 37
<212> TYPE: DNA
<213> ORGANISM: Artificial sequence
<220> FEATURE:
<223> OTHER INFORMATION: Primer

<400> SEQUENCE: 76

```
gagagagcgg ccgctaagaa cactctgacg gggccac                                 37
```

<210> SEQ ID NO 77
<211> LENGTH: 2123
<212> TYPE: DNA
<213> ORGANISM: Artificial sequence
<220> FEATURE:
<223> OTHER INFORMATION: Combined sequence

<400> SEQUENCE: 77

```
tgcctggtca agggctactt ccctgagccg gtgactgtga aatggaactc aggggccctg        60
accagtggag tgcacacctt cccggccgtc cttcagtcag gcctgtactc actcaccagc       120
atggtaactg tgccctccag ccagaagaag gccacctgca atgtagccca cccggccagc       180
agcaccaagg tggacaagac tgttgagcct attcgaactc ctcaacccaa cccgtgtaca       240
tgtcccaagt gcccacctcc tgaaaacctg gtggaccat ctgtcttcat ctttccccg        300
aagcccaagg acacgctcat gatctccctg accctagggg tcacatgtgt ggtggtagat      360
gtgagccaag atgagcctga agtccagttc acatggttcg tggacaacaa accggtcggc      420
aatgctgaga caaagccccg agtggagcaa tacaacacga cattccgcgt ggaaagtgtc      480
ctccccatcc agcaccagga ctggctgagg ggcaaggaat tcaagtgcaa ggtctacaac      540
aaagccctgc cagcccccat agagaagacc atctccaaaa ccaagggggc tcccgcatg        600
ccagatgtgt acaccttcc cccgtcccga cgagctat ccaagagcaa agtcagtgtg        660
acctgcctga tcatcaactt ctttcctgcc gacatccacg tggagtgggc cagcaatagg      720
gttccagtga gtgagaagga atacaagaac accccaccca ttgaggacgc tgacgggtcc      780
tacttcctct acagcaagct cactgtggat aagagcgcgt gggatcaggg aaccgtctac      840
acctgctccg tgatgcatga agccctgcac aatcatgtca ctcagaaggc catctcccgg      900
tctccgggta atgagcggc cgcgactcta gatcataatc agccatacca catttgtaga       960
ggttttactt gctttaaaaa acctcccaca cctccccctg aacctgaaac ataaaatgaa     1020
tgcaattgtt gttgttaact tgtttattgc agcttataat ggttacaaat aaagcaatag    1080
catcacaaat ttcacaaata aagcattttt ttcactgcat tctagttgtg gtttgtccaa    1140
actcatcaat gtatcttaag gcgtaaattg taagcgttaa tattttgtta aaattcgcgt    1200
taaatttttg ttaaatcagc tcattttta accataggc cgaaatcggc aaaatccctt     1260
ataaatcaaa agaatagacc gagataggt tgagtgttgt tccagtttgg aacaagagtc     1320
cactattaaa gaacgtggac tccaacgtca aagggcgaaa aaccgtctat cagggcgatg    1380
```

```
gcccactacg tgaaccatca ccctaatcaa gttttttggg gtcgaggtgc cgtaaagcac   1440
taaatcggaa ccctaaaggg agcccccgat ttagagcttg acggggaaag ccggcgaata   1500
gttattaata gtaatcaatt acggggtcat tagttcatag cccatatatg gagttccgcg   1560
ttacataact tacggtaaat ggcccgcctg gctgaccgcc caacgacccc cgcccattga   1620
cgtcaataat gacgtatgtt cccatagtaa cgccaatagg gactttccat tgacgtcaat   1680
gggtggagta tttacggtaa actgcccact tggcagtaca tcaagtgtat catatgccaa   1740
gtacgccccc tattgacgtc aatgacggta aatggcccgc ctggcattat gcccagtaca   1800
tgaccttatg ggactttcct acttggcagt acatctacgt attagtcatc gctattacca   1860
tggtgatgcg gttttggcag tacatcaatg ggcgtggata gcggtttgac tcacggggat   1920
ttccaagtct ccaccccatt gacgtcaatg ggagtttgtt ttggcaccaa aatcaacggg   1980
actttccaaa atgtcgtaac aactccgccc cattgacgca aatgggcggt aggcgtgtac   2040
ggtgggaggt ctatataagc agagctggtt tagtgaaccg tcagatccgc tagcgctacc   2100
ggactcagat cccccccccc ccc                                           2123
```

<210> SEQ ID NO 78
<211> LENGTH: 1682
<212> TYPE: DNA
<213> ORGANISM: Artificial sequence
<220> FEATURE:
<223> OTHER INFORMATION: Combined sequence

<400> SEQUENCE: 78

```
gggaccaagc tggaaatcaa acggagtgtg cagaagccaa ctatctccct cttccctcca     60
tcatctgagg aggtgacagc tggaagtgcc tcagttgtgt gcttcattaa tagcttctat    120
ccaagagaca tcaccgtcaa gtggaaggtg gatggctctg aacgctcaca aggcatcctg    180
aacagttaca cagatcagga cagcaaggac aacacctaca gcctcagtag caccctggcg    240
ctgacggctt cagagtacaa tcagcatgag aggtacacct gcgaggtctc ccacgctggc    300
ctgacctcac ccgctgccaa gaccatcaac aggagcgagt gctaggcggc cgcgactcta    360
gatcataatc agccatacca catttgtaga ggttttactt gctttaaaaa acctcccaca    420
cctccccctg aacctgaaac ataaaatgaa tgcaattgtt gttgttaact tgtttattgc    480
agcttataat ggttacaaat aaagcaatag catcacaaat ttcacaaata aagcattttt    540
ttcactgcat tctagttgtg gtttgtccaa actcatcaat gtatcttaag gcgtaaattg    600
taagcgttaa tattttgtta aaattcgcgt taaatttttg ttaaatcagc tcattttttta   660 accaataggc cgaaatcggc aaaatccctt ataaatcaaa agaatagacc gagatagggt    720
tgagtgttgt tccagtttgg aacaagagtc cactattaaa gaacgtggac tccaacgtca    780
aagggcgaaa aaccgtctat cagggcgatg gcccactacg tgaaccatca ccctaatcaa    840
gttttttggg gtcgaggtgc cgtaaagcac taaatcggaa ccctaaaggg agcccccgat    900
ttagagcttg acggggaaag ccggcgaacg tggcgagaaa ggaagggaag aaagcgaaag    960
gagcgggcgc tagggcgctg gcaagtgtag cggtcacgct gcgcgtaacc accacacccg   1020
ccgcgcttaa tgcgccgcta cagggcgcgt cagatcttag ttattaatag taatcaatta   1080
cggggtcatt agttcatagc ccatatatgg agttccgcgt tacataactt acggtaaatg   1140
gcccgcctgg ctgaccgccc aacgaccccc gcccattgac gtcaataatg acgtatgttc   1200
ccatagtaac gccaataggg actttccatt gacgtcaatg ggtggagtat ttacggtaaa   1260
```

```
ctgcccactt ggcagtacat caagtgtatc atatgccaag tacgccccct attgacgtca   1320
atgacggtaa atggcccgcc tggcattatg cccagtacat gaccttatgg gactttccta   1380
cttggcagta catctacgta ttagtcatcg ctattaccat ggtgatgcgg ttttggcagt   1440
acatcaatgg gcgtggatag cggtttgact cacggggatt ccaagtctc caccccattg    1500 acgtcaatgg gagtttgttt tggcaccaaa atcaacggga ctttccaaaa tgtcgtaaca   1560
actccgcccc attgacgcaa atgggcggta ggcgtgtacg gtgggaggtc tatataagca   1620
gagctggttt agtgaaccgt cagatccgct agcgctaccg gactcagatc cccccccccc   1680
cc                                                                  1682

<210> SEQ ID NO 79
<211> LENGTH: 1609
<212> TYPE: DNA
<213> ORGANISM: Artificial sequence
<220> FEATURE:
<223> OTHER INFORMATION: Combinded Seuence

<400> SEQUENCE: 79
gaggagctcc aggacaacaa ggccacagtg gtgtgtctcc tgaattcctt ctaccccggc     60
tctgtgaatg tcagctggaa ggcagatggc accaccatca accagggcgt gcagaccaca    120
cagcctgcca acagagcga caacaaatac atggccagca gctacctgac actgactccc     180
gaccagtgga ggtctcacca gagaatcagc tgccaggtca acacgaggc aggcaatgtg     240 gagaagagtt tggccccgtc agagtgttct tagcggccgc gactctagat cataatcagc    300
cataccacat ttgtagaggt tttacttgct ttaaaaaacc tcccacacct ccccctgaac    360
ctgaaacata aaatgaatgc aattgttgtt gttaacttgt ttattgcagc ttataatggt    420
tacaaataaa gcaatagcat cacaaatttc acaaataaag cattttttc actgcattct    480 agttgtggtt tgtccaaact catcaatgta tcttaaggcg taaattgtaa gcgttaatat    540
tttgttaaaa ttcgcgttaa attttgtta aatcagctca tttttaacc ataggccga     600 aatcggcaaa atcccttata atcaaaaga atagaccgag atagggttga gtgttgttcc    660
agtttggaac aagagtccac tattaaagaa cgtggactcc aacgtcaaag gcgaaaaac     720 cgtctatcag ggcgatggcc cactacgtga accatcaccc taatcaagtt ttttggggtc    780
gaggtgccgt aaagcactaa atcggaaccc taaagggagc cccgatttta gagcttgacg    840 ggaaagccg gcgaacgtgg cgagaaagga agggaagaaa gcgaaaggag cgggcgctag    900
ggcgctggca agtgtagcgg tcacgctgcg cgtaaccacc acaccgccg cgcttaatgc     960 gccgctacag ggcgcgtcag atcttagtta ttaatagtaa tcaattacgg ggtcattagt   1020
tcatagccca tatatggagt tccgcgttac ataacttacg gtaaatggcc cgcctggctg   1080
accgcccaac gacccccgcc cattgacgtc aataatgacg tatgttccca tagtaacgcc   1140
aatagggact ttccattgac gtcaatgggt ggagtattta cggtaaactg cccacttggc   1200
agtacatcaa gtgtatcata tgccaagtac gccccctatt gacgtcaatg acggtaaatg   1260
gcccgcctgg cattatgccc agtacatgac cttatgggac tttcctactt ggcagtacat   1320
ctacgtatta gtcatcgcta ttaccatggt gatgcggttt tggcagtaca tcaatgggcg   1380
tggatagcgg tttgactcac ggggatttcc aagtctccac cccattgacg tcaatgggag   1440
tttgttttgg caccaaaatc aacgggactt ccaaaatgt cgtaacaact ccgccccatt    1500
gacgcaaatg gcggtaggc gtgtacggtg ggaggtctat ataagcagag ctggtttagt   1560
gaaccgtcag atccgctagc gctaccggac tcagatcccc ccccccccc                1609
```

<210> SEQ ID NO 80
<211> LENGTH: 28
<212> TYPE: DNA
<213> ORGANISM: Artificial sequence
<220> FEATURE:
<223> OTHER INFORMATION: Primer

<400> SEQUENCE: 80
gctggctgct tgaggtcacg ctcaccac                                28

<210> SEQ ID NO 81
<211> LENGTH: 25
<212> TYPE: DNA
<213> ORGANISM: Artificial sequence
<220> FEATURE:
<223> OTHER INFORMATION: Primer

<400> SEQUENCE: 81
cagttgtttg ggtggtgcca tccac                                   25

<210> SEQ ID NO 82
<211> LENGTH: 27
<212> TYPE: DNA
<213> ORGANISM: Artificial sequence
<220> FEATURE:
<223> OTHER INFORMATION: Primer

<400> SEQUENCE: 82
ctgccggacg gacgggaagg tgcgtac                                 27

<210> SEQ ID NO 83
<211> LENGTH: 26
<212> TYPE: DNA
<213> ORGANISM: Artificial sequence
<220> FEATURE:
<223> OTHER INFORMATION: Primer

<400> SEQUENCE: 83
acacacgatg gtgactgttc cagttg                                  26

<210> SEQ ID NO 84
<211> LENGTH: 2230
<212> TYPE: DNA
<213> ORGANISM: Artificial sequence
<220> FEATURE:
<223> OTHER INFORMATION: Combined sequence

<400> SEQUENCE: 84
ctggtcaaag gctacctccc ggagccagtg accgtgacct ggaactcggg caccctcacc    60
aatggggtac gcaccttccc gtccgtccgg cagtcctcag gcctctactc gctgagcagc   120
gtggtgagcg tgacctcaag cagccagccc gtcacctgca acgtggccca cccagccacc   180
aacaccaaag tggacaagac cgttgcgccc tcgacatgca gcaagcccac gtgcccaccc   240
cctgaactcc tggggggacc gtctgtcttc atcttccccc caaaacccaa ggacaccctc   300
atgatctcac gcacccccga ggtcacatgc gtggtggtgg acgtgagcca ggatgacccc   360
gaggtgcagt tcacatggta cataaacaac gagcaggtgc gcaccgcccg gccgccgcta   420
cgggagcagc agttcaacag cacgatccgc gtggtcagca ccctcccat cgcgcaccag   480 gactggctga ggggcaagga gttcaagtgc aaagtccaca acaaggcact cccgccccc   540 atcgagaaaa ccatctccaa agccagaggg cagcccctgg agccgaaggt ctacaccatg   600

```
ggccctcccc gggaggagct gagcagcagg tcggtcagcc tgacctgcat gatcaacggc      660
ttctacccct tccgacatctc ggtggagtgg gagaagaacg ggaaggcaga ggacaactac      720
aagaccacgc cggccgtgct ggacagcgac ggctcctact tcctctacag caagctctca      780
gtgcccacga gtgagtggca gcggggcgac gtcttcacct gctccgtgat gcacgaggcc      840
ttgcacaacc actacacgca gaagtccatc tcccgctctc cgggtaaatg agcgcggccg      900
cgactctaga tcataatcag ccataccaca tttgtagagg ttttacttgc tttaaaaaac      960
ctcccacacc tcccctgaa cctgaaacat aaaatgaatg caattgttgt tgttaacttg      1020
tttattgcag cttataatgg ttacaaataa agcaatagca tcacaaattt cacaaataaa      1080 gcatttttt cactgcattc tagttgtggt ttgtccaaac tcatcaatgt atcttaaggc      1140
gtaaattgta agcgttaata ttttgttaaa attcgcgtta aattttttgtt aaatcagctc      1200 attttttaac caataggccg aaatcggcaa aatcccttat aaatcaaaag aatagaccga      1260
gatagggttg agtgttgttc cagtttggaa caagagtcca ctattaaaga acgtggactc      1320
caacgtcaaa gggcgaaaaa ccgtctatca gggcgatggc ccactacgtg aaccatcacc      1380
ctaatcaagt ttttggggt cgaggtgccg taaagcacta atcggaaacc ctaaagggag      1440
cccccgattt agagcttgac ggggaaagcc ggcgaacgtg gcgagaaagg aagggaagaa      1500
agcgaaagga gcgggcgcta gggcgctggc aagtgtagcg gtcacgctgc gcgtaaccac      1560
cacacccgcc gcgcttaatg cgccgctaca gggcgcgtca gatcttagtt attaatagta      1620
atcaattacg gggtcattag ttcatagccc atatatggag ttccgcgtta cataacttac      1680
ggtaaatggc ccgcctggct gaccgcccaa cgacccccgc ccattgacgt caataatgac      1740
gtatgttccc atagtaacgc caataggggac tttccattga cgtcaatggg tggagtattt      1800
acggtaaact gcccacttgg cagtacatca agtgtatcat atgccaagta cgccccctat      1860
tgacgtcaat gacggtaaat ggcccgcctg gcattatgcc cagtacatga ccttatggga      1920
ctttcctact tggcagtaca tctacgtatt agtcatcgct attaccatgg tgatgcggtt      1980
ttggcagtac atcaatgggc gtggatagcg gtttgactca cggggatttc caagtctcca      2040
ccccattgac gtcaatggga gtttgttttg gcaccaaaat caacgggact ttccaaaatg      2100
tcgtaacaac tccgccccat tgacgcaaat gggcggtagg cgtgtacggt gggaggtcta      2160
tataagcaga ctggtttag tgaaccgtca gatccgctag cgctaccgga ctcagatccc      2220
ccccccccc                                                             2230

<210> SEQ ID NO 85
<211> LENGTH: 1649
<212> TYPE: DNA
<213> ORGANISM: Artificial sequence
<220> FEATURE:
<223> OTHER INFORMATION: Combined sequence

<400> SEQUENCE: 85
atccagttgc acctactgtc ctcatcttcc caccagctgc tgatcaggtg gcaactggaa       60
cagtcaccat cgtgtgtgtg gcgaataaat actttcccga tgtcaccgtc acctgggagg      120
tggatggcac cacccaaaca actggcatcg agaacagtaa acaccgcag aattctgcag       180 attgtaccta caacctcagc agcactctga cactgaccag cacacagtac aacagccaca      240
aagagtacac ctgcaaggtg acccagggca cgacctcagt cgtccagagc ttcaacaggg      300
gtgactgcta gagcggccgc gactctagat cataatcagc cataccacat ttgtagaggt      360
tttacttgct ttaaaaaacc tcccacacct ccccctgaac ctgaaacata aaatgaatgc      420
```

```
aattgttgtt gttaacttgt ttattgcagc ttataatggt tacaaataaa gcaatagcat    480
cacaaatttc acaaataaag catttttttc actgcattct agttgtggtt tgtccaaact    540
catcaatgta tcttaaggcg taaattgtaa gcgttaatat tttgttaaaa ttcgcgttaa    600 attttttgtta aatcagctca tttttttaacc aataggccga aatcggcaaa atcccttata   660
aatcaaaaga atagaccgag atagggttga gtgttgttcc agtttggaac aagagtccac    720
tattaaagaa cgtggactcc aacgtcaaag ggcgaaaaac cgtctatcag ggcgatggcc    780
cactacgtga accatcaccc taatcaagtt ttttgggggtc gaggtgccgt aaagcactaa   840
atcggaaccc taaagggagc ccccgattta gagcttgacg gggaaagccg cgaacgtgg    900 cgagaaagga agggaagaaa gcgaaaggag cgggcgctag ggcgctggca agtgtagcgg    960
tcacgctgcg cgtaaccacc acacccgccg cgcttaatgc gccgctacag ggcgcgtcag    1020
atcttagtta ttaatagtaa tcaattacgg ggtcattagt tcatagccca tatatggagt    1080
tccgcgttac ataacttacg gtaaatggcc cgcctggctg accgcccaac gaccccgcc     1140 cattgacgtc aataatgacg tatgttccca tagtaacgcc aatagggact ttccattgac    1200
gtcaatgggt ggagtattta cggtaaactg cccacttggc agtacatcaa gtgtatcata    1260
tgccaagtac gccccctatt gacgtcaatg acggtaaatg gcccgcctgg cattatgccc    1320
agtacatgac cttatgggac tttcctactt ggcagtacat ctacgtatta gtcatcgcta    1380
ttaccatggt gatgcggttt tggcagtaca tcaatgggcg tggatagcgg tttgactcac    1440
ggggatttcc aagtctccac cccattgacg tcaatgggag tttgttttgg caccaaaatc    1500
aacgggactt tccaaaatgt cgtaacaact ccgccccatt gacgcaaatg ggcggtaggc    1560
gtgtacggtg ggaggtctat ataagcagag ctggtttagt gaaccgtcag atccgctagc    1620
gctaccggac tcagatcccc ccccccccc                                      1649
```

<210> SEQ ID NO 86
<211> LENGTH: 106
<212> TYPE: PRT
<213> ORGANISM: Guinea Pig

<400> SEQUENCE: 86

Gln Ile Val Leu Thr Gln Ser Pro Ala Ser Leu Ala Ala Ser Pro Gly
1               5                   10                  15

Glu Lys Val Thr Ile Thr Cys Thr Ala Ser Ser Ser Val Asn Asn Asn
            20                  25                  30

Phe Leu His Trp Tyr Gln Gln Lys Pro Gly Ala Ser Pro Lys Leu Val
        35                  40                  45

Ile Tyr Arg Thr Ser Lys Leu Ala Ser Gly Val Pro Ala Arg Phe Ser
    50                  55                  60

Gly Ser Gly Ser Gly Thr Ser Trp Ser Leu Thr Ile Ser Ser Met Glu
65                  70                  75                  80

Gly Glu Asp Val Ala Thr Tyr Tyr Cys Gln Gln Ser Arg Ser Tyr Thr
                85                  90                  95

Ser Ala Gln Asp Pro Asn Arg Lys Leu Ile
            100                 105

<210> SEQ ID NO 87
<211> LENGTH: 106
<212> TYPE: PRT
<213> ORGANISM: Guinea Pig

<400> SEQUENCE: 87

-continued

```
Asp Ile Gln Leu Thr Gln Pro Ala Ser Ala Ser Val Gly Asp
1               5                   10                  15

Thr Leu Lys Ile Ser Cys Arg Ala Ser Gln Ser Ile Lys Asn Tyr Leu
            20                  25                  30

Asn Trp Tyr Gln Gln Lys Pro Gly Gln Ala Pro Lys Leu Leu Ile Tyr
        35                  40                  45

Trp Ala Thr Asn Leu Gln Ser Gly Ile Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ser Thr Tyr Tyr Cys Gln Gln Ser Lys Thr Ser Pro Ser Leu
                85                  90                  95

Leu Ala Glu Asp Gln Ala Glu Phe Met Ala
            100                 105

<210> SEQ ID NO 88
<211> LENGTH: 113
<212> TYPE: PRT
<213> ORGANISM: Guinea Pig

<400> SEQUENCE: 88

Asp Thr Val Met Thr Gln Ser Pro Ala Ser Leu Ala Val Thr Pro Gly
1               5                   10                  15

Glu Arg Ala Thr Ile His Cys Lys Ser Ser Gln Ser Leu Leu Ser Ser
            20                  25                  30

Glu Asn Asn Lys Asn Tyr Leu Asp Trp Tyr Gln His Lys Pro Gly Gln
        35                  40                  45

Ser Pro Lys Leu Leu Ile Tyr Leu Ala Ser Thr Arg Ala Ile Gly Val
    50                  55                  60

Pro Asp Arg Phe Ser Gly Ser Gly Ser Gly Thr Asp Phe Ile Leu Thr
65                  70                  75                  80

Ile Ser Pro Val Gln Ala Glu Asp Val Ala Asp Tyr Phe Cys Met Gln
                85                  90                  95

Thr Phe Gly Thr Pro Gly Arg Ser Ala Leu Gly Gln Thr Gly Lys Lys
            100                 105                 110

Phe

<210> SEQ ID NO 89
<211> LENGTH: 114
<212> TYPE: PRT
<213> ORGANISM: Guinea Pig

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Leu Ser Gly Tyr
            20                  25                  30

Ser Val Ser Trp Ile Arg Gln Ala Pro Gly Lys Gly Leu Glu Trp Ile
        35                  40                  45

Gly Ala Ile Trp Ala Thr Gly Ser Thr Asp Tyr Asp Ser Ala Phe Lys
    50                  55                  60

Ser Arg Val Gly Ile Ser Arg Asp Ile Ser Lys Ser Glu Val Ser Leu
65                  70                  75                  80

Thr Leu Ser Ser Leu Ser Pro Glu Asp Ser Ala Val Tyr Tyr Cys Ala
                85                  90                  95
```

Arg Ala Gln Phe Phe Asp Val Trp Gly Thr Gly Val Leu Val Thr Val
            100                 105                 110

Ser Ser

<210> SEQ ID NO 90
<211> LENGTH: 128
<212> TYPE: PRT
<213> ORGANISM: Guinea Pig

<400> SEQUENCE: 90

Gln Leu Gln Leu Gln Gln Ser Gly Pro Gly Leu Val Lys Pro Ser Gln
1               5                   10                  15

Thr Leu Phe Leu Thr Cys Ser Val Ser Gly Phe Ser Ile Ala Thr Ser
            20                  25                  30

Gly Tyr Gly Trp Ser Trp Ile Arg Gln Ala Arg Gly Lys Thr Leu Glu
        35                  40                  45

Leu Met Gly Gly Ile Ala Tyr Asn Gly Thr Gly Tyr Asn Pro Ser
    50                  55                  60

Ile Lys Ser Arg Ile Ser Ile Ser Arg Asp Thr Val Lys Asn Gln Phe
65                  70                  75                  80

Ser Leu Gln Leu Asn Ser Val Thr Asp Glu Asp Ala Ala Thr Tyr Tyr
                85                  90                  95

Cys Ala Arg Gly Pro Leu Tyr Ser Ile Gly Val Trp Ser Asn Tyr
            100                 105                 110

Gly Tyr Phe Asp Phe Trp Gly Ser Gly Ile Leu Val Ser Val Ser Ser
            115                 120                 125

<210> SEQ ID NO 91
<211> LENGTH: 114
<212> TYPE: PRT
<213> ORGANISM: Guinea Pig

<400> SEQUENCE: 91

Glu Val Gln Leu Val Glu Ser Gly Gly Asp Leu Val Gln Pro Gly Gly
1               5                   10                  15

Ser Leu Arg Leu Ser Cys Leu Ala Ser Gly Phe Thr Phe Ser Arg Tyr
            20                  25                  30

Gly Met Ser Trp Ile Arg Arg Ala Pro Gly Lys Gly Leu Glu Trp Ile
        35                  40                  45

Ser His Ile Ser Asp Ser Gly Ser Asn Thr Tyr Tyr Pro Asp Ser Val
    50                  55                  60

Lys Gly Arg Phe Thr Ile Ser Arg Asp Asn Gly Lys Ser Leu Leu Tyr
65                  70                  75                  80

Leu Gln Met Ser Ser Leu Arg Pro Glu Asp Thr Ala Val Tyr Tyr Cys
                85                  90                  95

Gly Ser Val Gly Ser Leu Tyr Trp Gly Gln Gly Thr Leu Val Thr Val
            100                 105                 110

Ser Ser

METHOD FOR SELECTING PLASMA CELLS OR PLASMABLASTS, METHOD FOR PRODUCING TARGET ANTIGEN SPECIFIC ANTIBODIES, AND NOVEL MONOCLONAL ANTIBODIES

CROSS REFERENCE TO RELATED APPLICATIONS

This application claims benefit of priority to Japanese Patent Application No. 2011-075135 filed on Mar. 30, 2011, which is expressly incorporated herein by reference in its entirety.

TECHNICAL FIELD

The present invention relates to a method for selecting plasma cells or plasmablasts, a method for producing target antigen specific antibodies, and a novel monoclonal antibodies. More specifically, the present invention relates to a method for selecting plasma cells or plasmablasts that specifically bind to a target antigen, a method for producing target antigen specific antibodies using plasma cells or plasmablasts that have been obtained by this method, and to a novel monoclonal antibodies newly obtained by this method for producing antibodies.

BACKGROUND ART

Most of the monoclonal antibodies currently employed in the development of antibody pharmaceuticals are humanized mouse antibodies. That is because the mouse hybridoma method has been established as a method of producing monoclonal antibodies. However, many of the functional antigen epitopes of human proteins that are used as antibody drug markers have a high degree of homology with the amino acid sequences of both humans and mice. Even when mice are immunized to such antigens, it is difficult to obtain highly specific antibodies due to immune tolerance. Thus, it is necessary to fabricate a large number of hybridomas and screen them in order to obtain antibodies of high capability. Accordingly, there is a need to develop a means of efficiently producing monoclonal antibodies of high capability by inducing immunization in animal species having amino acid sequences that differ as much as possible from human antigens and avoiding the limits of immune tolerance to develop new antibody pharmaceuticals.

In the conventional fabrication of monoclonal antibodies, the method of fusing antibody-producing cells with myeloma cells to fabricate hybridomas having autonomous replication capability and screening those clones having the ability to produce antibodies that are specific to the target from among them has been widely employed. However, there are a number of drawbacks to the hybridoma method. For one, the hybridoma technique is limited to mouse antibody-producing cells, and is difficult to apply to other animal species. There is a further drawback in that time and effort are required to clone hybridomas. Moreover, there is a problem in that even when screening is conducted, there is no guarantee of obtaining clones having the ability to produce antigen specific antibodies.

To overcome these drawbacks, the method of identifying plasma cells (antigen specific plasma cells) having the ability to produce antigen specific antibodies by applying the ELISPOT method has been developed to fabricate human monoclonal antibodies (Japanese Examined Patent Publication (KOKOKU) No. 2009-34047: Patent Reference 1 (WO2009/017226, US2011/0294678A1 (which are hereby included in their entirety by reference)). It is a method by which plasma cells purified from human lymphocytes are introduced into microcells that have been specially processed, antibodies that are secreted in large quantities by the plasma cells are immobilized on the base surrounding the plasma cells, labeled antigen is reacted therewith, and antigen specific plasma cells are identified.

SUMMARY OF THE INVENTION

However, in the method described in Patent Reference 1, a special device is required to identify antigen specific plasma cells and an extremely onerous operation is needed to recover the cells. Further, since this method requires an operation of purifying plasma cells using cell surface antigen, it cannot fabricate antigen specific monoclonal antibodies from animal species for which a plasma cell identification method has not been established.

Accordingly, the object of the present invention is to provide a technique of efficiently fabricating antigen specific monoclonal antibodies from a wide range of animal species that overcomes the above drawbacks.

A further object of the present invention is to provide a novel antigen specific monoclonal antibody using the above newly developed technique of fabricating antigen specific monoclonal antibodies.

B cells express antibodies on the cellular membrane (membrane-bound antibodies). When antigens bind thereto, immunoglobulin gene class switching and high-frequency somatic mutation occur. As a result, B cells with increased antigen affinity are selected. Some of these high-affinity B cells differentiate into plasma cells, becoming antibody-producing cells. With this differentiation, the plasma cells are known to cease expressing membrane-bound antibodies by the selective splicing of immunoglobulin genes and to express large amounts of secretory antibodies (Immunological Reviews, Sarah A. Oracki, Jennifer A. Walker, Margaret L. Hibbs, Lynn M. Corcoran, David M. Tarlinton, Special Issue: B-Lymphocyte Biology, Volume 237, Issue 1, pages 140-159, September 2010: Nonpatent reference 2, which is expressly incorporated herein by reference in its entirety.

The present inventors, in the process of analyzing the plasma cells of rats, guinea pigs, and rabbits, discovered for the first time ever that quantities of membrane-bound antibody molecules capable of being analyzed by antigen binding were expressed on the surface of plasma cells obtained from these animals. Thus, it was thought possible to identify antigen specific plasma cells by causing labeled antigen to directly bind to the high-affinity membrane-bound antibodies expressed on the surface of plasma cells. However, the quantity of antibody molecules expressed on the membranes of plasma cells was small. Thus, even when plasma cells to which labeled antigen had been specifically bound were present, noise due to nonspecific adsorption of labeled antigen made it difficult to identify antigen specific plasma cells.

The present inventors discovered a "fluorescent probe for identifying and isolating plasma cells and a method for identifying and isolating plasma cells using this probe" as a method of efficiently identifying plasma cells using endoplasmic reticulum-specific fluorescent dyes, and submitted a patent application (WO2011/118579 (which is hereby incorporated in its entirety by reference)).

The present inventors discovered that it was possible to identify antigen specific plasma cells by means of a simple operation of subjecting a cell suspension solution prepared from an immune animal to the action of a fluorescent-labeled antigen and a fluorescent dye with endoplasmic reticulum affinity. The present invention was devised on that basis.

The present invention is as set forth below.

[1]
A method for selecting a plasma cell(s) and/or plasmablast(s) that specifically bind to a target antigen, comprising:
either collecting lymph fluid, lymphoid tissue, blood cell sample, or bone marrow derived cells from a nonhuman animal, and sensitizing the lymphocytes, lymphoid tissue, blood cell sample, or bone marrow derived cells in vitro to the target antigen, or
immunizing a nonhuman animal to the target antigen, and collecting lymph fluid, lymphoid tissue, blood cell sample, or bone marrow derived cells from the nonhuman animal once immunization has been established;
mixing the sensitized or collected lymph fluid, lymphoid tissue, blood cell sample, or bone marrow derived cells with (1) a labeled target antigen and (2) a marker that selectively binds to plasma cells and/or plasmablasts; and
selecting a cell(s) to which (1) the labeled target antigen and (2) the marker have bound.

[2]
A method for selecting a human plasma cell(s) and/or plasmablast(s) that specifically bind to a target antigen, comprising:
either collecting lymph fluid, lymphoid tissue, blood cell sample, or bone marrow derived cells from a human, and sensitizing the lymphocytes, lymphoid tissue, blood cell sample, or bone marrow derived cells in vitro to the target antigen, or
collecting lymph fluid, lymphoid tissue, blood cell sample, or bone marrow derived cells from a human having antibodies to the target antigen;
mixing the sensitized or collected lymph fluid, lymphoid tissue, blood cell sample, or bone marrow derived cells with (1) a labeled target antigen and (2) a marker that selectively binds to plasma cells and/or plasmablasts; and
selecting a cell(s) to which (1) the labeled target antigen and (2) the marker have bound.

[3]
A method for producing a target antigen specific antibody or antibody fragment, comprising:
selecting a plasma cell(s) and/or plasmablast(s) that specifically bind to a target antigen by the method according to claim 1 or 2;
collecting a gene of an antibody against the target antigen from the selected cell(s), and identifying the base sequence of the gene; and
preparing the antibody or antibody fragment based on the identified base sequence of the gene.

[4]
The method according to any one of claims 1 to 3,
wherein the marker that selectively binds to plasma cells and/or plasmablasts is a fluorescent probe for identifying or isolating plasma cells and/or plasmablasts, wherein the staining selectivity for an endoplasmic reticulum in cells is higher than the staining selectivity for cell organelles other than an endoplasmic reticulum, and with the staining of the fluorescent probe, plasma cells and plasmablasts are distinguishable from cells other than plasma cells and plasmablasts.

[5]
The method according to claim 4, wherein the fluorescent probe is selected from the group consisting of (1) a substance which is amphiphilic and cationic and have moderate lipophilicity and (2) a substance which has affinity to a protein localized in an endoplasmic reticulum above a certain degree.

[6]
The method according to claim 5, wherein the amphiphilicity is defined by the amphiphilicity index (AI) as +6>AI>0, the moderate lipophilicity is defined by the hydrophobic index (log P) as +6>log P>0, and the affinity above a certain degree is defined by the dissociation constant of the range of 0.1 µM to 0.1 nM.

[7]
The method according to any one of claims 4 to 6, wherein the cell organelle other than an endoplasmic reticulum is plasma-membrane, mitochondria, Golgi body, lysosome, peroxisome, nucleus, centrosome, cytoplasm, phagosome, endosome, or aggresome.

[8]
The method according to any one of claims 4 to 7, wherein the fluorescent probe is selected from the group consisting of fluorescent labeled glibenclamide, fluorescent labeled Brefeldin A, fluorescent probe, and fluorescent protein.

[9]
A gene of the γ chain constant region of the guinea pig antibody to human insulin, which is indicated by SEQ ID NO: 1 of the SEQUENCE LISTING, or
a gene coding for a peptide in the γ chain constant region of a guinea pig antibody to human insulin, which has the amino acid sequence indicated by SEQ ID NO: 4 in the SEQUENCE LISTING.

[10]
A gene of the κ chain constant region of a guinea pig antibody to human insulin, which is indicated by SEQ ID NO: 2 in the SEQUENCE LISTING, or
a gene coding for a peptide of the κ chain constant region of a guinea pig antibody to human insulin, which has the amino acid sequence indicated by SEQ ID NO: 5 in the SEQUENCE LISTING.

[11]
A gene of the λ chain constant region of a guinea pig antibody to human insulin, which is indicated by SEQ ID NO: 3 in the SEQUENCE LISTING, or
a gene coding for a peptide of the λ chain constant region of a guinea pig antibody to human insulin, which has the amino acid sequence indicated by SEQ ID NO: 6 in the SEQUENCE LISTING.

[12]
A peptide of the γ chain constant region of a guinea pig antibody to human insulin, which has the amino acid sequence indicated by SEQ ID NO: 4 in the SEQUENCE LISTING.

[13]
A peptide of the κ chain constant region of a guinea pig antibody to human insulin, which has the amino acid sequence indicated by SEQ ID NO: 5 in the SEQUENCE LISTING.

[14]
A peptide of the λ chain constant region of a guinea pig antibody to human insulin, which has the amino acid sequence indicated by SEQ ID NO: 6 in the SEQUENCE LISTING.

[15]
A gene of the γ chain variable region of a guinea pig antibody to human insulin, which is indicated by any one of SEQ ID NOs: 7 to 18 in the SEQUENCE LISTING, or a gene coding for a peptide of the γ chain variable region of a guinea pig antibody to human insulin, which has the amino acid sequence indicated by any one of SEQ ID NOs: 19 to 30 and 89 to 91.

[16]
A gene of the κ chain variable region of a guinea pig antibody to human insulin, which is indicated by any one of SEQ ID NOs: 31 to 42 of the SEQUENCE LISTING, or
a gene coding for a peptide of the κ chain variable region of a guinea pig antibody to human insulin, which has the amino acid sequence indicated by any one of SEQ ID NOs: 43 to 54 and 86 to 88.

[17]
A peptide of the γ chain variable region of a guinea pig antibody to human insulin, which has the amino acid sequence indicated by any one of SEQ ID NOs: 19 to 30 and 89 to 91.

[18]
A peptide of the κ chain variable region of a guinea pig antibody to human insulin, which has the amino acid sequence indicated by any one of SEQ ID NOs: 43 to 54 and 86 to 881.

[19]
A guinea pig monoclonal antibody to human insulin, which has a γ chain having
the amino acid sequence indicated by any one of SEQ ID NOs: 19 to 30 and 89 to 91 as a variable region and
the amino acid sequence indicated by SEQ ID NO: 4 as a constant region.

[20]
A guinea pig monoclonal antibody to human insulin, which has a κ chain having
the amino acid sequence indicated by any one of SEQ ID NOs: 43 to 54 and 86 to 88 as a variable region and
the amino acid sequence indicated by SEQ ID NO: 5 as a constant region.

[21]
A guinea pig monoclonal antibody to human insulin, which comprises
a κ chain containing a combination of a κ chain CDR1, a κ chain CDR2, and a κ chain CDR3 selected from each below, or
a γ chain containing a combination of a γ chain CDR1, a γ chain CDR2, and a γ chain CDR3 selected from each below:

| κ chain CDR1 | κ chain CDR2 | κ chain CDR3 |
|---|---|---|
| QTINNY | GTN | QQSRSSPFT |
| QTISSY | GTN | QQSNSSPFT |
| QSVSSY | WAT | QQSKTSPFT |
| QTISSY | GTN | QQSRSSPFT |
| SSVNNNF | RTS | LQSNSYT |
| QSLLSRYNNKNN | WAS | MQYYHPRT |
| SSISESY | WAS | QQSTSYRT |
| SSLINNY | RTS | QESSSYYGT |
| SSISDSY | RTS | QQSTTYRT |
| STLIKNY | RTS | QESTSYYGT |
| SNLINNY | RTS | QESTSYYGT |
| SSLINNY | RTS | QEYTSYYGT |
| SSVNNNF | RTS | QQSRSYT |
| QSIKNY | WAT | QQSKTSPSL |
| QSLLSSENNKNY | LAS | MQTFGTPGR |

| γ chain CDR1 | γ chain CDR2 | γ chain CDR3 |
|---|---|---|
| GFSITTSGYA | IAYNGGT | ARGPLYSVGRAWSNYWYFDF |
| GFSITTSGYG | IAYNGGT | ARGPLYYVGRAWSNYWYFDF |
| GFSITTSGYG | IAYNGGT | ASGPLYRIGAVWSNYRSFDF |
| GFSITTSGYA | IAYNGGT | ARGPLYYVGRAWSNYWYFDF |
| GFSLMDYS | IWSSGST | ARAQYFDV |
| EFSITTSGYG | IAYNGAT | ARSGSHSSGVYYIP-SYFDV |
| GMTLSNYA | IVHSGSNT | ATDMGWNSALDV |
| GFSLTGYP | IWSFGST | ARHGSGYFDI |
| GLTLSNYA | ISHSGSRT | ATDMGWNSALDI |
| GFSLSGYP | IWPFGGT | ASHGNGYDI |
| GFSLTGYS | IWSFGST | ARHGGGYFDI |
| GFSLTGYS | IWNFGGT | TRHGSGYFDM |
| GFSLSGYS | IWATGST | ARAQFFDV |
| GFSIATSGYG | IAYNGGT | ARGPLYSIGGVWSNYGYFDF |
| GFTFSRYG | ISDSGSNT | GSVGSLY |

Effect of the Invention

Use of the present invention permits the rapid production of antigen specific monoclonal antibodies from a wide range of animals, thereby creating new possibilities for developing antibody pharmaceuticals for target molecules that are difficult to fabricate with existing techniques.

BRIEF DESCRIPTION OF THE DRAWINGS

FIG. 1 Shows the results of Example 1. Iliac lymph node-derived rat lymphocytes were subjected to cell surface antibody and endoplasmic reticulum staining using anti-rat IgG antibody (green, figure on left) and ER-tracker, observed by fluorescence microscopy, and photographed. The expression of IgG was observed on the surface of strongly ER-tracker positive plasma cells (arrows).

FIG. 2 Shows the results of Example 1. Results obtained by staining Iliac lymph-node derived rat lymphocytes with labeled GFP and ER-tracker and employing a cell sorter to conduct separation are given.
A is a two-dimensional analysis diagram of iliac lymph node derived rat lymphocytes by the fluorescence intensity of GFP (y axis) and ER tracker (x axis). The GFP positive, ER-tracker positive region (high) is indicated as the antigen specific plasma cell fraction, and the GFP negative, ER-tracker positive region (low) is indicated as the nonspecific plasma cell fraction. B shows a fluorescence microscopy photograph in which cells separated from the antigen specific plasma cell fraction were immobilized and then subjected to membrane solubilization. They were then subjected to the action of FITC labeled anti-rat IgG antibodies, the intracellular IgG was stained, and a photograph was taken by fluorescence microscopy. The cells that were separated expressed intracellular immunoglobulin, which is characteristic of plasma cells.

FIG. 5 Shows the results of Example 2. Iliac lymph node-derived guinea pig lymphocytes were subjected to cell surface antibody and endoplasmic reticulum staining using anti-guinea pig IgG antibody (green, figure on left) and ER-tracker, observed by fluorescence microscopy, and photographed. The expression of IgG was observed on the surface of strongly ER-tracker positive plasma cells (arrows).

FIG. 6 Shows the results of Example 2. A is a two-dimensional analysis diagram of guinea pig lymphocytes by fluorescence intensity when cells collected from guinea pig iliac lymph nodes were stained with fluorescence-labeled human insulin (y axis) and ER tracker (x axis) and separated with a cell sorter. The cells in the region denoted by R1 were considered to be the antigen specific plasma cell fraction and subjected to signal cell sorting. In B, cells obtained from antigen specific plasma cell fraction were immobilized, subjected to a membrane solubilization treatment, and subjected to the action of FITC-labeled anti-guinea pig IgG antibody. The intracellular IgG was stained (green). The endoplasmic reticulum was stained (red) with endoplasmic reticulum affinity fluorescence dye ER-ID. The cell nucleus was stained (blue) with Hechst 33342. The separated cells had characterizes plasma cells, i.e. the intracellular immunoglobulin (green), the developed endoplasmic reticulum (red), and the nuclei that were skewed to one side of the cells.

FIG. 11 Shows the results of Example 3. These are the results of conducting an amplification reaction of the variable region of the rabbit immunoglobulin κ chain gene using primer (d) and primer (x).

FIG. 12 Shows the results of Example 3. These are the results of changing the expression units of κ and γ chain immunoglobulin gene fragments and conducting agarose gel electrophoresis.

FIG. 13 Shows the results of Example 3. These are the results of checking by the ELISA method the antigen-binding ability of recombinant rabbit monoclonal antibodies obtained from antigen specific plasma cells and nonspecific plasma cells.

MODES OF CARRYING OUT THE INVENTION

Figure 3:
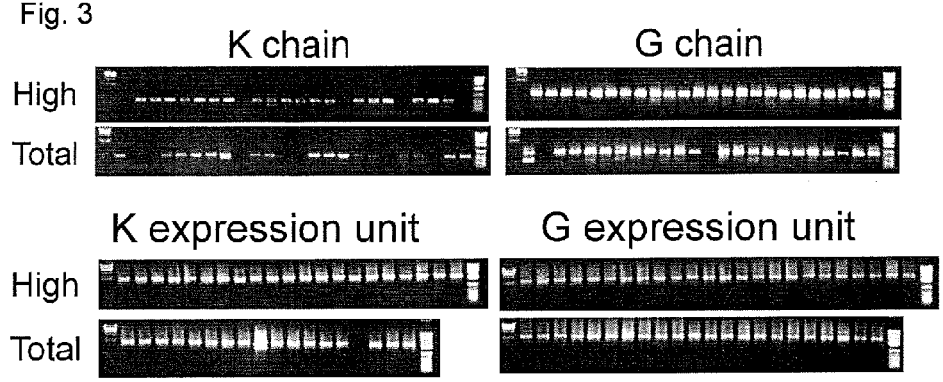
FIG. 3 Shows the results of Example 1. cDNA from cells separated with a cell sorter was synthesized. Using this as a template, the 5'-RACE PCR method was employed to amplify rat γ chain and κ chain variable region genes (K chain and G chain in the upper portion of the figure). The amplified variable regions were incorporated into a linearized expression vector and rat γ chain and κ chain immunoglobulin expression units were fabricated. The results of agarose electrophoresis of the amplified DNA are given (K expression unit and G expression unit in the lower portion of the figure).

Method of Selecting Plasma Cells and/or Plasmablasts that Specifically Bind to Target Antigen The first aspect of the present invention is a method for selecting plasma cells and/or plasmablasts that specifically bind to a target antigen.

The first aspect of the present invention is divided into two methods: a method employed on nonhuman animals (referred to as the "NHA" method hereinafter) and a method employed on humans (referred to as the "HU" method hereinafter). The NHA method, which is employed on nonhuman animals, comprises: either collecting lymph fluid, lymphoid tissue, blood cell sample, or bone marrow derived cells from a nonhuman animal, and sensitizing the lymphocytes, lymphoid tissue, blood cell sample, or bone marrow derived cells in vitro to a target antigen, or, immunizing the nonhuman animal to the target antigen; collecting lymph fluid, lymphoid tissue, a blood cell sample, or bone marrow derived cells from the animal once immunization has occurred;

mixing the sensitized or collected lymph fluid, lymphoid tissue, blood cell sample, or bone marrow derived cells with (1) a labeled target antigen and (2) a marker that selectively binds to the plasma cells and/or plasmablasts; and selecting those cells to which (1) the labeled target antigen and (2) the marker have bound.

The NHA method makes it possible to select at least one of the plasma cells or plasmablasts that specifically bind to a target antigen.

The HU method, which is employed on humans, comprises: collecting lymph fluid, lymphoid tissue, blood cell sample, or bone marrow derived cells from a human and either sensitizing the lymphocytes, lymphoid tissue, blood cell sample, or bone marrow derived cells in vitro to a target antigen or collecting lymph fluid, lymphoid tissue, a blood cell sample, or bone marrow derived cells from a human having antibodies to the target antigen;

mixing the sensitized or collected lymph fluid, lymphoid tissue, blood cell sample, or bone marrow derived cells with (1) a labeled target antigen and (2) a marker that selectively binds to the plasma cells and/or plasmablasts; and selecting those cells to which (1) the labeled target antigen and (2) the marker have bound.

The HU method makes it possible to select at least one of the plasma cells or plasmablasts that specifically bind to a target antigen.

The NHA method will be described below.

<Immunization of a Nonhuman Animal to a Target Antigen>

A nonhuman animal is immunized to a target antigen.

In the present invention, the term "nonhuman animal" means all animals having immune systems other than humans. Examples of such animals are mammals and birds. Examples of mammals are apes, monkeys, dogs, cats, horses, cows, pigs, sheep, goats, donkeys, camels, llamas, alpacas, reindeer, buffalos, yaks, guinea pigs, rabbits, mink, mice, rats, gerbils, hamsters, golden hamsters, Armenian hamsters, ferrets, miniature pigs, raccoons, opossums, Asian house shrews, kangaroos, and dolphins. Examples of birds are chickens, quail, and ostriches.

In the present invention, the term "target antigen" means a microorganism such as a virus, mycoplasma, bacterium, fungus, or the like; Lophotrochozoa such as shellfish; molting animals such as insects and crustaceans; Deuterostomia such as vertebrates; and the constituent substances, proteins, sugars, lipids, complex carbohydrates, nucleic acids, natural low-molecular-weight organic compounds, natural high-molecular-weight organic compounds, artificial low-molecular-weight organic compounds, artificial high-molecular-weight organic compounds, metal complexes, and the like thereof. However, there is no intent to limit the type of target antigen, and the above are but examples thereof.

The target antigen that is used to immunize a nonhuman animal can be employed as is. However, it is also possible to employ it in a dead state, in the form of an extract, or bonded or combined with a suitable support.

Lymph fluid, lymphoid tissue, a blood cell sample, or bone marrow-derived cells are collected from a nonhuman animal and the lymph fluid, lymphoid tissue, blood cell sample, or bone marrow-derived cells are sensitized in vitro to a target antigen. Sensitization to a target antigen in vitro can be conducted as follows for lymph fluid and the like. Antigen-presenting cells in the form of dendritic cells, T cells, or B cells are collected from a nonhuman animal. Next, the antigen is subjected to the action of the dendritic cells in a test tube so that it is phagocytosed or digested, thereby fabricating a mature dendritic cell with the ability to present the antigen. To this are added T cells, B cells, cytokines such as interleukin-2, and immunostimulants such as poly(dI-dC). Those B cells that respond to the antigen are caused to propagate and differentiate in the test tube, ultimately yielding antibody-producing cells in the form of plasma cells and plasmablasts.

In the present invention, the term "immunize a nonhuman animal to a target antigen" means to bring a nonhuman animal into contact with the target antigen and cause the expression of immunity to the target antigen in the nonhuman animal. The method of expression of the immunity to the target antigen is not specifically limited. For example, the target antigen can be administered to or inoculated into the nonhuman animal to immunize the nonhuman animal. The method of administering or inoculating the target antigen is not specifically limited. Examples of administration methods are administration by inhalation, oral administration, subcutaneous injection, intravenous injection, intramuscular injection, and methods of inducing the expression of the antigen within the body of the animal by the introduction of a gene into a nonhuman animal. Alternatively, the target antigen can be contacted with the skin of a nonhuman animal to immunize the animal.

The nonhuman animal is immunized with the target antigen until immunity to the target antigen is established in the nonhuman animal. Accordingly, the nonhuman animal is brought into contact with the target antigen until immunity to the target antigen is established. The frequency, duration, and quantity of target antigen employed per contact of the nonhuman animal with the target antigen can be suitably determined in accordance with the ease of establishing immunity. The usual methods, such as collecting blood from the nonhuman animal and obtaining confirmation by measuring the antibodies contained in the serum by the ELISA method, can be used to determine whether or not immunity to the target antigen has been established. The object of the present invention is to select the plasma cells and/or plasmablasts of a nonhuman animal that have bound nonspecifically to a target antigen. Thus, lymph fluid, lymphoid tissue, a blood sample, or bone marrow-derived cells are collected that have a high probability of containing plasma cells and/or plasmablasts.

<Collection of Lymph Nodes and the Like from Animals Once Immunization has been Established>

Lymph fluid, lymphoid tissue, a blood cell sample, or bone marrow-derived cells are collected from the animal once immunity has been established. The object of the present invention is to select plasma cells and/or plasmablasts of nonhuman animals that specifically bind a target antigen. Thus, lymph fluid, lymphoid tissue, a blood cell sample, or bone marrow-derived cells that stand a good chance of containing plasma cells and/or plasmablasts are collected.

Plasma cells and plasmablasts are what B lymphocytes ultimately differentiate into, and are thus cells that specialize in antibody production. Since somatic cell mutation of antibody genes, known as affinity maturation, and antigen-based selection have already occurred, these cells are particularly useful for isolating antibodies of high binding ability. However, plasma cells and plasmablasts are nonuniform cell groups comprised of a number of subtypes. Since their abundance in lymphoid tissue is a low 0.1% or less, high purity isolation is difficult. Identifying and isolating plasma cells and plasmablasts in peripheral blood and lymph nodes by the conventional methods requires a positive/negative screening operation comprising several steps in which antibodies for at least three types of cell surface marker are combined (Sanderson, R. D., Lalor, P., Bernfield, M. B lymphocytes express and lose syndecan at specific stages of differentiation: Cell Regulation 1: 27-35 (1989): Nonpatent reference 1, which is expressly incorporated herein by reference in its entirety.).

Lymph fluid, lymphoid tissue, blood cell samples, and bone marrow can be prepared by the following methods, for example. An antigen is injected subcutaneously, into muscle, or into the pad of the foot. When a month or more has elapsed, the swollen lymph fluid or lymphoid tissue is surgically removed from the nonhuman animal. Once the tissue accompanying the lymph nodes has been removed under a stereomicroscope, a pincette is employed to rupture the membrane of the lymph node, causing the cells within the lymph node to disperse into PBS solution (10 mM phosphate buffer, 120 mM NaCl, 2.7 mM KCl, pH 7.6). For a blood cell sample, mononuclear cells that have been separated by the density gradient centrifugation method from blood obtained by heparin blood collection from an immunized animal are employed. For bone marrow, the two ends of a femur removed from an immunized animal are cut off, PBS solution is injected into the marrow through a syringe inserted into one end of the bone, and the bone marrow cells that flow out from the other end are employed.

<Selection of Cells>

At least either the plasma cells or the plasmablasts of a nonhuman animal that have specifically bound to the target antigen are selected from the lymph nodes that are collected. To make this selection, (1) a labeled target antigen and (2) a marker that selectively binds to plasma cells and/or plasmablasts are employed.

(1) Labeled Target Antigen

The labeled target antigen is a substance containing the same epitope as the target antigen employed to immunize the nonhuman animal. Accordingly, it can be a substance that is precisely identical to the labeled target antigen and target antigen employed in immunization, or some other substance containing a shared epitope.

The substance that is employed to label the target antigen is not specifically limited. A label permitting the selection of plasma cells and/or plasmablasts to which the labeled target antigen has bound will suffice. Examples are fluorescent labels and magnetic bead labels. The type of fluorescent label is not specifically limited. It suffices for the marker that selectively binds to the plasma cells and/or plasmablasts to be distinguishable as a label so as to permit the differentiation of cells that have bound to the target antigen and the marker that selectively binds to plasma cells and/or plasmablasts from cells that have bound only the target antigen and cells that have bound only the marker that selective binds to plasma cells and/or plasmablasts.

(2) Marker that Selectively Binds to Plasma Cells and/or Plasmablasts

An example of a marker that selectively binds to plasma cells and/or plasmablasts is fluorescent probe 1 described below.

<Fluorescent Probe 1>

Fluorescent probe 1 is a fluorescent probe that is used to identify or separate plasma cells and plasmablasts. It has higher affinity for the endoplasmic reticulum of a cell than for other organelles. In other words, it is a fluorescent probe that selectively stains the endoplasmic reticulum of a cell. Plasma and plasmablasts have more highly developed endoplasmic reticulum than cells other than plasma cells and plasmablasts. As a result, the fluorescent intensity achieved by staining with fluorescent probe 1 exhibits a difference of recognizable degree between plasma cells and plasmablasts on the one hand and cells other than plasma cells and plasmablasts on the other. The ratio of fluorescent intensity that is exhibited by fluorescent probe 1 (the fluorescent intensity of plasma cells and plasmablasts/fluorescent intensity of cells other than plasma cells and plasmablasts) is, for example, three-fold or greater.

Although there is not a major difference in the affinity of fluorescent probe 1 for the endoplasmic reticulum of a plasma cell or a plasmablast and its affinity for the endoplasmic reticulum of a cell other than a plasma cell or plasmablast, a difference in fluorescence intensity is produced by the degree of development of the endoplasmic reticulum. As a result, based on the above fluorescence intensity ratio, it is possible to distinguish between plasma cells and plasmablasts on the one hand and cells other than plasma cells and plasmablasts on the other by staining with fluorescent probe 1.

By staining with fluorescent probe 1, it is possible to distinguish between plasma cells and plasmablasts that are present together with cells other than plasma cells and plasmablasts from cells other than plasma cells and plasmablasts by means of the difference in the fluorescence intensity of cells other than plasma cells and plasmablasts and the fluorescence intensity of plasma cells and plasmablasts. Thus, by staining with fluorescent probe 1, it is possible to readily identify plasma cells and plasmablasts among a group of cells in which cells other than plasma cells and plasmablasts are also present. Thus, by collecting the plasma cells and plasmablasts that have been identified, it is possible to obtain a cell group containing many plasma cells and plasmablasts.

Fluorescent probe 1 makes it possible to differentiate between the two when the fluorescence intensity of stained plasma cells and plasmablasts on the one hand is three-fold or more the fluorescence intensity of stained cells other than plasma cells and plasmablasts. From the perspective of facilitating differentiation, it is desirably four-fold or more, preferably five-fold or more. However, due to differences in the degree of development of the endoplasmic reticulum by types of cells other than plasma cells and plasmablasts, the fluorescence intensity ratio will vary with the type of cell other than a plasma cell or plasmablast. The greater the fluorescence intensity ratio, the more efficiently it will be possible to identify plasma cells and plasmablasts from among a cell group containing cells other than plasma cells and plasmablasts. Examples of cells other than plasma cells and plasmablasts are erythrocytes, platelets, T lymphocytes, B lymphocytes, granulocytes, macrophages, eosinophils, and basophils.

In the present invention, it is possible to distinguish between plasma cells and plasmablasts on the one hand and cells other than plasma cells and plasmablasts on the other using fluorescent probe 1 in the following manner. Fluorescent probe 1 is added to a cell suspension and staining is conducted for 30 minutes at 37° C. The concentration of fluorescent probe 1 that is suitable for staining will vary with the type of fluorescent probe 1. By way of example, it can be 100 nm to 1 μM. After staining, the cells are washed with PBS. Whether the washed cells are plasma cells and plasmablasts on the one hand or cells other than plasma cells and plasmablasts on the other hand can be determined by, for example, (1) employing a fluorescence microscope to observe the localization of the fluorescent probe in the cells or (2) based on the intensity of the fluorescence emitted by the cells. The method of differentiating between plasma cells and plasmablasts on the one hand and cells other than plasma cells and plasmablasts on the other will be described in detail in the plasma cell and plasmablast identification and separation method.

It is also possible to screen for substances that can be employed as fluorescent probe 1 among substances of unknown dye selectivity for the endoplasmic reticulum of plasma cells and plasmablasts and the endoplasmic reticulum of cells other than plasma cells and plasmablasts by applying the method of differentiating between plasma cells and plasmablasts on the one hand and cells other than plasma cells and plasmablasts on the other that is set forth above. Screening for fluorescent probes of high dye selectivity for the endoplasmic reticulum of cells that are suitable as fluorescent probe 1 in the present invention can be accomplished using methods of obtaining the ratio (B/A) of fluorescence intensity B of the endoplasmic reticulum to the fluorescence intensity A of the entire cell by using the method of identifying the endoplasmic reticulum of a cell, as set forth further below, by immunostaining a protein that is localized in the endoplasmic reticulum (immunoglobulin in a plasma cells and plasmablasts) or inducing the expression of a recombinant fluorescent protein with transferability to the endoplasmic reticulum in cultured cells.

The method of screening for substances that can be used as fluorescent probe 1, it is possible to employ just plasma cells and plasmablasts, or to employ just cells other than plasma cells and plasmablasts. However, plasma cells and plasmablasts have developed endoplasmic reticulum and yield relatively high fluorescence intensities by staining. Thus, the use of plasma cells and plasmablasts facilitates the evaluation of the dye selectivity of substances on the endoplasmic reticulum of cells. However, it is not easy to obtain plasma cells and plasmablasts. Thus, it is also possible to use cells other than plasma cells and plasmablasts to evaluate the staining property (staining strength) of endoplasmic reticulum and screen for substances that can be employed as fluorescent probe 1. For example, in staining tests employing common cultured cells (such as Hela cells), it is possible to screen for substances that can be used as fluorescent probe 1 by obtaining the ratio (B/A) of the fluorescence intensity B of endoplasmic reticulum to the fluorescence intensity A of the entire cell. However, when employing cells other than plasma cells and plasmablasts as the cells, the value of B/A serving as threshold is suitably set to a low value of about 50%, for example, of the value of B/A that is employed as a threshold in the screening method employing plasma cells and plasmablasts based on the degree of development of the endoplasmic reticulum in the cells.

Examples of cells other than plasma cells and plasmablasts are erythrocytes, platelets, T lymphocytes, B lymphocytes, granulocytes, macrophages, neutrophils, eosinophils, and basophils. In screening by the method set forth above, instead of plasma cells and plasmablasts, it is possible to employ hybridoma cells, plasma cell and plasmablast tumor cells, and multiple myeloma cells. That is because hybridoma cells, plasma cell and plasmablast tumor cells, and multiple myeloma cells also produce immunoglobulin, develop an endoplasmic reticulum, yield a high fluorescence intensity in staining, and afford relatively easy analysis of the dye selectivity of substances on the endoplasmic reticulum of cells.

Examples of substances that can serve as fluorescent probe 1, with high dye selectivity on the endoplasmic reticulum of plasma cells and plasmablasts and cells other than plasma cells and plasmablasts, are (1) amphiphilic, cationic substances with a moderate lipophilicity and (2) substances that have affinity to a protein localized in an endoplasmic reticulum above a certain degree. Substances with properties (1) and (2) have both better staining properties for the endoplasmic reticulum of plasma cells and plasmablasts and better staining properties for the endoplasmic reticulum of cells other than plasma cells and plasmablasts than for other cell organelles.

The phrase "amphiphilic and cationic" in (1) above means specifically that the amphiphilic index (AI) is, for example, +6>AI>0. The amphiphilic index is a value that is obtained by calculating the apparent log P value for the lipophilicity domain of the molecule. Specifically, based on the fragment value of Hansch et al., the length of the carbon chain, its positional relation, and the cationic polar effect of the quaternary ammonium group are taken into account, and the value is calculated according to the model of Morrall et al. [Hansch C, Leo A J. *Exploring QSAR: Fundamentals and Applications in Chemistry and Biology*, p. 160, American Chemical Society: Washington, D.C., 1995., Morrall S W, Herzog R R, Kloepper-Sams P, Rosen M J. Octanol/water partitioning of surfactants and its relevance to toxicity and environmental behavior. *Proc 4th World Surfactants Congress*, vol. 3. AEPSAT: Barcelona, 1996; 220-227.

The phrase "moderate lipophilicity" in (1) above means that the hydrophobic index (log P) is, for example, +6>log P>0. The hydrophobic index is a hydrophobic value of the entire molecule as calculated by the fragment estimation method of Hansch et al. Specifically, the accompanying structural effect is added to the hydrophobic group denoted by AI.

The phrase "having affinity to a protein localized in an endoplasmic reticulum above a certain degree" means specifically having an affinity with a dissociation constant of 0.1 μm to 0.1 nM. Substances that have affinity to a protein localized in an endoplasmic reticulum above a certain degree are also fluorescent probes that selectively stain the endoplasmic reticulum of a cell.

The compounds denoted by A, B, and C below are examples of substances that are (1) amphiphilic and cationic, with a moderate lipophilicity.

The compound denoted by formula A is DiOC6(3) (3,3'-dihexyloxacarbocyanine iodide). At low concentration, it accumulates in the mitochondria, but at high concentrations, it accumulates in the endoplasmic reticulum. The compound denoted by formula B is rhodamine B hexyl ester. At low concentrations, it accumulates in the mitochondria, but at high concentrations, it accumulates in the endoplasmic reticulum. The compound denoted by formula C is ER-tracker Blue White DPX. It accumulates mainly in the endoplasmic reticulum, and stains the Golgi body at high concentrations. It is the fluorescent probe that is employed in the examples. The compounds denoted by A, B, and C are all amphiphilic and cationic, with a moderate lipophilicity. Refer to the reference, why fluorescent probes for an endoplasmic reticulum are selective: an experimental and QSAR-modeling study.

The ampiphilicity index (AI) and hydrophobic index of the compound denoted by A are 4.5 and 4.5, respectively. It has a monovalent cation. The ampiphilicity index (AI) and hydrophobic index of the compound denoted by B are 4.8 and 5.9, respectively. It has a monovalent cation. The ampiphilicity index (AI) and hydrophobic index of the compound denoted by C are 5.1 and 0.7, respectively. It has a monovalent cation. As indicated in the examples, the compound denoted by C has a fluorescence intensity in the case of plasma cells and plasmablasts that is four-fold or more the fluorescence intensity when staining cells other than plasma cells and plasmablasts.

[Formula 1]

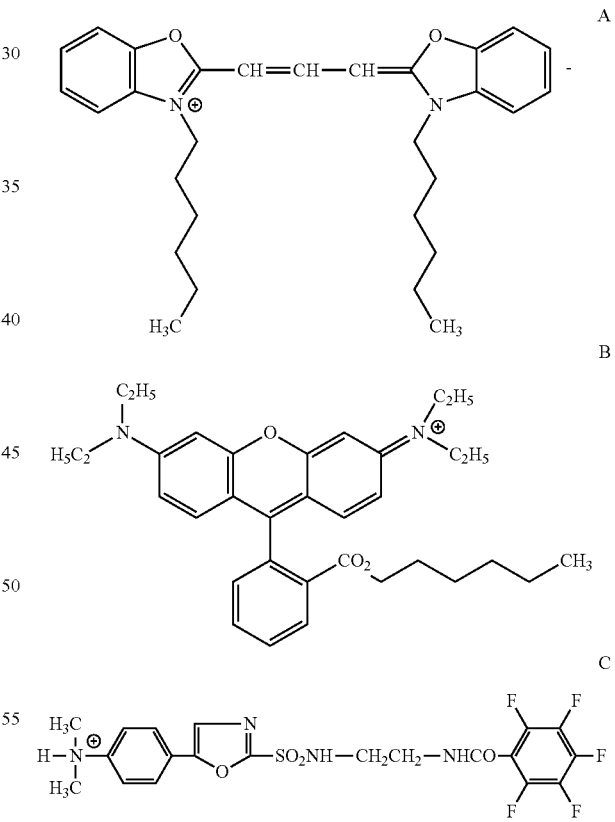

Dyes 1, 5, 7 and 10 are amphiphilic and cationic substances that have medium degrees of lipiphilicity. They are examples of fluorescent probe 1. These dyes are described in US Patent Application Publication US2010/0068752A1 (the entirety of which is hereby incorporated by reference). These dyes can be synthesized based on the description given in the above-cited US patent application publication.

Some are also commercially available. The amphiphilic index (AI) and hydrophobic index of dye 1 are 4.95 and 3.77, respectively, and it has a monovalent cation. The amphiphilic index (AI) and hydrophobic index of dye 5 are 5.11 and 4.32, respectively, and it has a monovalent cation. The amphiphilic index (AI) and hydrophobic index of dye 7 are 4.19 and 3.29, respectively, and it has a monovalent cation. The amphiphilic index (AI) and hydrophobic index of dye 10 are 4.25 and 5.71, respectively, and it has a monovalent cation. The hydrophobic indexes of dyes 1, 5, 7, and 10 were calculated using the calculation software Pallas of CompuDrug. They were calculated as the value of log P (combined)=0.863×log P (ann log p)+0.137×log P (atomic 6), which was the sum of the values obtained by multiplying two independent log P calculation indexes (log P(ann log P), log P(atomic 6) by coefficients to enhance the correspondence with actually measured values. The amphiphilic index was calculated by removing the phosphoric acid group (P—O) from the value of log P (ann log P).

(2) Fluorescently Labeled Glibenclamide and Brefeldin A are Examples of Substances Having Affinity to a Protein Localized in an Endoplasmic Reticulum Above a Certain Degree.

Glibenclamide is a compound with the following formula. It is commercially available under the product names: ER-tracker (registered trademark) Green, (BODIPY®) FL glibenclamide, and ER-tracker (registered trademark) Red. (BODIPY®) TR glibenclamide is sold as a compound of glibenclamide bonded to the fluorescent dye (BODIPY). The glibenclamide compounds are known to bind to the numerous sulphonylurea receptors of ATP-sensitive K+ channels in the endoplasmic reticulum, blocking their action. They are employed as a treatment for diabetes. The dissociation constant of glibenclamide on ATP-sensitive K+ channels is 0.1 to 3.6 nM.

[Formula 3]

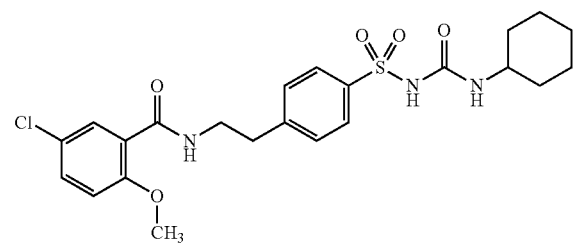

4-[2-(5-Chloro-2-methoxybenzoylamino)ethyl]-N-(cyclohexylcarbamoyl)benzenesulfonamide Brefeldin A is a compound with the following formula. It is sold under the product name BODIPY-Brefeldin A, which is a compound consisting of Brefeldin A to which the fluorescent dye (BODIPY) has been bonded. Brefeldin A blocks the function of the Arf1 protein, a GTP-exchanging factor that acts on vesicle transport from the endoplasmic reticulum to the Golgi body.

[Formula 4]

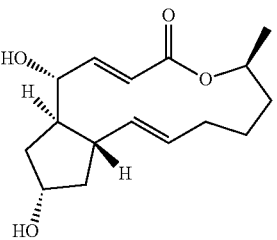

[Formula 2]

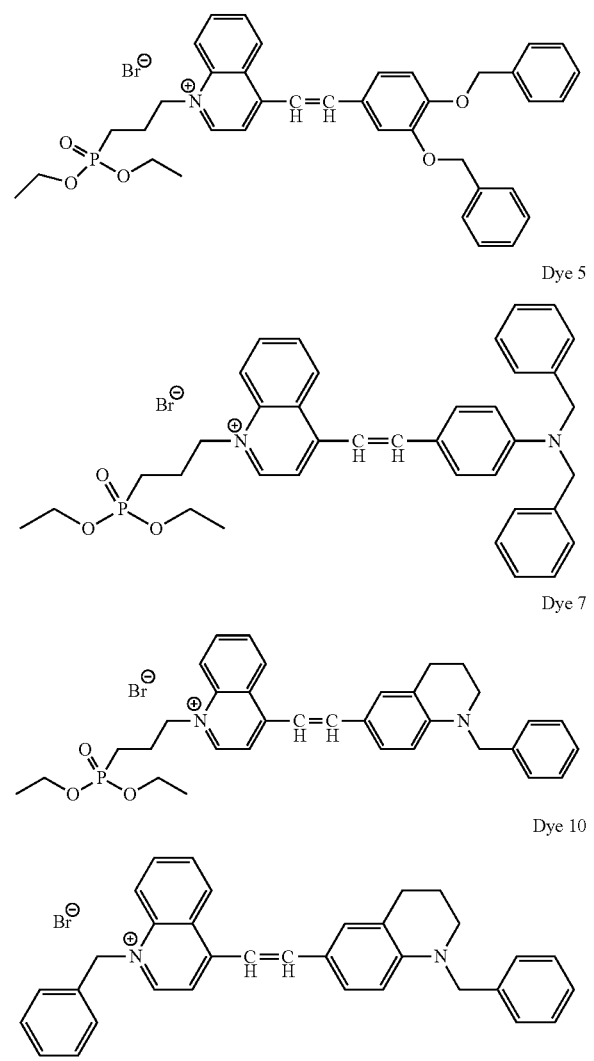

Dye 1

Dye 5

Dye 7

Dye 10

The quantity of fluorescent probe 1 that is added to the lymph fluid, lymphoid tissue, blood cell sample, or bone marrow can be suitably determined based on considerations such as the sensitivity of the detector, the composition of the cell suspension, and the staining time. For example, in the case of ER-tracker Blue White DPX, a quantity falling within a range of 100 nM to 1 μM can be added. However, no limitation to within this range is intended.

<Selection of Cells to which (1) Labeled Target Antigen and (2) Marker have Bound>

Cells to which (1) the labeled target antigen and (2) the marker have bound can be suitably selected based on the types of labels of the target antigen and markers that specifically bind to plasma cells and/or plasmablasts. In the case that both of the label of the target antigen and the marker that specifically binds to plasma cells and/or plasmablasts are a fluorescent label (such as a fluorescent dye), the fluorescence emitted by them can be used to select cells to which (1) the labeled target antigen and (2) the marker have bound. Neither the method of selecting cells to which (1) the labeled target antigen and (2) the marker have bound, nor the device in which this method is utilized, is specifically limited. Existing methods of separating cells at the individual cell level can be employed in devices as is.

Using fluorescent probe 1, plasma cells and plasmablasts (or cells with a high probability of being plasma cells and plasmablasts) are identified in the stained lymph fluid, lymphoid tissue, blood cell sample, or bone marrow based on fluorescence. As set forth above, methods of identifying plasma cells and plasmablasts include (1) the method of observing by fluorescence microscopy the localization of the fluorescent probe in the stained cells; and (2) the method based on the fluorescence intensity emitted by the stained cells.

(1) In the method of observing by fluorescence microscopy the localization of the fluorescent probe in the stained cells, the region of the endoplasmic reticulum contained in the cell is strongly stained (that is, emits intense fluorescence). In the observation of individual cells, cells in which the ratio of the area of the region of the endoplasmic reticulum that has been strongly stained is about 65% or more are identified as plasma cells and plasmablasts. Setting aside the ratio of the area, when the fluorescence intensity of an entire individual cell is adopted as 100%, cells in which the ratio of fluorescence intensity of the endoplasmic reticulum is about 65% or greater can be identified as plasma cells and plasmablasts. In the case of plasma cells and plasmablasts, the fluorescence intensity accounted for by the endoplasmic reticulum in the fluorescence intensity from a single cell as a whole is about 65%, with 35% of the fluorescent dye migrating to other cell organelles (the mitochondria, Golgi body, and plasma membrane).

The ratio of the fluorescence intensity of the entire cell and the fluorescence intensity of the endoplasmic reticulum can be obtained as set forth below by immunostaining proteins that are localized in the endoplasmic reticulum (immunoglobulin in the case of plasma cells and plasmablasts), or expressing recombinant fluorescent proteins with the property of migrating to the endoplasmic reticulum, and using methods of identifying the endoplasmic reticulum of the cells.

For example, 293 cells are employed to cause recombinant protein (red) to be expressed in cultured cells, and these cells are stained with fluorescent probe 1 (for example, ER-tracker Blue White). The image analyzer of a fluorescence microscope is utilized to measure the fluorescence intensity of fluorescent probe 1 accounted for in the cell as a whole and display it as A. It is also used to measure the fluorescent intensity of the fluorescent probe 1 within the region (endoplasmic reticulum) stained with recombinant fluorescent protein (red) and display it as B. Fluorescence intensity B corresponds to the amount of fluorescent probe 1 that is localized in the endoplasmic reticulum. Thus, the ratio of the fluorescence intensity B of the endoplasmic reticulum of the cell to the fluorescence intensity A of the entire cell can be denoted as B/A×100(%). In the results given in the examples, for plasma cells and plasmablasts, when the intensity A of ER-tracker Blue/White accounted for in a single cell as a whole and the fluorescence intensity B of ER-tracker Blue/White in the region (endoplasmic reticulum) stained by immunoglobulin (green) were measured, the value of B/A×100 was 65% or greater.

(2) Plasma cells and plasmablasts can be identified based on fluorescence intensity, for example, with a fluorescence scanner, fluorescence microscope, flow cytometer, or cell sorter. The fluorescence intensity obtained with plasma cells and plasmablasts with fluorescent probe 1 is, for example, three times or more, desirably four times or more, and preferably, five times or more the fluorescence intensity obtained with cells other than plasma cells and plasmablasts, as set forth above. Thus, it is possible to readily identify plasma cell and plasmablast candidates from cells that have been stained with fluorescent probe 1 based on fluorescence intensity using the above fluorescence scanner or the like.

Simply setting a high fluorescence intensity ratio (plasma cells and plasmablasts/cells other than plasma cells and plasmablasts) as a criterion for selecting candidate plasma cells and plasmablasts raises the ratio of true plasma cells and plasmablasts contained among the plasma cell and plasmablast candidates. A higher fluorescence intensity is exhibited than by cells other than plasma cells and plasmablasts. However, there is a possibility that plasma cells and plasmablasts exhibiting only a fluorescence intensity that is lower than the fluorescence intensity serving as a criterion will be excluded. Accordingly, it is desirable to take into account the properties of the plasma cells and plasmablasts that are contained in the sample in the form of lymph fluid, lymphoid tissue, or blood cells, particularly the degree of development of the endoplasmic reticulum, and to select a fluorescence intensity ratio as a criterion for selecting candidate plasma cells and plasmablasts.

The method of the present invention further desirably comprises collecting (sorting) candidate plasma cells and plasmablasts that have been identified by the method set forth above. The cells that have been identified can be collected by sorting with a cell sorter. Plasma cells and plasmablasts that have been identified based on fluorescence or determined to be candidate plasma cells or plasmablasts (or have a high probability of being plasma cells or plasmablasts) based on fluorescence are sorted using a cell sorter.

In the selection of cells, cells can be selected as groups of multiple cells and separated. Desirably, however, cells are selected one by one and separated. All of the cells that are selected at this stage will be able to bind the target antigen. However, the antibodies to the target antigen which each cell possesses will not necessarily be identical. The amino acid sequences at the antigen-binding sites of individual antibodies can be expected to differ. Accordingly, the method for producing a target antigen specific antibody or antibody fragment, which is described further below, makes it possible to obtain different monoclonal antibodies that specifically bind the same target antigen by application to individual cells.

The cells that have been selected by this method exhibit the ability to bind the target antigen and present a strong possibility of being plasma cells and plasmablasts. This method makes it possible to select nonhuman animal cells in the form of plasma cells and/or plasmablasts that bind specifically to the target antigen.

The HU method for humans will be described next. In the HU method, lymph fluid, lymphoid tissue, a blood cell sample, or bone marrow derived cells from a human are collected. The lymphocytes, lymphoid tissue, blood cell sample, or bone marrow derived cells are either sensitized in vitro to a target antigen, or lymph fluid, lymphoid tissue, a blood cell sample, or bone marrow derived cells provided by a human having antibodies to the target antigen are employed as a sample for collecting cells. The method set forth above can be used to sensitize in vitro the lymph fluid or the like that has been collected to the target antigen. That is, antigen-presenting cells in the form of dendritic cells, T cells, or B cells from humans are collected. Next, the antigen is subjected to the action of the dendritic cells in a test tube, phagocytosed, and digested to fabricate mature dendritic cells that have the ability to present antigen. To these are then added T cells, B cells, cytokines such as interleukin-2, and immunostimulators such as poly(dI-dC). B cells that react to the antigen are proliferated and caused to differentiate in a test tube, ultimately yielding antibody-producing cells in the form of plasma cells and plasmablasts.

The lymph fluid or the like that is provided by a human having antibodies is, more specifically, blood that has been provided by a human possessing antibodies to the target antigen, or lymph nodes or the like that have been surgically excised as part of the treatment of a disease. Still more specifically, blood cells or lymphocytes are separated from blood or tissue provided by a human possessing antibodies to the target antigen. These are then combined with (1) labeled target antigen and (2) a marker that has selectively bound to the plasma cells and/or plasmablasts. The target antigen used in immunization, the (1) labeled target antigen, and the (2) marker that has selectively bound to the plasma cells and/or plasmablasts are identical to those in the NHA method. The cells to which the marker that has selectively bound to the (1) labeled target antigen and (2) plasma cells and/or plasmablasts are selected in the same manner as in the NHA method.

In the HU method, a sample that has been provided by a human possessing antibodies to the target antigen is employed. Thus, human plasma cells and/or plasmablasts that specifically bind to the target antigen can be selected.

[Method for Producing Target Antigen Specific Antibody or Antibody Fragment]

The second aspect of the present invention is a method for producing a target antigen specific antibody or antibody fragment.

The present method comprises:
selecting plasma cells and/or plasmablasts specifically binding to a target antigen by the method of the present invention as set forth above;
collecting a gene for an antibody to the target antigen from the selected cells;
identifying the base sequence thereof; and
preparing the antibody or antibody fragment based on the base sequence of the gene that has been identified. This method makes it possible to produce an antibody or an antibody fragment that is specific to the target antigen.

The method of selecting plasma cells and/or plasmablasts that specifically bind to a target antigen in the above method of the present invention is as set forth above.

<Base Sequence Identification of Antibody Genes>

The gene of an antibody to the target antigen is collected from the cell that has been collected and the base sequence thereof is identified. The selected cell exhibits the property of binding to the target antigen and is a plasma cell or a plasmablast. In the present invention, the cells that have been selected can be handled in groups of multiple cells to collect and identify antibody genes. However, it is desirable for the antibody gene of an individual cell to be collected, and the base sequence thereof to be identified. In this manner, it becomes possible to obtain different monoclonal antibodies that bind specifically to the same target antigen.

Known methods can be employed to collect the gene of an antibody to the target antigen from a cell that has been selected, and to identify the base sequence thereof.

The method described in WO2009/091048 (US2011/0020879A1) (the entirety of which is hereby incorporated by reference), for example, can be employed as the method of collecting a gene for an antibody to the target antigen and synthesizing cDNA from the antibody gene that has been collected. A cloning method employing the homologous recombination method described in WO2009/110606, US2011/0117609A1 (the entirety of which is hereby incorporated by reference), for example, can be employed as the method of cloning cDNA. Known DNA base sequencing methods can be implemented to identify the base sequence of the cDNA that has been synthesized. The gene of the antibody to the target antigen can be identified by identifying the base sequence of the cDNA.

[Method]

The method described in WO2009/091048 is a reaction method employing a reaction device in which a plurality of projecting barriers are arranged in a line on either surface of a substrate, and said projecting barrier has at least one cutout portion and a space capable of holding a droplet therein, and at least the surface of the substrate holding the droplet has pure water contact angle of 90 to 150 degree; wherein a substance immobilized on magnetic beads is sequentially transferred in or between droplets containing a surface tension reducing agent held in the spaces for holding a droplet defined by said projecting barriers by means of a magnet on the opposite surface of the substrate to the surface having the projecting barriers, so that a reaction and/or a washing is performed. This method can be carried out by employing, for example, oligo dT, which can bind to mRNA of a selected cell, as a substance immobilized on magnetic beads.

A method of synthesizing cDNA can be carried out by employing the above described reaction device in which said device has at least two projecting barriers in one lengthwise row, and can comprise steps of: that the spaces for holding a droplet defined by said two projecting barriers hold a droplet of cytolysis solution and a droplet of cDNA synthesis solution, which both solutions contain a surface tension reducing agent, in this sequence, respectively; that mRNA immobilized on magnetic beads is sequentially transferred into the droplets held in the spaces for holding a droplet defined by said two projecting barriers by means of a magnet on the opposite surface of the substrate to the surface having the projecting barriers; and that cDNA immobilized on the magnetic beads is obtained.

The above described cDNA synthesis method can employ, for example, a reaction device in which at least four projecting barriers are arranged in one lengthwise row. The spaces defined by the four projecting barriers such as U-shape projections hold a cytolysis solution, an mRNA washing solution, a cDNA synthesis solution and a cDNA washing solution in this order, respectively (referring to FIG. 3), and an mRNA immobilized on magnetic beads is sequentially transferred into droplets held in the spaces defined by the four projecting barriers by means of a magnet on the opposite surface of the substrate to the surface having the projecting barriers of the substrate, and thereby cDNA immobilized on the magnetic beads is obtained.

In the cDNA synthesis method, the volume of a space defined by a U-shape projection of a reaction device is just as well, for example, in the range of 0.5 to 100 μl.

The cytolysis solution held in the space defined by the first U-shape projection is, for example, a solution of 3 μl in total, which contains 100 mM Tris HCl (pH7.5), 500 mM LiCl, 1% dodecyl lithium sulfate and 5 mM dithiothreitol.

The mRNA washing solution held in the space defined by the second U-shape projection is, for example, a solution of 3 µl in total, which contains 10 mM Tris HCl (pH7.5), 0.15M LiCl and 0.1% dodecyl lithium sulfate.

The reverse transcription reaction washing solution held in the space defined by the third U-shape projection is, for example, a solution of 3 µl in total, which contains 50 mM Tris HCl (pH8.3), 75 mM KCl, 3 mM MgCl2, 0.1% Triton X-100, 0.5 mM dNTP, 5 mM DTT and 2 units RNase inhibitor.

The reverse transcription reaction solution held in the space defined by the fourth U-shape projection is, for example, a solution of 3 µl in total, which contains 50 mM Tris HCl (pH8.3), 75 mM KCl, 3 mM MgCl2, 0.1% Triton X-100, 0.5 mM dNTP, 5 mM DTT, 2 units RNase inhibitor and 8 units SuperScript III Reverse transcriptase.

However, these are exemplifications, and it is not limited to these exemplified solutions.

An mRNA immobilized on magnetic beads is prepared. mRNA is not limited for its kind, length and so on. Any kind of mRNA of biological origin can be used. Magnetic beads, for example, which have the particle size of 2.8 µm and oligo dT25 covalently bound to the surface, are used. Immobilization of mRNA on magnet beads can be conducted by the followings.

Magnetic beads are suspended in a cytolysis solution with the concentration of 10 mg/ml. One to 100 cells are added to the solution. By these procedures, mRNA in cells is, via its polyA tail, bound to oligodT25 immobilized on magnet beads.

A mRNA immobilized on magnetic beads is sequentially transferred into the solutions (droplets) held in spaces defined by the four U-shape projections by means of a magnet on the opposite surface of a substrate to the surface having projections. The magnet is, for example, a small size neodymium magnet. The magnet beads are maintained in each droplet for required time for reaction or washing. The required time for reaction or washing depends on reaction condition and washing condition, but for example, is between 1 second to 1 hour.

The above reaction and washing can be carried out at normal temperature or room temperature, but if needed, temperature can be controlled. Further, when a droplet has a small amount, there may be a case that a solvent of a solution is vaporized, and thus, it is preferable that a reaction device is placed in a closed container and the humidity in the container keeps constant, thereby vaporization of solvent is avoided. In order to keep the humidity in the container be constant, a vessel containing water or other suitable aqueous solution can co-exist in the above closed container.

The mRNA immobilized on magnet beads sequentially abides in and passes through the solutions/droplets held by the spaces defined by the above four U-shape projections to obtain cDNA immobilized on the magnetic beads. The thus obtained cDNA can be subjected to the next step without be cut from the magnetic beads. Particularly, the obtained cDNA can be subjected to the cloning method described below, and the like.

A cloning method using the method described in WO2009/110606 is a method employing, as a method for homologous recombination, a method comprising: using a PCR product and a linearized vector, wherein the PCR product contains a target gene (an antibody gene) sequence that has amplification primer sequences P1 and P2 on its both ends, and the linearized vector has homologous recombination regions VP1 and VP2 comprising nucleotide sequences homologous to the amplification primer sequences P1 and P2 of the PCR product and the linearized vector also has a homologous recombination region VT1 comprising a nucleotide sequence homologous to a sequence T1 which is a part of sequence in the PCR product internal to P1 on the terminal side of VP1 and/or a homologous recombination region VT2 comprising a nucleotide sequence homologous to a sequence T2 which is a part of sequence in the PCR product internal to P2 on the terminal side of VP2, provided that at least one of T1 and T2 has a nucleotide sequence specific to the target gene; making the PCR product be subject to homologous recombination reaction and thereby be inserted into the vector; and obtaining a recombinant DNA molecule in which a PCR product of interest is specifically inserted into a vector. The PCR product containing the target gene (antibody gene) sequence that has amplification primer sequences P1 and P2 on its both ends can be obtained from the obtained cDNA as described above by the method described in WO2009/110606. Further, the cloning for a target antibody gene can be carried out by preparing a recombinant DNA molecule in which a PCR product of interest is specifically inserted into a vector by the above method for homologous recombination, and amplifying a recombinant having the resulting recombinant DNA molecule.

Also, a target gene contained in amplified recombinant DNA molecule (recombinant vector) is for example obtained by digesting the vector with restriction enzyme and purified if needed. Isolation and purification of a target gene can be performed by a conventional method. For example, gel extraction or column purification can be listed as isolation and purification of a target gene. Isolated and purified target gene can be used for, for example, nucleotide sequence determination, insertion into an expression vector, and functional analysis of the target gene.

<Preparation of Antibody or Antibody Fragment>

An antibody or an antibody fragment can be prepared based on the base sequence of the gene that has been identified.

The antibody or antibody fragment can be prepared based on the base sequence of the gene that has been identified using an antibody gene fragment fabricated by the method of specifically fabricating a DNA fragment described in WO2011/027808.

The method described in WO2011/027808 is as follows.

[1]

A method for producing a joined DNA fragment in which joining DNA regions have been joined on both ends of a target gene, comprising:

(1) preparing, from a double-stranded gene fragment comprising a target gene sequence, a 3' end protruding double-stranded gene fragment containing a target gene in the middle portion thereof, having associative regions on the two termini thereof, the two associative regions having base sequences that do not mutually associate, at least a portion of the base sequence of one or both of the regions being an inherent base sequence contained in the target gene, with a protruding terminus of one or more nucleotides being present on the 3' ends of both of the associative regions;

(2) preparing a double-stranded joining DNA fragment, containing a joining DNA region in the middle portion thereof, and having associative regions on the two termini thereof; wherein (3-1) one of the associative regions of the 3' end protruding double-stranded gene fragment is comprised of a base sequence that is homologous with the associative region of one terminus of the double-stranded joining DNA fragment, with the sequence on the terminus to which the 3' protruding end has been added being the side that connects to the joining DNA region in one of the associative regions of the double-stranded joining DNA fragment;

(3-2) the terminus protruding from the one associative region of the 3' end protruding double-stranded gene fragment does not have a strand-elongating function in a DNA synthesis reaction;

(3-3) the other associative region of the 3' end protruding double-stranded gene fragment is comprised of a base sequence that is homologous with the associative region of the other terminus of the double-stranded joining DNA fragment, with the sequence on the terminus to which the 3' protruding end has been added being the side that connects to the joining DNA region in the other of the associative regions of the double-stranded joining DNA fragment;

(3-4) the terminus protruding from the other associative region of the 3' end protruding double-stranded gene fragment does not have a strand-elongating function in the DNA synthesis reaction; and (4) subjecting the 3' end protruding double-stranded gene fragment and double-stranded joining DNA fragment to at least two cycles of a thermal denaturation, re-association, and DNA synthesis reaction to obtain a joined DNA fragment.

The producing described in [1] can be illustrated, specifically as followings.

(a) Denoting one of the associative regions as "region 1" and the other associative region as "region 2," the joined DNA fragment comprises at least one sequence schematically denoted by region 2-joining DNA region-region 1-target gene region-region 2-joining DNA region-region 1.

(b) The joining DNA region is comprised of two joining DNA regions in the form of region A and region B; one of the associative regions of the 3' end protruding double-stranded gene fragment, from the terminus side, comprises sequences P1 and T1; the other, from the terminus side, is comprised of sequences P2 and T2; at least one sequence T1 or sequence T2 comprises an inherent base sequence that is contained in a target gene sequence; one of the associative regions of the double-stranded joining DNA fragment comprises, from the terminus side, sequences VP1 and VT1; the other, from the terminus side, comprises sequences VP2 and VT2; sequences VP1 and VT1 comprise base sequences that are homologous with sequences P1 and T1, respectively; and sequences VP2 and VT2 have base sequences that are homologous with sequences P2 and T2, respectively.

(c) The 3' end protruding double-stranded gene fragment is denoted by P1-T1-target gene-T2-P2; the double-stranded joining DNA fragment is denoted by VT2-VP2-sequence B-sequence A-VP1-VT1; the joined DNA fragment is a DNA fragment comprising at least one unit of VT2-VP2 (T2-P2)-sequence B-sequence A-VP1-VT1(P1-T1)-target gene-VT2-VP2(T2-P2)-sequence B-sequence A-VP1-VT1 (P1-T1); where VT2-VP2(T2-P2) means VT2-VP2 that is homologous with T2-P2; and where VP1-VT1(P1-T1) means VT1-VP1 that is homologous with T1-P1.

(d) The sequence without a strand-elongating function in the reaction synthesizing the DNA with a protruding end on the 3' end of sequence P2 is a sequence that is not homologous with the sequence adjacent to VP2 of sequence B, and the sequence without a strand-elongating function in the reaction synthesizing the DNA with a protruding end on the 3' end of sequence P1 is a sequence that is not homologous with the sequence adjacent to VP1 of sequence A.

(e) The protruding ends are sequences containing a dideoxynucleotide(s) on the 3' ends thereof.

[2]

A DNA fragment comprising at least a portion of at least one joining DNA region and the entire sequence of a target gene may be prepared by a method comprising:

conducting PCR, with a joined DNA fragment produced by the method according to [1] as template, using a forward primer and a reverse primer functioning in different joining DNA regions contained in a joined DNA fragment to amplify at least a portion of at least one joining DNA region and the entire sequence of a target gene contained in the joined DNA fragment.

A method for producing a DNA fragment may be carried out by conducting PCR employing a forward primer contained on the 3' end a portion of the base sequence of sequence A toward a target gene and employing a reverse primer contained on the 3' end a portion of the base sequence of sequence B toward the target gene with the joined DNA fragment produced by the method according to (b) of [1] as template to obtain a DNA fragment in which sequence A, the sequence of the target gene, and sequence B are joined.

[3]

(a) The production method according to (b)(c) of [1] and (a)(b) of [2], may further comprise causing deoxynucleotide terminal transferase to act upon the polydeoxynucleotide and double-stranded DNA fragment containing the sequence of the target gene to obtain a 3' end protruding double-stranded gene fragment comprising the sequence of the target gene (wherein sequence P1 is present on one terminus of the double-stranded DNA fragment containing the target gene sequence and sequence T1 is present within a portion of sequence P1, and sequence T1 comprises a base sequence that is inherent to the target gene).

(b) One or both of sequence T1 and sequence T2 may comprise a base sequence that is inherent to the target gene.

(c) One or both of sequence P1 and sequence P2 may comprise a base sequence that is inherent to the target gene.

In [1] to [3], the target gene may be an antibody gene, the 3' end protruding double-stranded gene fragment may contain a sequence derived from an antibody gene or T cell receptor gene, and region VP1 and region VT1 in the double-stranded joining DNA fragment comprising sequence A or the double-stranded joining DNA may comprise sequences that are, or are not, derived from an antibody gene.

[5]

In [1] to [3], the target gene may be an antibody gene, the 3' end protruding double-stranded gene fragment may contain a sequence that is derived from the antibody gene, and region VP2 and region VT2 in the double-stranded joining DNA fragment having sequence B or the double-stranded joining DNA fragment may be sequences that are, or are not, derived from antibody.

[6]

An antibody may be prepared by employing the joined DNA fragment prepared by the method according to [4] or [5]. A method for producing an antibody employing the obtained joined DNA fragment may be carried out by means, such as a cationic ribosome method. Specifically, the antibody can be prepared by introducing the above joined DNA fragment into cells such as cells of 293T strain, then culturing the cells to express the antibody gene.

[Antibody Genes and Peptides]

The present invention includes a gene and a peptide for the variable region and constant region of a monoclonal antibody to human insulin obtained for the first time ever by the above-described method of the present invention, and to a guinea pig monoclonal antibody to human insulin.

(1) A gene of the γ chain constant region of the guinea pig antibody to human insulin, which has the base sequence indicated by SEQ ID NO: 1 in the SEQUENCE LISTING; a gene coding for a peptide in the γ chain constant region of a guinea pig antibody to human insulin, which has the amino acid sequence indicated by SEQ ID NO: 4; and a peptide of the γ chain constant region of a guinea pig antibody to human insulin, which has the amino acid sequence indicated by SEQ ID NO: 4.

(2) A gene of the κ chain constant region of the guinea pig antibody to human insulin, which has the base sequence indicated by SEQ ID NO: 2 in the SEQUENCE LISTING; a gene coding for a peptide in the κ chain constant region of a guinea pig antibody to human insulin, which has the amino acid sequence indicated by SEQ ID NO: 5; and a peptide of the κ chain constant region of a guinea pig antibody to human insulin, which has the amino acid sequence indicated by SEQ ID NO: 5.

(3) A gene of the λ chain constant region of the guinea pig antibody to human insulin, which has the base sequence indicated by SEQ ID NO: 3 in the SEQUENCE LISTING; a gene coding for a peptide in the λ chain constant region of a guinea pig antibody to human insulin, which has the amino acid sequence indicated by SEQ ID NO: 6; and a peptide of the λ chain constant region of a guinea pig antibody to human insulin, which has the amino acid sequence indicated by SEQ ID NO: 6.

(4) A gene of the γ chain variable region of a guinea pig antibody to human insulin, which has the base sequence indicated by any one of SEQ ID NOs: 7 to 18 in the SEQUENCE LISTING; a gene coding for a peptide of the γ chain variable region of a guinea pig antibody to human insulin, which has the amino acid sequence indicated by any one of SEQ ID NOs: 19 to 30; and a peptide of the γ chain variable region of a guinea pig antibody to human insulin, which has the amino acid sequence indicated by any one of SEQ ID NOs: 19 to 30.

(5) A gene of the κ chain variable region of a guinea pig antibody to human insulin, which has the base sequence indicated by any one of SEQ ID NOs: 31 to 42 of the SEQUENCE LISTING; a gene coding for a peptide of the κ chain variable region of a guinea pig antibody to human insulin, which has the amino acid sequence indicated by any one of SEQ ID NOs: 43 to 54; and a peptide of the κ chain variable region of a guinea pig antibody to human insulin, which has the amino acid sequence indicated by any one of SEQ ID NOs: 43 to 54.

(6) A guinea pig monoclonal antibody to human insulin, which has a γ chain having the amino acid sequence indicated by any one of SEQ ID NOs: 19 to 30 as a variable region, and the amino acid sequence indicated by SEQ ID NO: 4 as a constant region.

(7) A guinea pig monoclonal antibody to human insulin, which has a κ chain having the amino acid sequence indicated by any one of SEQ ID NOs: 43 to 54 as a variable region and the amino acid sequence indicated by SEQ ID NO: 5 as a constant region.

(8) A guinea pig monoclonal antibody to human insulin, which comprises a κ or γ chain containing a combination of CDR1, CDR2 and CDR3 selected from each below:

| κchain CDR1 | κchain CDR2 | κchain CDR3 |
|---|---|---|
| QTINNY | GTN | QQSRSSPFT |
| QTISSY | GTN | QQSNSSPFT |
| QSVSSY | WAT | QQSKTSPFT |
| QTISSY | GTN | QQSRSSPFT |
| SSVNNNF | RTS | LQSNSYT |
| QSLLSRYNNKNN | WAS | MQYYHFRT |
| SSISESY | WAS | QQSTSYRT |
| SSLINNY | RTS | QESSSYYGT |
| SSISDSY | RTS | QQSTTYRT |
| STLIKNY | RTS | QESTSYYGT |
| SNLINNY | RTS | QESTSYYGT |
| SSLINNY | RTS | QEYTSYYGT |
| SSVNNNF | RTS | QQSRSYT |
| QSIKNY | WAT | QQSKTSPSL |
| QSLLSSENNKNY | LAS | MQTFGTPGR |

| γchain CDR1 | γchain CDR2 | γchain CDR3 |
|---|---|---|
| GFSITTSGYA | IAYNGGT | ARGPLYSVGRAWSNYWYFDF |
| GFSITTSGYG | IAYNGGT | ARGPLYYVGRAWSNYWYFDF |
| GFSITTSGYG | IAYNGGT | ASGPLYRIGAVWSNYRSFDF |
| GFSITTSGYA | IAYNGGT | ARGPLYYVGRAWSNYWYFDF |
| GFSLMDYS | IWSSGST | ARAQYFDV |
| EFSITTSGYG | IAYNGAT | ARSGSHSSGVYYIP-SYFDV |
| GMTLSNYA | IVHSGSNT | ATDMGWNSALDV |
| GFSLTGYP | IWSFGST | ARHGSGYFDI |
| GLTLSNYA | ISHSGSRT | ATDMGWNSALDI |
| GFSLSGYP | IWPFGGT | ASHGNGYDI |
| GFSLTGYS | IWSFGST | ARHGGGYFDI |
| GFSLTGYS | IWNFGGT | TRHGSGYFDM |
| GFSLSGYS | IWATGST | ARAQFFDV |
| GFSIATSGYG | IAYNGGT | ARGPLYSIGGVWSNYGYFDF |
| GFTFSRYG | ISDSGSNT | GSVGSLY |

The peptide and gene of the variable region and constant region of a guinea pig antibody to human insulin of the present invention, and the monoclonal antibody to human insulin, can be prepared with reference to the description of the examples set forth further below using known methods of preparing DNA and peptides.

EXAMPLES

The present invention is described with greater specificity below through examples. However, the examples are provided as illustrations, and are not intended to limit the present invention.

Example 1

Preparation of Rat Monoclonal Antibodies

[Materials and Methodology]

Female Wistar rats six weeks of age were employed as the immune animals. The antigen was GFP. In immunization, 50 μg of GFP was injected intramuscularly three times at one-month intervals on both sides of the base of the tail of the rats. Once immunity had been established, the iliac lymph nodes were collected from the rats. The GFP was fluorescence labeled with Alexafluor 488 and purified by gel filtration.

Iliac lymph node-derived lymphocytes were suspended in a 0.5% PBS bovine serum albumin solution, after which GFP (0.5 μg/mL) was added. The mixture was stirred for 30 minutes at 4° C. to label the cells with antigen. The cells were centrifuged and suspended in DMEM medium. To this was added ER-tracker (1 μm) and the mixture was left standing for 5 minutes at room temperature to stain the endoplasmic reticulum. The cells were washed with PBS, and then separated in a cell sorter into an antigen specific plasma cell fraction of GFP-positive and intensely ER-tracker positive cells and an antigen-nonspecific plasma cell fraction of GFP negative and ER-tracker intensely positive cells.

[Results]

The lymphocytes prepared from iliac lymph nodes were stained with anti-rat IgG antibody (green) and ER-tracker and then observed under a fluorescence microscope. As a result, although weak, the expression of IgG was found on the surface of strongly ER-tracker positive plasma cells (FIG. 1).

Next, an attempt was made to identify antigen specific plasma cells by subjecting this membrane-bound IgG to the action of GFP. An ilium-derived rat lymphocyte suspension was stained with Alexafluor 488 labeled GFP and ER-tracker and analyzed with a flow cytometer. As a result, GFP-positive cell groups were present, as shown in FIG. 2A. Most of these GFP-positive cell groups were signals derived from nonspecific GFP adsorption or B cells expressing low affinity membrane-bound antibodies. To identify the antigen specific plasma cells among them, those cells that were strongly GFP positive and strongly ER-tracker positive were separated with a cell sorter as antigen specific plasma cells and those cells that were GFP negative and strongly ER-tracker positive were separated as nonspecific plasma cells (High and Low in FIG. 2A). The cells that had been separated were immobilized, treated to solubilize the cell membrane, and stained with anti-rat IgG antibody. As a result, the cells that were obtained expressed large amounts of antibody in the cytoplasm and were thus determined to be plasma cells (FIG. 2B).

cDNA Synthesis cDNA was synthesized and the immunoglobulin gene was amplified in accordance with the methods described in "Reaction device, reaction method and method of synthesizing cDNA" (WO2009/091048) (FIG. 3).

Individual rat plasma cells that had been separated with a cell sorter were added to 3 µL of cell lysate (100 mM TrisHCl (pH 7.5), 500 mM LiCl, 1% lithium dodecylsulfate (LiDS), and 5 mM dithiothreitol) containing 3 µg of magnetic beads (Dynabeads) bonded to oligo-dT25. The mRNA in the cells was caused to bind to the magnetic beads. Next, the magnetic beads were washed once with 3 µL of mRNA cleaning solution A (10 mM TrisHCl (pH 7.5), 0.15 M LiCl, and 0.1% LiDS) followed by 3 µL of mRNA cleaning solution B (75 mM KCl, 3 mM MgCl2, 0.1% TritonX, 0.5 mM dNTP, 5 mM DTT, and 2 units of RNase inhibitor). cDNA was then synthesized. After washing, to the beads were added 3 µL of cDNA synthesis solution (50 mM TrisHCl (pH 8.3), 75 mM KCl, 3 mM MgCl2, 0.1% TritonX-100, 0.5 mM dNTP, 5 mM DTT, 2 units of RNase inhibitor, and 10 units of SuperScriptIII Reversetranscriptase (Invitrogen)) and the mixture was reacted for one hour at 37° C. Next, the magnetic beads were washed with 3 µL of 3' tailing cleaning solution (50 mM potassium phosphate (pH 7.0), 0.5 mM dGTP, 0.1% TritonX-100, and 4 mM magnesium chloride). An additional 3 µL of 3' tailing reaction solution (50 mM potassium phosphate (pH 7.0), 0.5 mM dGTP, 0.1% TritonX-100, 4 mM magnesium chloride, and 10 units of terminal deoxynucleotidyltransferase) was added and the mixture was reacted for 30 minutes at 37° C.

Amplification of Rat γ and κ Chain Variable Region Gene Fragments

Magnetic beads were washed with 3 µL of TE solution (10 mM TrisHCl (pH 7.5), 1 mM EDTA, and 0.1% TritonX-100) after which the 5'-RACE PCR method was employed to amplify the human immunoglobulin γ chain and κ chain genes. In the first round PCR reaction, 25 µL of PCR reaction solution (containing 0.2 µM of each primer, 0.2 mM of dNTP, and 1 unit of TakaraBio PrimeSTAR heat-resistant DNA polymerase) was added to the magnetic beads and 35 cycles of reactions for 30 seconds at 94° C. and 40 seconds at 68° C. were conducted. The primer (a) employed was annealed to the poly-G added to the 3' end of the cDNA by TdT. Primer sequence (b) was derived from the constant region of the rat immunoglobulin γ chain gene. Primer sequence (c) was derived from the constant region of the rat immunoglobulin κ chain gene.

After the reaction, 225 µL of water was added to the PCR solution and 1 µL of the 10-fold diluted solution was employed as template. Primers (d) and (e) were employed to conduct an amplification reaction of the variable region of the rat immunoglobulin γ chain gene under the same conditions as in the first round PCR. Similarly, primers (d) and (f) were employed to conduct an amplification reaction of the variable region of the rate immunoglobulin κ chain gene. The primers employed were:

```
First round PCR sense primer
                                     (SEQ ID NO: 55)
5-GCTAGCGCTACCGGACTCAGATCCCCCCCCCCCCCDN-3  (a)

First round PCR γ chain amplification
antisense primer
                                     (SEQ ID NO: 56)
5- GCAGGTGACGGTCTGGCTGGRCCAGGTGCTGGA-3  (b)

First round PCR κ chain amplification
antisense primer
                                     (SEQ ID NO: 57)
5- TCGTTCAGTGCCATCAATCTTCCACTTGAC-3  (c)

Second round PCR amplification sense
primer
                                     (SEQ ID NO: 58)
5-CGCTAGCGCTACCGGACTCAGATCCC-3  (d)

Second round PCR γ chain amplification
antisense primer
                                     (SEQ ID NO: 59)
5- CTGCAGGACAGCTGGGAAGGTGTGCAC-3  (e)

Second round PCR κ chain amplification
antisense primer
                                     (SEQ ID NO: 60)
5- TAACTGTTCCGTGGATGGTGGGAAGAT-3  (f)
```

Following the reaction, a 1 µL quantity of each of the PCR solutions was measured out and conversion to expression units of κ and γ chain immunoglobulin gene fragments was confirmed by the agarose gel electrophoresis method (see the upper part of FIG. 3).

Preparation of Rat Immunoglobulin Linearized Expression Vector

Expression units of rat γ chain gene and κ chain gene were prepared in accordance with the methods of "Method for Specifically Producing a Joined DNA Fragment Comprising a Sequence Derived from a Target Gene" (WO2011/027808).

That is, to 1 µL quantities of individual PCR products amplified by the 5'-RACE-PCR method were added 2 units of terminal dexoynucleotidyl transferase and a reaction was conducted for 30 minutes at 37° C. Subsequently, heating was conducted for 5 minutes at 94° C. to halt the enzymatic reaction.

To the 3' end polynucleotide addition rat γ chain gene solution prepared above was added 10 ng of rat γ chain gene joining double-stranded DNA fragment, 10 pmol of primers (g) and (h), and 10 nmol of dNTP. TakaraBio PrimeSTAR heat-resistant DNA polymerase was employed in 25 µL of reaction solution to conduct five cycles of reactions of 40 seconds at 94° C. and 4 minutes at 70° C. followed by 30 cycles of reactions of 40 seconds at 94° C., 40 seconds at 60° C., and 4 minutes at 72° C. to prepare rat γ chain gene expression units.

Similarly, to a rat κ chain gene solution were added rat κ chain gene joining double-stranded DNA fragments and a reaction was conducted to prepare rat κ chain gene expression units.

```
                                              (SEQ ID NO: 61)
       5-AGAGAAACCGTCTATCAGGGCGATGGC-3 (g)

(SEQ ID NO: 62)
       5-AGAGACCCTTTGACGTIGGAGTCCACG-3 (h)
```

Following the reaction, a 1 µL quantity of PCR solution was measured out and the conversion to κ and γ chain immunoglobulin gene fragment expression units was confirmed by agarose gel electrophoresis (see the lower portion of FIG. 3).

A Gene Joining Double-Stranded DNA Fragment

The rat γ chain gene joining double-stranded DNA fragment (SEQ ID NO: 63) consists of a rat γ chain constant region (1-873), a joining sequence II (1-54), a polyA added signal (1045-1051), a CMV promoter (1577-2172), and a joining sequence 1 (2173-2201).

```
TGGAACTCTGGAGCCCTGTCCAGCGGTGTGCACACCTTCCCAGCTGTCCT
GCAGTCTGGGCTCTACACTCTCACCAGCTCAGTGACTGTACCCTCCAGCA
CCTGGCCCAGCCAGACCGTCACCTGCAACGTAGCCCACCCGGCCAGCAGC
ACCAAGGTGGACAAGAAAATTGTGCCCAGAAACTGTGGAGGTGATTGCAA
GCCTTGTATATGTACAGGCTCAGAAGTATCATCTGTCTTCATCTTCCCCC
CAAAGCCCAAAGATGTGCTCACCATCACTCTGACTCCTAAGGTCACGTGT
GTTGTGGTAGACATTAGCCAGGACGATCCCGAGGTCCATTTCAGCTGGTT
TGTAGATGACGTGGAAGTCCACACAGCTCAGACTCGACCACCAGAGGAGC
AGTTCAACAGCACTTTCCGCTCAGTCAGTGAACTCCCCATCCTGCACCAG
GACTGGCTCAATGGCAGGACGTTCAGATGCAAGGTCACCAGTGCAGCTTT
CCCATCCCCATCGAGAAAACCATCTCCAAACCCGAAGGCAGAACACAAG
TTCCGCATGTATACACCATGTCACCTACCAAGGAAGAGATGACCCAGAAT
GAAGTCAGTATCACCTGCATGGTAAAAGGCTTCTATCCCCCAGACATTTA
TGTGGAGTGGCAGATGAACGGGCAGCCACAGGAAAACTACAAGAACACTC
CACCTACGATGGACACAGATGGGAGTTACTTCCTCTACAGCAAGCTCAAT
GTGAAGAAGGAAAAATGGCAGCAGGGAAACACGTTCACGTGTTCTGTGCT
GCATGAAGGCCTGCACAACCACCATACTGAGAAGAGTCTCTCCCACTCTC
CGGGTAAATGACCCGCGGCCGCGACTCTAGATCATAATCAGCCATACCAC
ATTTGTAGAGGTTTTACTTGCTTTAAAAAACCTCCCACACCTCCCCCTGA
ACCTGAAACATAAAATGAATGCAATTGTTGTTGTTAACTTGTTTATTGCA
GCTTATAATGGTTACAAATAAAGCAATAGCATCACAAATTTCACAAATAA
AGCATTTTTTCACTGCATTCTAGTTGTGGTTTGTCCAAACTCATCAATG
TATCTTAAGGCGTAAATTGTAAGCGTTAATATTTTGTTAAAATTCGCGTT
AAATTTTTGTTAAATCAGCTCATTTTTTAACCAATAGGCCGAAATCGGCA
AAATCCCTTATAAATCAAAAGAATAGACCGAGATAGGGTTGAGTGTTGTT
CCAGTTTGGAACAAGAGTCCACTATTAAAGAACGTGGACTCCAACGTCAA
AGGGCGAAAAACCGTCTATCAGGGCGATGGCCCACTACGTGAACCATCAC
CCTAATCAAGTTTTTTGGGGTCGAGGTGCCGTAAAGCACTAAATCGGAAC
CCTAAAGGGAGCCCCCGATTTAGAGCTTGACGGGGAAAGCCGGCGAACGT
GGCGAGAAAGGAAGGGAAGAAAGCGAAAGGAGCGGGCGCTAGGGCGCTGG
CAAGTGTAGCGGTCACGCTGCGCGTAACCACCACACCCGCCGCGCTTAAT
GCGCCGCTACAGGGCGCGTCagatctTAGTTATTAATAGTAATCAATTAC
GGGGTCATTAGTTCATAGCCCATATATGGAGTTCCGCGTTACATAACTTA
CGGTAAATGGCCCGCCTGGCTGACCGCCCAACGACCCCCGCCCATTGACG
TCAATAATGACGTATGTTCCCATAGTAACGCCAATAGGGACTTTCCATTG
ACGTCAATGGGTGGAGTATTTACGGTAAACTGCCCACTTGGCAGTACATC
AAGTGTATCATATGCCAAGTACGCCCCCTATTGACGTCAATGACGGTAAA
TGGCCCGCCTGGCATTATGCCCAGTACATGACCTTATGGGACTTTCCTAC
TTGGCAGTACATCTACGTATTAGTCATCGCTATTACCATGGTGATGCGGT
TTTGGCAGTACATCAATGGGCGTGGATAGCGGTTTGACTCACGGGGATTT
CCAAGTCTCCACCCCATTGACGTCAATGGGAGTTTGTTTTGGCACCAAAA
TCAACGGGACTTTCCAAAATGTCGTAACAACTCCGCCCCATTGACGCAAA
TGGGCGGTAGGCGTGTACGGTGGGAGGTCTATATAAGCAGAGCTGGTTTA
GTGAACCGTCAGATCCGCTAGCGCTACCGGACTCAGATCCCCCCCCCCCC
C
```

A Gene Joining Double-Stranded DNA Fragment

The rat κ chain gene joining double-stranded DNA fragment (SEQ ID NO: 64) consists of a rat κ chain constant region (1-325), a joining sequence II (1-53), a polyA added signal (507-513), a CMV promoter (1038-1633), and a joining sequence 1 (1634-1662).

```
GGGCTGATGCTGCACCAACTGTATCTATCTTCCCACCATCCACGGAACAG
TTAGCAACTGGAGGTGCCTCAGTCGTGTGCCTCATGAACAACTTCTATCC
CAGAGACATCAGTGTCAAGTGGAAGATTGATGGCACTGAACGACGAGATG
GTGTCCTGGACAGTGTTACTGATCAGGACAGCAAAGACAGCACGTACAGC
ATGAGCAGCACCCTCTCGTTGACCAAGGCTGACTATGAAAGTCATAACCT
CTATACCTGTGAGGTTGTTCATAAGACATCATCCTCACCCGTCGTCAAGA
GCTTCAACAGGAATGAGTGTTAGACGCGGCCGCGACTCTAGATCATAATC
AGCCATACCACATTTGTAGAGGTTTTACTTGCTTTAAAAAACCTCCCACA
CCTCCCCCTGAACCTGAAACATAAAATGAATGCAATTGTTGTTGTTAACT
TGTTTATTGCAGCTTATAATGGTTACAAATAAAGCAATAGCATCACAAAT
TTCACAAATAAAGCATTTTTTCACTGCATTCTAGTTGTGGTTTGTCCAA
ACTCATCAATGTATCTTAAGGCGTAAATTGTAAGCGTTAATATTTTGTTA
AAATTCGCGTTAAATTTTTGTTAAATCAGCTCATTTTTTAACCAATAGGC
```

```
                                              -continued
CGAAATCGGCAAAATCCCTTATAAATCAAAAGAATAGACCGAGATAGGGT

TGAGTGTTGTTCCAGTTTGGAACAAGAGTCCACTATTAAAGAACGTGGAC

TCCAACGTCAAAGGGCGAAAAACCGTCTATCAGGGCGATGGCCCACTACG

TGAACCATCACCCTAATCAAGTTTTTTGGGGTCGAGGTGCCGTAAAGCAC

TAAATCGGAACCCTAAAGGGAGCCCCCGATTTAGAGCTTGACGGGGAAAG

CCGGCGAACGTGGCGAGAAAGGAAGGGAAGAAAGCGAAAGGAGCGGGCGC

TAGGGCGCTGGCAAGTGTAGCGGTCACGCTGCGCGTAACCACCACACCCG

CCGCGCTTAATGCGCCGCTACAGGGCGCGTCagatctTAGTTATTAATAG

TAATCAATTACGGGGTCATTAGTTCATAGCCCATATATGGAGTTCCGCGT

TACATAACTTACGGTAAATGGCCCGCCTGGCTGACCGCCCAACGACCCCC

GCCCATTGACGTCAATAATGACGTATGTTCCCATAGTAACGCCAATAGGG

ACTTTCCATTGACGTCAATGGGTGGAGTATTTACGGTAAACTGCCCACTT

GGCAGTACATCAAGTGTATCATATGCCAAGTACGCCCCCTATTGACGTCA

ATGACGGTAAATGGCCCGCCTGGCATTATGCCCAGTACATGACCTTATGG

GACTTTCCTACTTGGCAGTACATCTACGTATTAGTCATCGCTATTACCAT

GGTGATGCGGTTTTGGCAGTACATCAATGGGCGTGGATAGCGGTTTGACT

CACGGGGATTTCCAAGTCTCCACCCCATTGACGTCAATGGGAGTTTGTTT

TGGCACCAAAATCAACGGGACTTTCCAAAATGTCGTAACAACTCCGCCCC

ATTGACGCAAATGGGCGGTAGGCGTGTACGGTGGGAGGTCTATATAAGCA

GAGCTGGTTTAGTGAACCGTCAGATCCGCTAGCGCTACCGGACTCAGATC ccccccccccc
```

Figure 4:
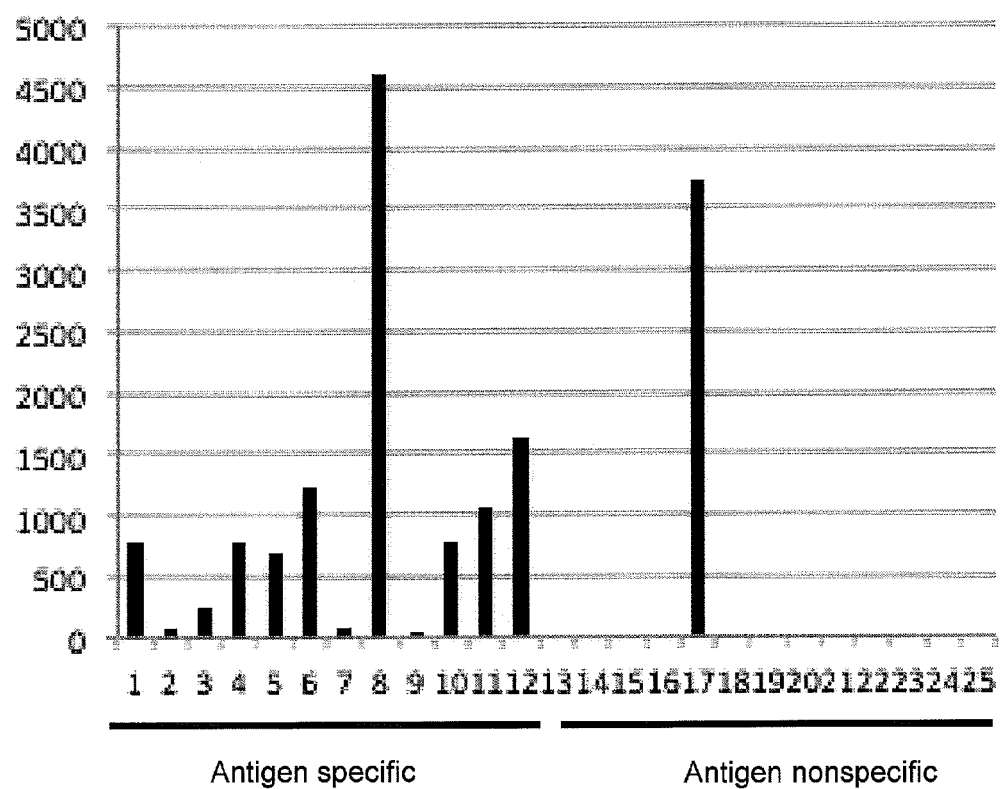
FIG. 4 Shows the results of Example 1. These are the results of determining by the ELISA method the GFP binding ability of recombinant antibodies obtained from antigen specific plasma cells (high) and nonspecific plasma cells (total). The y-axis denotes the GFP binding level of 1 ng of antibody. The numbers 1 to 12 denote recombinant antibodies prepared from the antigen specific plasma cell fraction, 13 to 24 denote recombinant antibodies prepared from the nonspecific plasma cell fraction, and 25 denotes a negative control.

The full lengths of the rat γ chain and κ chain gene expression units amplified in the above experiments were genetically introduced into 293FT cells and the cells were cultured for two days to bring about the secretion of recombinant rat antibodies in the cell culture. The ability to bind antigen of the recombinant rat monoclonal antibodies obtained from the antigen specific and nonspecific plasma cells was examined by the ELISA method (FIG. 4). As a result, the recombinant rat monoclonal antibodies obtained from antigen specific plasma cells exhibited strong binding ability to GFP in 9 out of 12 clones. By contrast, the recombinant rat monoclonal antibodies obtained from the total plasma cell fraction exhibited strong binding ability to GFP in only 1 out of 12 clones. Based on these results, based on just the operation of subjecting a lymphocyte suspension to the effects of labeled antigen and ER-tracker, it was clearly possible to identify antigen specific plasma cells and then highly efficiently prepare antigen specific rat monoclonal antibodies.

Example 2

Preparation of Anti-Human Insulin Guinea Pig Monoclonal Antibodies

Insulin binds to insulin receptors that are present on the surfaces of cells in the liver, muscle, and fatty tissue. It controls the uptake of glucose into cells, making it an important hormone playing a role in regulating energy metabolism within the body. Measurement of the insulin concentration in the blood is extremely important in dealing with pathological conditions such as diabetes and obesity. The structures of mammalian insulins exhibit high homology, with the exception of guinea pigs. Thus, it is difficult to prepare monoclonal antibodies using mice. For this reason, polyclonal antibodies obtained from guinea pig serum has come to be used to measure the concentration of human insulin in the blood. However, polyclonal antibodies present major differences in lots from different individual immune animals, making it difficult to maintain constant quality. The development of anti-human insulin guinea pig monoclonal antibodies is needed. Accordingly, the present invention was employed to prepare anti-human insulin guinea pig monoclonal antibodies.

[Materials and Methodology]

Female six-week-old guinea pigs were employed as the immune animals. The antigen was human insulin. In immunization, 50 μg of human insulin were injected intramuscularly four times at one-month intervals on both sides of the tail of the guinea pigs. Once immunity had been established, the iliac lymph nodes were collected from the guinea pigs. The human insulin was fluorescence labeled with Alexafluor 594 and purified by gel filtration.

[Results]

Lymphocytes from the iliac lymph nodes were suspended in a 0.5% PBS bovine serum albumin solution, after which fluorescent dye labeled anti-guinea pig IgG antibodies were added and the mixture was stirred for 30 minutes at 4° C. The cells were centrifuged and suspended in DMEM medium. To this was added ER-tracker (1 μm) and the mixture was left standing for 5 minutes at room temperature to stain the endoplasmic reticulum. The cells were then observed under a fluorescence microscope. As a result, the expression of IgG was observed on the surface of the strongly ER-tracker positive plasma cells (FIG. 5).

Next, the membrane-bound IgG was subjected to the action of fluorescence-labeled antigen in an attempt to identify antigen specific plasma cells. The ilium guinea pig lymphocyte suspension was stained with Alexafluor 594 labeled insulin and ER-tracker and analyzed with a flow cytometer. As a result, as shown in FIG. 6, labeled insulin positive and strongly ER-tracker positive cell groups were present (R1 in FIG. 6). These were adopted as an antigen specific plasma cell fraction.

cDNA Synthesis cDNA was synthesized and the immunoglobulin gene was amplified in accordance with the methods described in "Reaction device, reaction method and method of synthesizing cDNA" (WO2009/091048).

Individual guinea pig plasma cells that had been separated with a cell sorter were added to 3 μL of cell lysate (100 mM TrisHCl (pH 7.5), 500 mM LiCl, 1% lithium dodecylsulfate (LiDS), and 5 mM dithiothreitol) containing 3 μg of magnetic beads (Dynabeads) bonded to oligo-dT25. The mRNA in the cells was caused to bind to the magnetic beads. Next, the magnetic beads were washed once with 3 μL of mRNA cleaning solution A (10 mM TrisHCl (pH 7.5), 0.15 M LiCl, and 0.1% LiDS) followed by 3 μL of mRNA cleaning solution B (75 mM KCl, 3 mM MgCl2, 0.1% TritonX, 0.5 mM dNTP, mM DTT, and 2 units of RNase inhibitor). cDNA was then synthesized. After washing, to the beads were added 3 μL of cDNA synthesis solution (50 mM TrisHCl (pH 8.3), 75 mM KCl, 3 mM MgCl2, 0.1% TritonX-100, 0.5 mM dNTP, 5 mM DTT, 2 units of RNase inhibitor, and 10 units of SuperScriptIII Reversetranscriptase (Invitrogen) and the mixture was reacted for one hour at 37° C. Next, the magnetic beads were washed with 3 μL of 3' tailing cleaning solution (50 mM potassium phosphate (pH 7.0), 0.5 mM dGTP, 0.1% TritonX-100, and 4 mM magnesium chloride).

An additional 3 μL of 3' tailing reaction solution (50 mM potassium phosphate (pH 7.0), 0.5 mM dGTP, 0.1% TritonX-100, 4 mM magnesium chloride, and 10 units of terminal deoxynucleotidyl transferase) were added and the mixture was reacted for 30 minutes at 37° C.

Amplification of Guinea Pig γ, κ, and λ Chain Variable Region Gene Fragments

Magnetic beads were washed with 3 μL of TE solution (10 mM TrisHCl (pH 7.5), 1 mM EDTA, and 0.1% TritonX-100) after which the 5'-RACE PCR method was employed to amplify the human immunoglobulin γ chain and κ chain genes. In the first round PCR reaction, 25 μL of PCR reaction solution (containing 0.2 μM of each primer, 0.2 mM of dNTP, and 1 unit of TakaraBio PrimeSTAR heat-resistant DNA polymerase) was added to the magnetic beads and 35 cycles of reactions for 30 seconds at 94° C. and 40 seconds at 68° C. were conducted. The primer (a) employed was annealed to the poly-G added to the 3' end of the cDNA by TdT. Primer sequence (i) was derived from the constant region of the guinea pig immunoglobulin γ chain gene. Primer sequence (j) was derived from the constant region of the guinea pig immunoglobulin κ chain gene. And primer sequence (k) was derived from the constant region of the guinea pig immunoglobulin λ chain gene.

Figure 7:
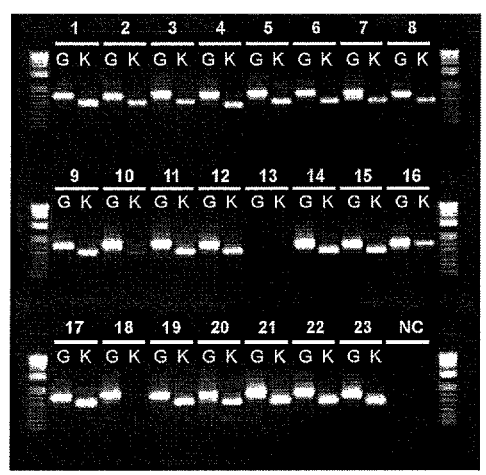
FIG. 7 Shows the results of Example 2. γ and κ chain variable region gene fragments from individual plasma cells separated from antigen specific plasma cell fractions were amplified. The 1% agarose gel electrophoresis photographs of classic amplification products are shown. G shows a guinea pig γ variable region gene fragment and K shows a κ chain variable region gene fragment.

After the reaction, 225 μL of water was added to the PCR solution and 1 μL of the 10-fold diluted solution was employed as template. Primers (d) and (l) were employed and an amplification reaction of the variable region of the rat [sic: guinea pig] immunoglobulin γ chain gene was conducted under the same conditions as in the first round PCR. Similarly, primers (d) and (m) were employed to conduct an amplification reaction of the variable region of the rat [sic: guinea pig] immunoglobulin κ chain gene. Similarly, primers (d) and (n) were employed to conduct an amplification reaction of the variable region of the rat [sic: guinea pig] immunoglobulin λ chain gene (FIG. 7).

The primers employed were:

```
First round PCR γ chain amplification
antisense primer
                                    (SEQ ID NO: 65)
5-GGTGCTGCTGGCCGGGTGGGCTACATTGCA-3 (i)

First round PCR κ chain amplification
antisense primer
                                    (SEQ ID NO: 66)
5-CAGAGCCATCCACCTTCCACTTGACGG-3 (j)

First round PCR λ chain amplification
antisense primer
                                    (SEQ ID NO: 67)
5-CTGCTGGCCATGTATTTGTTGTCGCTCTG-3 (k)

Second round PCR γ chain amplification
sense primer
                                    (SEQ ID NO: 68)
5-CTGAAGGACGGCCGGGAAGGTGTGCAC-3 (l)

Second round PCR κ chain amplification
antisense primer
                                    (SEQ ID NO: 69)
5-GGAAGAGGGAGATAGTTGGCTTCTGCACACTC-3 (m)

Second round PCR λ chain amplification
antisense primer
                                    (SEQ ID NO: 70)
5-AGAAGGAATTCAGGAGACACACCACTGT-3 (n)
```

Since the structure of the antibody genes of the guinea pig has not yet been clarified, cDNA prepared from guinea pig spleen cells was employed to clone the guinea pig γ chain gene constant region, κ chain gene constant region, and λ chain gene constant region. The base sequences of these regions were then determined. Specifically, guinea pig spleen cells were added to 3 μL of cell lysate (100 mM TrisHCl (pH 7.5), 500 mM LiCl, 1% lithium dodecylsulfate (LIDS), and 5 mM dithiothreitol) containing 3 μg of magnetic beads (Dynabeads) bonded to oligo-dT25. The mRNA in the cells was caused to bind to the magnetic beads. Next, the magnetic beads were washed once with 3 μL of mRNA cleaning solution A (10 mM TrisHCl (pH 7.5), 0.15 M LiCl, and 0.1% LiDS) followed by 3 μL of mRNA cleaning solution B (75 mM KCl, 3 mM MgCl2, 0.1% TritonX, 0.5 mM dNTP, 5 mM DTT, and 2 units of RNase inhibitor). cDNA was then synthesized. After washing, to the beads were added 3 μL of cDNA synthesis solution (50 mM TrisHCl (pH 8.3), 75 mM KCl, 3 mM MgCl2, 0.1% TritonX-100, 0.5 mM dNTP, 5 mM DTT, 2 units of RNase inhibitor, and 10 units of SuperScriptIII Reversetranscriptase (Invitrogen) and the mixture was reacted for one hour at 37° C.

The cDNA prepared above was employed as template. Primers (o) and (p) were used to amplify the γ chain constant region, primers (q) and (r) to amplify the κ constant region, and primers (s) and (t) to amplify the λ chain constant region. The amplified DNA fragments were inserted at the XhoI/NotI site of the pBluescript SK vector, and the base sequences thereof were determined.

```
                                                       (SEQ ID NO: 71)
(o)  5-AGAGACTCGAGTGCCTGGTCAAGGGCTACTTCCCTGA-3

(SEQ ID NO: 72)
(p)  5-GAGAGAGCGGCCGCTCATTTACCCGGAGACCGGGAGAT-3

(SEQ ID NO: 73)
(q)  5-AGAGACTCGAGGGGACCAAGCTGGAAATCAAACGGA-3

(SEQ ID NO: 74)
(r)  5-GAGAGAGCGGCCGCCTAGCACTCGCTCCTGTTGATGGTCT-3

(SEQ ID NO: 75)
(s)  5-AGAGACTCGAGGAGGAGCTCCAGGACAACAAGGC-3

(SEQ ID NO: 76)
(t)  5-GAGAGAGCGGCCGCTAAGAACACTCTGACGGGCCAC-3
```

-continued

γ Chain constant region sequence
(SEQ ID NO: 1)
TGCCTGGTCAAGGGCTACTTCCCTGAGCCGGTGACTGTGAAATGGAACTCAGGGG

CCCTGACCAGTGGAGTGCACACCTTCCCGGCCGTCCTTCAGTCAGGCCTGTACTC

ACTCACCAGCATGGTAACTGTGCCCTCCAGCCAGAAGAAGGCCACCTGCAATGTA

GCCCACCCGGCCAGCAGCACCAAGGTGGACAAGACTGTTGAGCCTATTCGAACTC

CTCAACCCAACCCGTGTACATGTCCCAAGTGCCCACCTCCTGAAAACCTGGGTGG

ACCATCTGTCTTCATCTTTCCCCCGAAGCCCAAGGACACGCTCATGATCTCCCTGA

CCCCTAGGGTCACATGTGTGGTGGTAGATGTGAGCCAAGATGAGCCTGAAGTCCA

GTTCACATGGTTCGTGGACAACAAACCGGTCGGCAATGCTGAGACAAAGCCCCGA

GTGGAGCAATACAACACGACATTCCGCGTGGAAAGTGTCCTCCCCATCCAGCACC

AGGACTGGCTGAGGGGCAAGGAATTCAAGTGCAAGGTCTACAACAAAGCCCTGCC

AGCCCCCATAGAGAAGACCATCTCCAAAACCAAAGGGGCTCCCCGCATGCCAGAT

GTGTACACCCTTCCCCCGTCCCGAGACGAGCTATCCAAGAGCAAAGTCAGTGTGA

CCTGCCTGATCATCAACTTCTTTCCTGCCGACATCCACGTGGAGTGGGCCAGCAAT

AGGGTTCCAGTGAGTGAGAAGGAATACAAGAACACCCCACCCATTGAGGACGCTG

ACGGGTCCTACTTCCTCTACAGCAAGCTCACTGTGGATAAGAGCGCGTGGGATCA

GGGAACCGTCTACACCTGCTCCGTGATGCATGAAGCCCTGCACAATCATGTCACT

CAGAAGGCCATCTCCCGGTCTCCGGGTAA

γ Chain constant region amino acid sequence
(SEQ ID NO: 4)
CLVKGYFPEPVTVKWNSGALTSGVHTFPAVLQSGLYSLTSMVTVPSSQKKATCNVAH

PASSTKVDKTVEPIRTPQPNPCTCPKCPPPENLGGPSVFIFPPKPKDTLMISLTPRVTC

VVVDVSQDEPEVQFTWFVDNKPVGNAETKPRVEQYNTTFRVESVLPIQHQDWLRGKE

FKCKVYNKALPAPIEKTISKTKGAPRMPDVYTLPPSRDELSKSKVSVTCLIINFFPADIHV

EWASNRVPVSEKEYKNTPPIEDADGSYFLYSKLTVDKSAWDQGTVYTCSVMHEALHN

HVTQKAISRSPG

κ Chain constant region sequence
(SEQ ID NO: 2)
GGGACCAAGCTGGAAATCAAACGGAGTGTGCAGAAGCCAACTATCTCCCTCTTCC

CTCCATCATCTGAGGAGGTGACAGCTGGAAGTGCCTCAGTTGTGTGCTTCATTAAT

AGCTTCTATCCAAGAGACATCACCGTCAAGTGGAAGGTGGATGGCTCTGAACGCT

CACAAGGCATCCTGAACAGTTACACAGATCAGGACAGCAAGGACAACACCTACAG

CCTCAGTAGCACCCTGGCGCTGACGGCTTCAGAGTACAATCAGCATGAGAGGTAC

ACCTGCGAGGTCTCCCACGCTGGCCTGACCTCACCCGCTGCCAAGACCATCAACA

GGAGCGAGTGCTAG

κChain constant region amino acid sequence
(SEQ ID NO: 5)
GTKLEIKRSVQKPTISLFPPSSEEVTAGSASVVCFINSFYPRDITVKWKVDGSERSQGIL

NSYTDQDSKDNTYSLSSTLALTASEYNQHERYTCEVSHAGLTSPAAKTINRSEC

λ Chain constant region sequence
(SEQ ID NO: 3)
GAGGAGCTCCAGGACAACAAGGCCACAGTGGTGTGTCTCCTGAATTCCTTCTACC

CCGGCTCTGTGAATGTCAGCTGGAAGGCAGATGGCACCACCATCAACCAGGGCGT

GCAGACCACACAGCCTGCCAAACAGAGCGACAACAAATACATGGCCAGCAGCTAC

-continued
CTGACACTGACTCCCGACCAGTGGAGGTCTCACCAGAGAATCAGCTGCCAGGTCA

AACACGAGGCAGGCAATGTGGAGAAGAGTTTGGCCCCGTCAGAGTGTTCTTAA

λ Chain constant region amino acid sequence
(SEQ ID NO: 6)
EELQDNKATVVCLLNSFYPGSVNVSWKADGTTINQGVQTTQPAKQSDNKYMASSYLT

LTPDQWRSHQRISCQVKHEAGNVEKSLAPSECS

The guinea pig γ chain gene, κ chain gene, and λ chain gene expression units were prepared in accordance with the methods described in "Method for Specifically Producing a Joined DNA Fragment Comprising a Sequence Derived from a Target Gene" (WO2011/027808).

That is, 2 units of terminal deoxynucleotidyl transferase were added to 1 μL of each PCR product that had been amplified by the 5'-RACE-PCR method, a reaction was conducted for 30 minutes at 37° C., and heating was subsequently conducted for 5 minutes at 94° C. to halt the enzymatic reaction.

To the 3' end polynucleotide addition guinea pig γ chain gene solution prepared above were added 10 ng of guinea pig γ chain gene joining double-stranded DNA fragments, 10 pmol of primer, and 10 nmol of dNTP. Five cycles of reactions for 40 seconds at 94° C. and for 4 minutes at 70° C. followed by 30 cycles of reaction for 40 seconds at 94° C., 40 seconds at 60° C., and 4 minutes at 72° C. were then conducted in 25 μL of reaction solution employing Takara-Bio PrimeSTAR heat-resistant DNA polymerase to prepare guinea pig γ chain gene expression units.

Similarly, guinea pig κ chain gene joining double-stranded DNA fragments were added to a guinea pig κ chain gene solution and a reaction was conducted to prepared guinea pig κ chain gene expression units. Similarly, guinea pig λ chain gene joining double-stranded DNA fragments were added to a guinea pig λ chain gene solution and a reaction was conducted to prepared guinea pig λ chain gene expression units.

Primers (g) and (h) were employed in the expression unit amplification.

Figure 8:
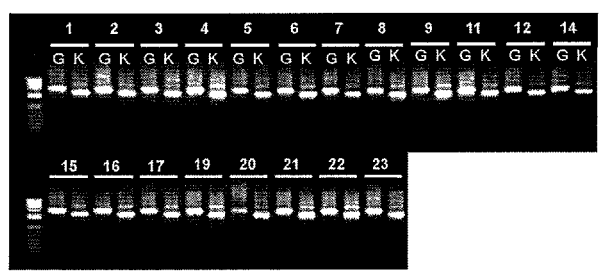
FIG. 8 Shows the results of Example 2. Linearized γ chain and κ chain expression units were obtained by joining the amplified guinea pig γ and κ chain variable region gene fragments to double-stranded DNA cassette fragments, and 1% agarose gel electrophoresis photographs were taken of these units. G denotes the linearized γ chain expression unit and K denotes the κ chain expression unit.

After the reaction, 1 μL of each PCR solution was measured out and the conversion to the expression units of κ and γ chain immunoglobulin gene fragments was confirmed by the agarose gel electrophoresis method (see FIG. 8).

The guinea pig γ chain gene joining double-stranded DNA fragment (SEQ ID NO: 77) consists of a guinea pig γ chain constant region (1-911), a joining sequence II (1-96), a polyA addition signal (912-1118), a CMV promoter (1628-2093), and a joining sequence 1 (2094-2123).

TGCCTGGTCAAGGGCTACTTCCCTGAGCCGGTGACTGTGAAATGGAACTC

AGGGGCCCTGACCAGTGGAGTGCACACCTTCCCGGCCGTCCTTCAGTCAG

GCCTGTACTCACTCACCAGCATGGTAACTGTGCCCTCCAGCCAGAAGAAG

GCCACCTGCAATGTAGCCCACCCGGCCAGCAGCACCAAGGTGGACAAGAC

TGTTGAGCCTATTCGAACTCCTCAACCCAACCCGTGTACATGTCCCAAGT

GCCCACCTCCTGAAAACCTGGGTGGACCATCTGTCTTCATCTTTCCCCCG

AAGCCCAAGGACACGCTCATGATCTCCCTGACCCCTAGGGTCACATGTGT

GGTGGTAGATGTGAGCCAAGATGAGCCTGAAGTCCAGTTCACATGGTTCG

-continued
TGGACAACAAACCGGTCGGCAATGCTGAGACAAAGCCCCGAGTGGAGCAA

TACAACACGACATTCCGCGTGGAAAGTGTCCTCCCCATCCAGCACCAGGA

CTGGCTGAGGGGCAAGGAATTCAAGTGCAAGGTCTACAACAAAGCCCTGC

CAGCCCCCATAGAGAAGACCATCTCCAAAACCAAAGGGGCTCCCCGCATG

CCAGATGTGTACACCCTTCCCCCGTCCCGAGACGAGCTATCCAAGAGCAA

AGTCAGTGTGACCTGCCTGATCATCAACTTCTTTCCTGCCGACATCCACG

TGGAGTGGGCCAGCAATAGGGTTCCAGTGAGTGAGAAGGAATACAAGAAC

ACCCCACCCATTGAGGACGCTGACGGGTCCTACTTCCTCTACAGCAAGCT

CACTGTGGATAAGAGCGCGTGGGATCAGGGAACCGTCTACACCTGCTCCG

TGATGCATGAAGCCCTGCACAATCATGTCACTCAGAAGGCCATCTCCCGG

TCTCCGGGTAAATGAGCGGCCGCGACTCTAGATCATAATCAGCCATACCA

CATTTGTAGAGGTTTTACTTGCTTTAAAAAACCTCCCACACCTCCCCCTG

AACCTGAAACATAAAATGAATGCAATTGTTGTTGTTAACTTGTTTATTGC

AGCTTATAATGGTTACAAATAAAGCAATAGCATCACAAATTTCACAAATA

AAGCATTTTTTTCACTGCATTCTAGTTGTGGTTTGTCCAAACTCATCAAT

GTATCTAAGGCGTAAATTGTAAGCGTTAATATTTTGTTAAAATTCGCGT

TAAATTTTTGTTAAATCAGCTCATTTTTTAACCAATAGGCCGAAATCGGC

AAAATCCCTTATAAATCAAAAGAATAGACCGAGATAGGGTTGAGTGTTGT

TCCAGTTTGGAACAAGAGTCCACTATTAAAGAACGTGGACTCCAACGTCA

AAGGGCGAAAAACCGTCTATCAGGGCGATGGCCCACTACGTGAACCATCA

CCCTAATCAAGTTTTTTGGGGTCGAGGTGCCGTAAAGCACTAAATCGGAA

CCCTAAAGGGAGCCCCCGATTTAGAGCTTGACGGGGAAAGCCGGCGAATA

GTTATTAATAGTAATCAATTACGGGGTCATTAGTTCATAGCCCATATATG

GAGTTCCGCGTTACATAACTTACGGTAAATGGCCCGCCTGGCTGACCGCC

CAACGACCCCCGCCCATTGACGTCAATAATGACGTATGTTCCCATAGTAA

CGCCAATAGGGACTTTCCATTGACGTCAATGGGTGGAGTATTTACGGTAA

ACTGCCCACTTGGCAGTACATCAAGTGTATCATATGCCAAGTACGCCCCC

TATTGACGTCAATGACGGTAAATGGCCCGCCTGGCATTATGCCCAGTACA

TGACCTTATGGGACTTTCCTACTTGGCAGTACATCTACGTATTAGTCATC

GCTATTACCATGGTGATGCGGTTTTGGCAGTACATCAATGGGCGTGGATA

GCGGTTTGACTCACGGGGATTTCCAAGTCTCCACCCCATTGACGTCAATG

GGAGTTTGTTTTGGCACCAAAATCAACGGGACTTTCCAAAATGTCGTAAC

AACTCCGCCCCATTGACGCAAATGGGCGGTAGGCGTGTACGGTGGGAGGT

The guinea pig κ chain gene joining double-stranded DNA fragment (SEQ ID NO: 78) consists of a guinea pig κ chain constant region (1-345), a joining sequence II (1-55), a polyA addition signal (346-548), a CMV promoter (1058-1652), and a joining sequence 1 (1653-1682).

GGGACCAAGCTGGAAATCAAACGGAGTGTGCAGAAGCCAACTATCTCCCT
CTTCCCTCCATCATCTGAGGAGGTGACAGCTGGAAGTGCCTCAGTTGTGT
GCTTCATTAATAGCTTCTATCCAAGAGACATCACCGTCAAGTGGAAGGTG
GATGGCTCTGAACGCTCACAAGGCATCCTGAACAGTTACACAGATCAGGA
CAGCAAGGACAACACCTACAGCCTCAGTAGCACCCTGGCGCTGACGGCTT
CAGAGTACAATCAGCATGAGAGGTACACCTGCGAGGTCTCCCACGCTGGC
CTGACCTCACCCGCTGCCAAGACCATCAACAGGAGCGAGTGCTAGGCGGC
CGCGACTCTAGATCATAATCAGCCATACCACATTTGTAGAGGTTTTACTT
GCTTTAAAAAACCTCCCACACCTCCCCCTGAACCTGAAACATAAAATGAA
TGCAATTGTTGTTGTTAACTTGTTTATTGCAGCTTATAATGGTTACAAAT
AAAGCAATAGCATCACAAATTTCACAAATAAAGCATTTTTTTCACTGCAT
TCTAGTTGTGGTTTGTCCAAACTCATCAATGTATCTTAAGGCGTAAATTG
TAAGCGTTAATATTTTGTTAAAATTCGCGTTAAATTTTTGTTAAATCAGC
TCATTTTTTAACCAATAGGCCGAAATCGGCAAAATCCCTTATAAATCAAA
AGAATAGACCGAGATAGGGTTGAGTGTTGTTCCAGTTTGGAACAAGAGTC
CACTATTAAAGAACGTGGACTCCAACGTCAAAGGGCGAAAAACCGTCTAT
CAGGGCGATGGCCCACTACGTGAACCATCACCCTAATCAAGTTTTTGGG
GTCGAGGTGCCGTAAAGCACTAAATCGGAACCCTAAAGGGAGCCCCCGAT
TTAGAGCTTGACGGGGAAAGCCGGCGAACGTGGCGAGAAAGGAAGGGAAG
AAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGT
CagatctTAGTTATTAATAGTAATCAATTACGGGGTCATTAGTTCATAGC
CCATATATGGAGTTCCGCGTTACATAACTTACGGTAAATGGCCCGCCTGG
CTGACCGCCCAACGACCCCCGCCCATTGACGTCAATAATGACGTATGTTC
CCATAGTAACGCCAATAGGGACTTTCCATTGACGTCAATGGGTGGAGTAT
TTACGGTAAACTGCCCACTTGGCAGTACATCAAGTGTATCATATGCCAAG
TACGCCCCCTATTGACGTCAATGACGGTAAATGGCCCGCCTGGCATTATG
CCCAGTACATGACCTTATGGGACTTTCCTACTTGGCAGTACATCTACGTA
TTAGTCATCGCTATTACCATGGTGATGCGGTTTTGGCAGTACATCAATGG
GCGTGGATAGCGGTTTGACTCACGGGGATTTCCAAGTCTCCACCCCATTG
ACGTCAATGGGAGTTTGTTTTGGCACCAAAATCAACGGGACTTTCCAAAA
TGTCGTAACAACTCCGCCCCATTGACGCAAATGGGCGGTAGGCGTGTACG
GTGGGAGGTCTATATAAGCAGAGCTGGTTTAGTGAACCGTCAGATCCGCT
AGCGCTACCGGACTCAGATCCCCCCCCCCCCC The guinea pig λ chain gene joining double-stranded DNA fragment (SEQ ID NO: 79) consists of a guinea pig λ chain constant region (1-272), a joining sequence II (1-52), a polyA addition signal (53-410), a CMV promoter (985-1579), and a joining sequence 1 (1580-1609).

Figure 9:
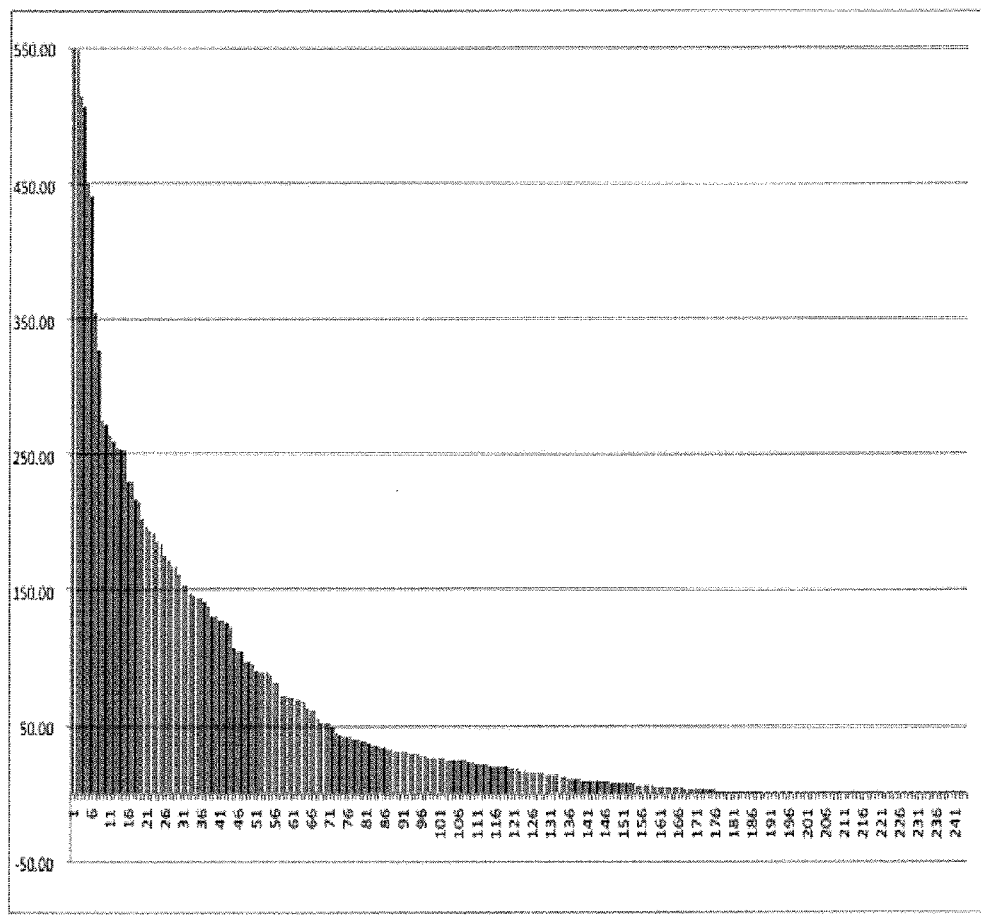
FIG. 9 Shows the results of Example 2. Linearized γ chain and κ chain or λ chain expression units were introduced into 293FT cells to show how recombinant antibodies were secreted in medium bound to human insulin. The x-axis denotes the capacity to bind human insulin per μg of recombinant antibody.

GAGGAGCTCCAGGACAACAAGGCCACAGTGGTGTGTCTCCTGAATTCCTT
CTACCCCGGCTCTGTGAATGTCAGCTGGAAGGCAGATGGCACCACCATCA
ACCAGGGCGTGCAGACCACACAGCCTGCCAAACAGAGCGACAACAAATAC
ATGGCCAGCAGCTACCTGACACTGACTCCCGACCAGTGGAGGTCTCACCA
GAGAATCAGCTGCCAGGTCAAACACGAGGCAGGCAATGTGGAGAAGAGTT
TGGCCCCGTCAGAGTGTTCTTAGCGGCCGCGACTCTAGATCATAATCAGC
CATACCACATTTGTAGAGGTTTTACTTGCTTTAAAAAACCTCCCACACCT
CCCCCTGAACCTGAAACATAAAATGAATGCAATTGTTGTTGTTAACTTGT
TTATTGCAGCTTATAATGGTTACAAATAAAGCAATAGCATCACAAATTTC
ACAAATAAAGCATTTTTTTCACTGCATTCTAGTTGTGGTTTGTCCAAACT
CATCAATGTATCTTAAGGCGTAAATTGTAAGCGTTAATATTTTGTTAAAA
TTCGCGTTAAATTTTTGTTAAATCAGCTCATTTTTTAACCAATAGGCCGA
AATCGGCAAAATCCCTTATAAATCAAAAGAATAGACCGAGATAGGGTTGA
GTGTTGTTCCAGTTTGGAACAAGAGTCCACTATTAAAGAACGTGGACTCC
AACGTCAAAGGGCGAAAAACCGTCTATCAGGGCGATGGCCCACTACGTGA
ACCATCACCCTAATCAAGTTTTTTGGGGTCGAGGTGCCGTAAAGCACTAA
ATCGGAACCCTAAAGGGAGCCCCCGATTTAGAGCTTGACGGGGAAAGCCG
GCGAACGTGGCGAGAAAGGAAGGGAAGAAAGCGAAAGGAGCGGGCGCTAG
GGCGCTGGCAAGTGTAGCGGTCACGCTGCGCGTAACCACCACACCCGCCG
CGCTTAATGCGCCGCTACAGGGCGCGTCagatctTAGTTATTAATAGTAA
TCAATTACGGGGTCATTAGTTCATAGCCCATATATGGAGTTCCGCGTTAC
ATAACTTACGGTAAATGGCCCGCCTGGCTGACCGCCCAACGACCCCCGCC
CATTGACGTCAATAATGACGTATGTTCCCATAGTAACGCCAATAGGGACT
TTCCATTGACGTCAATGGGTGGAGTATTTACGGTAAACTGCCCACTTGGC
AGTACATCAAGTGTATCATATGCCAAGTACGCCCCCTATTGACGTCAATG
ACGGTAAATGGCCCGCCTGGCATTATGCCCAGTACATGACCTTATGGGAC
TTTCCTACTTGGCAGTACATCTACGTATTAGTCATCGCTATTACCATGGT
GATGCGGTTTTGGCAGTACATCAATGGGCGTGGATAGCGGTTTGACTCAC
GGGGATTTCCAAGTCTCCACCCCATTGACGTCAATGGGAGTTTGTTTTGG
CACCAAAATCAACGGGACTTTCCAAAATGTCGTAACAACTCCGCCCCATT
GACGCAAATGGGCGGTAGGCGTGTACGGTGGGAGGTCTATATAAGCAGAG
CTGGTTTAGTGAACCGTCAGATCCGCTAGCGCTACCGGACTCAGATCCCC
CCCCCCCC The full lengths of the guinea pig γ chain, κ chain, and λ chain gene expression units amplified in the above experiments were genetically introduced into 293FT cells and the cells were cultured for two days to bring about the secretion of recombinant guinea pig antibodies in the cell culture. The ability to bind human insulin of the recombinant guinea pig monoclonal antibodies obtained from the antigen specific and nonspecific plasma cells was examined by the ELISA method (FIG. 9). As a result, of 241 types of the monoclonal antibodies obtained from the antigen specific plasma cells, 146 clones exhibited a 10-fold insulin binding ability over the negative control and 77 clones exhibited a 50-fold strong binding ability over the negative control. Based on these results, it was clearly possible to identify antigen specific plasma cells and then highly efficiently prepare antigen specific monoclonal antibodies in guinea pigs by simply staining cells with labeled antibody and ER-tracker.

Twelve clones with particularly high ability to bind human insulin were selected from among the 241 types of the recombinant antibodies obtained and their base sequences were determined. The gene sequences of the γ chain constant regions of the guinea pig antibodies to human insulin obtained in this fashion are given in SEQ ID NOs: 7 to 18 in the SEQUENCE LISTING. The amino acid sequences of peptides of the γ chain variable regions of the guinea pig antibodies to human insulin are given in SEQ ID NOs: 19 to 30. The gene sequences of the κ chain variable regions of the guinea pig antibodies to human insulin are given in SEQ ID NOs: 31 to 42 in the SEQUENCE LISTING. The amino acid sequences of the peptides of the κ chain variable regions of the guinea pig antibodies to human insulin are given in SEQ ID NOs: 43 to 54.

The FR1, CDR1, FR2, CDR2, FR3, CDR3, and FR4 of the κ chain and γ chain constant and variable regions of the guinea pig antibodies to human insulin set forth above were determined using homology with the various human immunoglobulin variable regions. The amino acid sequences of the FR1 to 4 and CDR1 to 3 of the κ chains and γ chains of the 12 guinea pig monoclonal antibodies obtained are given in the tables below.

TABLE 1

| Sample No: | FR1 | CDR1 | FR2 |
|---|---|---|---|
| κ chains | | | |
| 1 | DIQLTQ-PASTSASVGDTVKISCRAS | QTINNY | LNWYQQKPGQAPKLLIY |
| 2 | DIQLTQ-PASTSASVGDTVKISCRTS | QTISSY | LNWYQQKPGQAPKLLIY |
| 3 | DIQLTQ-PASASASVGDTVKISCRVS | QSVSSY | LNWYQQKPGQAPKLLIY |
| 4 | DIQLTQ-PASASASVGDTVKISCRAS | QTISSY | LNWYQQKPGQAPTILIY |
| 5 | QIVLTQSPASLAASPGQKVTITCTAS | SSVNNNF | FHWYQQKPGASPTLLIY |
| 6 | DFVMTQSPASLSVTPGESTTIRCKSS | QSLLSRYNNKNN | LAWYQQKPGQSPKLLIY |
| 7 | QIVLTQSPASLTASPGEKVSITCTAS | SSISESY | LHWYQQKPGASPKLLIY |
| 8 | QIVLTQSPASLAASPGEKVTITCTAS | SSLINNY | LHWYQQKVGASPKLLIY |
| 9 | QIVLTQSPTSLAASPGEKVTITCTAN | SSISDSY | LHWYQQKPGASPKLLIY |
| 10 | QIVLTQSPASLAASPGEKVTITCTAS | STLIKNY | LHWYQQKPGTSPRLLIY |
| 11 | QIVLTQSPASLAASPGEKVTITCTAS | SNLINNY | LHWYQQKPGASPKLLIY |
| 12 | QIVLTQSPASLAASPGEKVTISCTAS | SSLINNY | LHWYQQRPGASPKLLIY |
| 13 | QIVLTQSPASLAASPGEKVTITCTAS | SSVNNNF | LHWYQQKPGASPKLVIY |
| 14 | DIQLTQ-PASASASVGDTLKISCRAS | QSIKNY | LNWYQQKPGQAPKLLIY |
| 15 | DTVMTQSPASLAVTPGERATIHCKSS | QSLLSSENNKNY | LDWYQHKPGQSPKLLIY |
| γ chains | | | |
| 1 | QMQVQESGPGLVKPSQTLFLTCSVS | GFSITTSGYA | WTWIRQPRGRTLELVGG |
| 2 | QMQLQESGPGLVKPSQTLFLTCSVS | GFSITTSGYG | WTWIRQPRGKTLELLGG |
| 3 | QMQLQESGPGLVKPSQTLFLTCSVS | GFSITTSGYG | WSWIRQARGKTLELMGG |
| 4 | QMQLQESGPGLVKPSQTLFLTCSVS | GFSITTSGYA | WTWIRQPRGKTLELMGG |
| 5 | QVQLQESGPGLVKPSETLSLTCKVS | GFSLMDYS | VSWIRQAPGEGLEWIGV |
| 6 | QMQLQESGPGLVKPSQTLFLSCSVS | EFSITTSGYG | WSWIRQSRGKTLEVMGE |
| 7 | EEQLVESGGGLVQPGGSLKLSCTAS | GMTLSNYA | MSWIRQAPGKGLEWISA |
| 8 | QVQLQESGPGLVKPSETLSLTCKVS | GFSLTGYP | VSWIRQTPGKGLELIGG |
| 9 | EGQLVESGGGLVQPGGSLKLSCMAS | GLTLSNYA | INWIRQAPGKGLEWISA |
| 10 | QVQLQESGPGLVKPSETLSLTCKVS | GFSLSGYP | VSWIRQTPGKGLELIGG |
| 11 | QVQLQESGPGLVKPSETLSLTCTVS | GFSLTGYS | VSWIRQTPGKGLELLGG |

TABLE 1-continued

| | | | |
|---|---|---|---|
| 12 | QVQLQESGPGLVKPSETLSLTCEVS | GFSLTGYS | VSWIRQTPEKGLELIGG |
| 13 | QVQLQESGPGLVKPSETLSLTCKVS | GFSLSGYS | VSWIRQAPGKGLEWIGA |
| 14 | QLQLQQSGPGLVKPSQTLFLTCSVS | GFSIATSGYG | WSWIRQARGKTLELMGG |
| 15 | EVQLVESGGDLVQPGGSLRLSCLAS | GFTFSRYG | MSWIRRAPGKGLEWISH |

| Sample No. | CDR2 | FR3 |
|---|---|---|
| κ chains | | |
| 1 | GTN | NLQSGIPSRFSGSGSGTDFTLIISSLRPEDFATYYC |
| 2 | GTN | NLQSGIPSRFSGSGSGTDFTLIISSLRPEDFATYYC |
| 3 | WAT | NLQSGIPSRFSGSGSGTDFTLTISSLKPEDFATYYC |
| 4 | GTN | NLQSGIPSRFSGSGSGTDFTLIISSLRPEDFATYYC |
| 5 | RTS | RLASGVPARFSGSGSGTSYSLTISSMEGEDVATYYC |
| 6 | WAS | TRNTGVPDRFSGSGSGTDFTLTISSVLAEDVADYYC |
| 7 | WAS | DLASGVPPRFSGSGSGTSFSLTISSMENEDVATYYC |
| 8 | RTS | RLASGVPARFSGSGSGTSYSLTISSMEGEDVATYYC |
| 9 | RTS | DVASGVPARFSGSGSGTSFSLTINSVEGEDAATYYC |
| 10 | RTS | KLASGVPARFSGSGSGTSYSLTISSMEGEDVATYYC |
| 11 | RTS | RLASGVPARFSGSGSGTSYSLTINNMEGEDVATYFC |
| 12 | RTS | RLASGVPARFSGSGSGTYYSLTISSMEGEDVATYYC |
| 13 | RTS | KLASGVPARFSGSGSGTSWSLTISSMEGEDVATYYC |
| 14 | WAT | NLQSGIPSRFSGSGSGTDFTLTISSLQPEDFSTYYC |
| 15 | LAS | TRAIGVPDRFSGSGSGTDFILTISPVQAEDVADYFC |
| γ chains | | |
| 1 | IAYNGGT | GYNPSIKSRISISRDTGKNQFSLQLNSVTEEDTATYYC |
| 2 | IAYNGGT | GYNPSIKSRISISRDIGKNQFSLQLNSVTEEDTATYYC |
| 3 | IAYNGGT | GYNPSIKSRISISRDTGKNQFSLQLNSVTEEDTGTYYC |
| 4 | IAYNGGT | GYNPSIKSRISISRDTGKSQFSLQLNSVTEEDTATYYC |
| 5 | IWSSGST | DYNSTFKSRVGMSRDTSKSQVSITLRSLSSEDTAVYYC |
| 6 | IAYNGAT | GYNPSIKSRISISRDTGKNQFSLHLNSVTEEDTATYYC |
| 7 | IVHSGSNT | RYIDSVKGRFTISRDNGRNTLYLQMSGLRPEDTAVYYC |
| 8 | IWSFGST | EYNSAFKSRVGISRDTSNNQVSLTLSSLSPEDTAVYYC |
| 9 | ISHSGSRT | NYAGSGKGRFTSSRDNGKNTIYLHMSSLRPEDTAVYYC |
| 10 | IWPFGGT | EHNSAFQSRVGISRDTSNNLVSGTQISMSPEDPSIFC |
| 11 | IWSFGST | EYNSAFKSRMGISRDTSKNQVSLTLSSLSPEDTAVYYC |
| 12 | IWNFGGT | EYNSAFKSRVGISRDTSKNQVSLTLRNVSPEDTAIYYC |
| 13 | IWATGST | DYDSAFKSRVGISRDISKSEVSLTLSSLSPEDSAVYYC |
| 14 | IAYNGGT | GYNPSIKSRISISRDTVKNQFSLQLNSVTDEDAATYYC |
| 15 | ISDSGSNT | YYPDSVKGRFTISRDNGKSLLYLQMSSLRPEDTAVYYC |

TABLE 1-continued

| Sample No. | CDR3 | FR4 | SEQ ID NO: |
|---|---|---|---|
| κ chains ||||
| 1 | QQSRSSPFT | FGGGTKLEIK | 43 |
| 2 | QQSNSSPFT | FGGGTKLEIK | 44 |
| 3 | QQSKTSPFT | FGGGTKLEIR | 45 |
| 4 | QQSRSSPFT | FGGGTKLEIK | 46 |
| 5 | LQSNSYT | FGAGTRLEIK | 47 |
| 6 | MQYYHFRT | FGAGTKLEIK | 48 |
| 7 | QQSTSYRT | FGAGTKLEIK | 49 |
| 8 | QESSSYYGT | FGAGTKLEIK | 50 |
| 9 | QQSTTY-RT | FGAGTNLEIK | 51 |
| 10 | QESTSYYGT | FGAGTKLEIK | 52 |
| 11 | QESTSYYGT | FGAGTKLEIK | 53 |
| 12 | QEYTSYYGT | FGGGTKLEIK | 54 |
| 13 | QQSRSYT | SAQDPNRKLI | 86 |
| 14 | QQSKTSPSL | LAEDQAEFMA | 87 |
| 15 | MQTFGTPGR | SALGQTGKKF | 88 |
| γ chains ||||
| 1 | ARGPLYSVGRAWSNYWYFDF | WGSGILVSVST | 19 |
| 2 | ARGPLYYVGRAWSNYWYFDF | WGSGILVSVST | 20 |
| 3 | ASGPLYRIGAVWSNYRSFDF | WGSGILVTVSS | 21 |
| 4 | ARGPLYYVGRAWSNYWYFDF | WGSGILVSVST | 22 |
| 5 | ARAQYFDV | WGAGTLVTVSS | 23 |
| 6 | ARSGSHSSGVYYIPSYFDV | WGAGTLVTVSS | 24 |
| 7 | ATDMGWNSALDV | WGPGTLVTVSS | 25 |
| 8 | ARHGSGYFDI | WGAGTLVTVSS | 26 |
| 9 | ATDMGWNSALDI | WGPGTLVIVSS | 27 |
| 10 | ASHGNGYDI | WGGGTLVTVSS | 28 |
| 11 | ARHGGGYFDI | WGAGTLVTVSS | 29 |
| 12 | TRHGSGYFDM | WGTGARVTVSS | 30 |
| 13 | ARAQFFDV | WGTGVLVTVSS | 89 |
| 14 | ARGPLYSIGGVWSNYGYFDF | WGSGILVSVSS | 90 |
| 15 | GSVGSLY | WGQGTLVTVSS | 91 |

Example 3

Preparation of Anti-Ovalbumin Rabbit Monoclonal Antibodies

Rabbits are known to produce high affinity antibodies that cannot be obtained from other animals. Accordingly, rabbit monoclonal antibodies were prepared using the present invention.

[Materials and Methodology]

Female six-week-old rabbits were employed as the immune animals. The antigen was ovalbumin. In immunization, 300 μg of ovalbumin was injected intramuscularly four times at one-month intervals on both sides of the tails of the rabbits. Once immunity had been established, the iliac lymph nodes were collected from the rabbits. The ovalbumin was fluorescence labeled with Alexafluor 488 and purified by gel filtration.

[Results]

Figure 10:
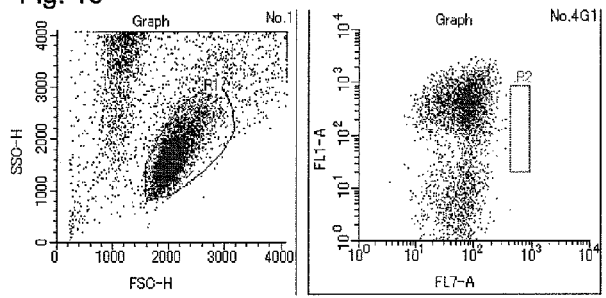
FIG. 10 Shows the results of Example 3. These results show that groups of cells that were ovalbumin positive and intensely ER-tracker positive were present.

Lymphocytes from the iliac lymph nodes were suspended in a 0.5% PBS bovine serum albumin solution, after which the Alexafluor 488 fluorescent labeled ovalbumin was added and the mixture was stirred for 30 minutes at 4° C. The cells were centrifuged and resuspended in PBS. To this was added ER-tracker (1 μm) and the mixture was left standing for 5 minutes at room temperature to stain the endoplasmic reticulum. The cells were then analyzed with a flow cytometer. As a result, the presence of ovalbumin positive and strongly ER-tracker positive plasma cells was observed (FIG. 10). These were adopted as an antigen specific plasma cell fraction.

cDNA Synthesis cDNA was synthesized and the immunoglobulin gene was amplified in accordance with the methods described in "Reaction device, reaction method and method of synthesizing cDNA" (WO2009/091048). Individual rabbit plasma cells that had been separated with a cell sorter were added to 3 μL of cell lysate (100 mM TrisHCl (pH 7.5), 500 mM LiCl, 1% lithium dodecylsulfate (LiDS), and 5 mM dithiothreitol) containing 3 μg of magnetic beads (Dynabeads) bonded to oligo-dT25. The mRNA in the cells was caused to bind to the magnetic beads. Next, the magnetic beads were washed once with 3 μL of mRNA cleaning solution A (10 mM TrisHCl (pH 7.5), 0.15 M LiCl, and 0.1% LiDS) followed by 3 μL of mRNA cleaning solution B (75 mM KCl, 3 mM MgCl2, 0.1% TritonX, 0.5 mM dNTP, 5 mM DTT, and 2 units of RNase inhibitor). cDNA was then synthesized. After washing, to the magnetic beads were added 3 μL of cDNA synthesis solution (50 mM TrisHCl (pH 8.3), 75 mM KCl, 3 mM MgCl2, 0.1% TritonX-100, 0.5 mM dNTP, 5 mM DTT, 2 units of RNase inhibitor, and 10 units of SuperScriptIII Reversetranscriptase (Invitrogen) and the mixture was reacted for one hour at 37° C. Next, the magnetic beads were washed with 3 μL of 3' tailing cleaning solution (50 mM potassium phosphate (pH 7.0), 0.5 mM dGTP, 0.1% TritonX-100, and 4 mM magnesium chloride). An additional 3 μL of 3' tailing reaction solution (50 mM potassium phosphate (pH 7.0), 0.5 mM dGTP, 0.1% TritonX-100, 4 mM magnesium chloride, and 10 units of terminal deoxynucleotidyl transferase) were added and the mixture was reacted for 30 minutes at 37° C.

Amplification of Rabbit γ and κ Chain Variable Region Gene Fragments

Magnetic beads were washed with 3 μL of TE solution (10 mM TrisHCl (pH 7.5), 1 mM EDTA, and 0.1% TritonX-100) after which the 5'-RACE PCR method was employed to amplify the human immunoglobulin γ chain and κ chain genes. In the first round PCR reaction, 25 μL of PCR reaction solution (containing 0.2 μM of each primer, 0.2 mM of dNTP, and 1 unit of TakaraBio PrimeSTAR heat-resistant DNA polymerase) was added to the magnetic beads and 35 cycles of reactions for 30 seconds at 94° C. and 40 seconds at 68° C. were conducted. The primer (a) employed was annealed to the poly-G added to the 3' end of the cDNA by TdT. Primer sequence (u) was derived from the constant region of the rabbit immunoglobulin γ chain gene. Primer sequence (v) was derived from the constant region of the rabbit immunoglobulin κ chain gene.

After the reaction, 225 μL of water was added to the PCR solution and 1 μL of the 10-fold diluted solution was employed as template. Primers (d) and (w) were employed to conduct an amplification reaction of the variable region of the rabbit immunoglobulin γ chain gene under the same conditions as in the first round PCR. Similarly, primers (d) and (x) were employed to conduct an amplification reaction of the variable region of the rabbit immunoglobulin κ chain gene (FIG. 11).

The primers employed were:

```
First round PCR γ chain amplification
antisense primer
                                  (SEQ ID NO: 80)
5-GCTGGCTGCTTGAGGTCACGCTCACCAC-3 (u)

First round PCR κ chain amplification
antisense primer
                                  (SEQ ID NO: 81)
5- CAGTTGTTTGGGTGGTGCCATCCAC-3 (v)

Second round PCR γ chain amplification
antisense primer
                                  (SEQ ID NO: 82)
5- CTGCCGGACGGACGGGAAGGTGCGTAC-3 (w)

Second round PCR κ chain amplification
antisense primer
                                  (SEQ ID NO: 83)
5- ACACACGATGGTGACTGTTCCAGTTG-3 (x)
```

Preparation of Rabbit Immunoglobulin Linearized Expression Vector

Expression units of rabbit γ chain gene and κ chain gene were prepared in accordance with the methods of "Method for Specifically Producing a Joined DNA Fragment Comprising a Sequence Derived from a Target Gene" (WO2011/027808). That is, to 1 μL quantities of individual PCR products amplified by the 5'-RACE-PCR method were added 2 units of terminal dexoynucleotidyl transferase and a reaction was conducted for 30 minutes at 37° C. Subsequently, heating was conducted for 5 minutes at 94° C. to halt the enzymatic reaction.

To the 3' end polynucleotide addition rabbit γ chain gene solution prepared above was added 10 ng of rabbit γ chain gene joining double-stranded DNA fragment, 10 pmol of primers (g) and (h), and 10 nmol of dNTP. TakaraBio PrimeSTAR heat-resistant DNA polymerase was employed in 25 μL of reaction solution to conduct five cycles of reactions of 40 seconds at 94° C. and 4 minutes at 70° C. followed by 30 cycles of reactions of 40 seconds at 94° C., 40 seconds at 60° C., and 4 minutes at 72° C. to prepare rabbit γ chain gene expression units.

Similarly, to a rabbit κ chain gene solution were added rabbit κ chain gene joining double-stranded DNA fragments and a reaction was conducted to prepare rabbit κ chain gene expression units.

Primers (g) and (h) were Employed in the Expression Unit Amplification.

Following the reaction, 1 μL quantities of PCR solution were measured out and the conversion to expression units of κ and γ chain immunoglobulin gene fragments was confirmed by agarose gel electrophoresis (FIG. 12).

Gene Joining Double-Stranded DNA Fragment

The rabbit γ chain gene joining double-stranded DNA fragment (SEQ ID NO: 84) consists of a rabbit γ chain constant region (1-893), a joining sequence II (1-93), a polyA addition signal (1065-1071), a CMV promoter (1606-2195), and a joining sequence 1 (2196-2230).

CTGGTCAAAGGCTACCTCCCGGAGCCAGTGACCGTGACCTGGAACTCGGG

CACCCTCACCAATGGGGTACGCACCTTCCCGTCCGTCCGGCAGTCCTCAG

GCCTCTACTCGCTGAGCAGCGTGGTGAGCGTGACCTCAAGCAGCCAGCCC

GTCACCTGCAACGTGGCCCACCCAGCCACCAACACCAAAGTGGACAAGAC
CGTTGCGCCCTCGACATGCAGCAAGCCCACGTGCCCACCCCCTGAACTCC
TGGGGGGACCGTCTGTCTTCATCTTCCCCCCAAAACCCAAGGACACCCTC
ATGATCTCACGCACCCCCGAGGTCACATGCGTGGTGGTGGACGTGAGCCA
GGATGACCCCGAGGTGCAGTTCACATGGTACATAAACAACGAGCAGGTGC
GCACCGCCCGGCCGCCGCTACGGGAGCAGCAGTTCAACAGCACGATCCGC
GTGGTCAGCACCCTCCCCATCGCGCACCAGGACTGGCTGAGGGGCAAGGA
GTTCAAGTGCAAAGTCCACAACAAGGCACTCCCGGCCCCCATCGAGAAAA
CCATCTCCAAAGCCAGAGGGCAGCCCCTGGAGCCGAAGGTCTACACCATG
GGCCCTCCCCGGGAGGAGCTGAGCAGCAGGTCGGTCAGCCTGACCTGCAT
GATCAACGGCTTCTACCCTTCCGACATCTCGGTGGAGTGGGAGAAGAACG
GGAAGGCAGAGGACAACTACAAGACCACGCCGGCCGTGCTGGACAGCGAC
GGCTCCTACTTCCTCTACAGCAAGCTCTCAGTGCCCACGAGTGAGTGGCA
GCGGGGCGACGTCTTCACCTGCTCCGTGATGCACGAGGCCTTGCACAACC
ACTACACGCAGAAGTCCATCTCCCGCTCTCCGGGTAAATGAGCGCGGCCG
CGACTCTAGATCATAATCAGCCATACCACATTTGTAGAGGTTTTACTTGC
TTTAAAAAACCTCCCACACCTCCCCCTGAACCTGAAACATAAAATGAATG
CAATTGTTGTTGTTAACTTGTTTATTGCAGCTTATAATGGTTACAAATAA
AGCAATAGCATCACAAATTTCACAAATAAAGCATTTTTTCACTGCATTC
TAGTTGTGGTTTGTCCAAACTCATCAATGTATCTTAAGGCGTAAATTGTA
AGCGTTAATATTTTGTTAAAATTCGCGTTAAATTTTGTTAAATCAGCTC
ATTTTTTAACCAATAGGCCGAAATCGGCAAAATCCCTTATAAATCAAAAG
AATAGACCGAGATAGGGTTGAGTGTTGTTCCAGTTTGGAACAAGAGTCCA
CTATTAAAGAACGTGGACTCCAACGTCAAAGGGCGAAAAACCGTCTATCA
GGGCGATGGCCCACTACGTGAACCATCACCCTAATCAAGTTTTTTGGGGT
CGAGGTGCCGTAAAGCACTAAATCGGAACCCTAAAGGGAGCCCCCGATTT
AGAGCTTGACGGGGAAAGCCGGCGAACGTGGCGAGAAAGGAAGGGAAGAA
AGCGAAAGGAGCGGGCGCTAGGGCGCTGGCAAGTGTAGCGGTCACGCTGC
GCGTAACCACCACACCCGCCGCGCTTAATGCGCCGCTACAGGGCGCGTCa
gatctTAGTTATTAATAGTAATCAATTACGGGGTCATTAGTTCATAGCCC
ATATATGGAGTTCCGCGTTACATAACTTACGGTAAATGGCCCGCCTGGCT
GACCGCCCAACGACCCCCGCCCATTGACGTCAATAATGACGTATGTTCCC
ATAGTAACGCCAATAGGGACTTTCCATTGACGTCAATGGGTGGAGTATTT
ACGGTAAACTGCCCACTTGGCAGTACATCAAGTGTATCATATGCCAAGTA
CGCCCCCTATTGACGTCAATGACGGTAAATGGCCCGCCTGGCATTATGCC
CAGTACATGACCTTATGGGACTTTCCTACTTGGCAGTACATCTACGTATT
AGTCATCGCTATTACCATGGTGATGCGGTTTTGGCAGTACATCAATGGGC
GTGGATAGCGGTTTGACTCACGGGGATTTCCAAGTCTCCACCCCATTGAC
GTCAATGGGAGTTTGTTTTGGCACCAAAATCAACGGGACTTTCCAAAATG
TCGTAACAACTCCGCCCCATTGACGCAAATGGGCGGTAGGCGTGTACGGT GGGAGGTCTATATAAGCAGAGCTGGTTTAGTGAACCGTCAGATCCGCTAG
CGCTACCGGACTCAGATCCCCCCCCCCCCCC Gene Joining Double-Stranded DNA Fragment The rabbit κ chain gene joining double-stranded DNA fragment (SEQ ID NO: 85) consists of a rabbit κ chain constant region (1-312), a joining sequence II (1-95), a polyA addition signal (507-513), a CMV promoter (1050-1633), and a joining sequence 1 (1640-1675).

ATCCAGTTGCACCTACTGTCCTCATCTTCCCACCAGCTGCTGATCAGGTG
GCAACTGGAACAGTCACCATCGTGTGTGTGGCGAATAAATACTTTCCCGA
TGTCACCGTCACCTGGGAGGTGGATGGCACCACCCAAACAACTGGCATCG
AGAACAGTAAAACACCGCAGAATTCTGCAGATTGTACCTACAACCTCAGC
AGCACTCTGACACTGACCAGCACACAGTACAACAGCCACAAAGAGTACAC
CTGCAAGGTGACCCAGGGCACGACCTCAGTCGTCCAGAGCTTCAACAGGG
GTGACTGCTAGAGCGGCCGCGACTCTAGATCATAATCAGCCATACCACAT
TTGTAGAGGTTTTACTTGCTTTAAAAAACCTCCCACACCTCCCCCTGAAC
CTGAAACATAAAATGAATGCAATTGTTGTTGTTAACTTGTTTATTGCAGC
TTATAATGGTTACAAATAAAGCAATAGCATCACAAATTTCACAAATAAAG
CATTTTTTCACTGCATTCTAGTTGTGGTTTGTCCAAACTCATCAATGTA
TCTTAAGGCGTAAATTGTAAGCGTTAATATTTTGTTAAAATTCGCGTTAA
ATTTTTGTTAAATCAGCTCATTTTTTAACCAATAGGCCGAAATCGGCAAA
ATCCCTTATAAATCAAAAGAATAGACCGAGATAGGGTTGAGTGTTGTTCC
AGTTTGGAACAAGAGTCCACTATTAAAGAACGTGGACTCCAACGTCAAAG
GGCGAAAAACCGTCTATCAGGGCGATGGCCCACTACGTGAACCATCACCC
TAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGG
CGAGAAAGGAAGGGAAGAAAGCGAAAGGAGCGGGCGCTAGGGCGCTGGCA
AGTGTAGCGGTCACGCTGCGCGTAACCACCACACCCGCCGCGCTTAATGC
GCCGCTACAGGGCGCGTCagatctTAGTTATTAATAGTAATCAATTACGG
GGTCATTAGTTCATAGCCCATATATGGAGTTCCGCGTTACATAACTTACG
GTAAATGGCCCGCCTGGCTGACCGCCCAACGACCCCCGCCCATTGACGTC
AATAATGACGTATGTTCCCATAGTAACGCCAATAGGGACTTTCCATTGAC
GTCAATGGGTGGAGTATTTACGGTAAACTGCCCACTTGGCAGTACATCAA
GTGTATCATATGCCAAGTACGCCCCCTATTGACGTCAATGACGGTAAATG
GCCCGCCTGGCATTATGCCCAGTACATGACCTTATGGGACTTTCCTACTT
GGCAGTACATCTACGTATTAGTCATCGCTATTACCATGGTGATGCGGTTT
TGGCAGTACATCAATGGGCGTGGATAGCGGTTTGACTCACGGGGATTTCC
AAGTCTCCACCCCATTGACGTCAATGGGAGTTTGTTTTGGCACCAAAATC
AACGGGACTTTCCAAAATGTCGTAACAACTCCGCCCCATTGACGCAAATG
GGCGGTAGGCGTGTACGGTGGGAGGTCTATATAAGCAGAGCTGGTTTAGT
GAACCGTCAGATCCGCTAGCGCTACCGGACTCAGATCCCCCCCCCCCCCC The full lengths of the rabbit γ chain, κ chain, and λ chain gene expression units amplified in the above experiments were genetically introduced into 293FT cells and the cells were cultured for two days to bring about the secretion of recombinant rabbit antibodies in the cell culture. The antigen-binding ability of the recombinant rabbit monoclonal antibodies obtained from the antigen specific and antigen nonspecific plasma cells was examined by the ELISA method (FIG. 13). As a result, the recombinant rabbit monoclonal antibodies obtained from antigen-specific plasma cells, exhibited a strong ability to bind to ovalbumin. Based on these results, based on just the operation of subjecting a lymphocyte suspension to the effects of labeled antigen and ER-tracker, it was clearly possible to identify antigen specific plasma cells and then highly efficiently prepare antigen specific rabbit monoclonal antibodies, as well.

INDUSTRIAL APPLICABILITY

The present invention is applicable to field relating to manufacturing antibodies.

The invention claimed is:

1. A method for selecting a plasma cell(s) and/or plasmablast(s) that specifically bind to a target antigen, comprising:
   either collecting lymph fluid, lymphoid tissue, blood cell sample, or bone marrow derived cells from a nonhuman animal, and sensitizing the lymphocytes, lymphoid tissue, blood cell sample, or bone marrow derived cells in vitro to the target antigen, or
   immunizing a nonhuman animal to the target antigen, and collecting lymph fluid, lymphoid tissue, blood cell sample, or bone marrow derived cells from the nonhuman animal once immunization has been established;
   mixing the sensitized or collected lymph fluid, lymphoid tissue, blood cell sample, or bone marrow derived cells with (1) a fluorescently-labeled target antigen through a membrane-bound antibody on the cell(s) and (2) a marker that selectively binds to plasma cells and/or plasmablasts; and
   selecting a cell(s) to which (1) the fluorescently-labeled target antigen and (2) the marker have bound;
   wherein the marker that selectively binds to plasma cells and/or plasmablasts is a fluorescent probe for staining identifying or isolating plasma cells and/or plasmablasts, wherein the staining selectivity for an endoplasmic reticulum in cells is higher than the staining selectivity for cell organelles other than an endoplasmic reticulum, and with the staining of the fluorescent probe, plasma cells and plasmablasts are distinguishable from cells other than plasma cells and plasmablasts.

2. A method for selecting a human plasma cell(s) and/or plasmablast(s) that specifically bind to a target antigen, comprising:
   either collecting lymph fluid, lymphoid tissue, blood cell sample, or bone marrow derived cells from a human, and sensitizing the lymphocytes, lymphoid tissue, blood cell sample, or bone marrow derived cells in vitro to the target antigen, or
   collecting lymph fluid, lymphoid tissue, blood cell sample, or bone marrow derived cells from a human having antibodies to the target antigen;
   mixing the sensitized or collected lymph fluid, lymphoid tissue, blood cell sample, or bone marrow derived cells with (1) a fluorescently-labeled target antigen through a membrane-bound antibody on the cell(s) and (2) a marker that selectively binds to plasma cells and/or plasmablasts; and
   selecting a cell(s) to which (1) the fluorescently-labeled target antigen and (2) the marker have bound;
   wherein the marker that selectively binds to plasma cells and/or plasmablasts is a fluorescent probe for staining identifying or isolating plasma cells and/or plasmablasts, wherein the staining selectivity for an endoplasmic reticulum in cells is higher than the staining selectivity for cell organelles other than an endoplasmic reticulum, and with the staining of the fluorescent probe, plasma cells and plasmablasts are distinguishable from cells other than plasma cells and plasmablasts.

3. The method according to claim 1, wherein the fluorescent probe is selected from the group consisting of (1) a substance which is amphiphilic and cationic and has moderate lipophilicity and (2) a substance which has affinity to a protein localized in an endoplasmic reticulum above a certain degree.

4. The method according to claim 3, wherein the amphiphilicity is defined by the amphiphilicity index (AI) as $+6 > AI > 0$, the moderate lipophilicity is defined by the hydrophobic index (log P) as $+6 > \log P > 0$, and the affinity above a certain degree is defined by the dissociation constant of the range of 0.1 pM to 0.1 nM.

5. The method according to claim 1, wherein the cell organelle other than an endoplasmic reticulum is plasma-membrane, mitochondria, Golgi body, lysosome, peroxisome, nucleus, centrosome, cytoplasm, phagosome, endosome, or aggresome.

6. The method according to claim 1, wherein the fluorescent probe is selected from the group consisting of fluorescent labeled glibenclamide, fluorescent labeled Brefeldin A, fluorescent probe, and fluorescent protein.

* * * * *